United States Patent
Miettinen-Oinonen et al.

(10) Patent No.: US 7,273,748 B2
(45) Date of Patent: Sep. 25, 2007

(54) CELLULASES, THE GENES ENCODING THEM AND USES THEREOF

(75) Inventors: Arja Miettinen-Oinonen, Masala (FI); John Londesborough, Helsinki (FI); Jari Vehmaanpera, Klaukkala (FI); Heli Haakana, Espoo (FI); Arja Mantyla, Helsinki (FI); Raija Lantto, Klaukkala (FI); Minna Elovainio, Helsinki (FI); Vesa Joutsjoki, Jokioinen (FI); Marja Paloheimo, Vantaa (FI); Pirkko Suominen, Helsinki (FI)

(73) Assignee: AB Enzymes Oy, Rajamaki (FI)

( * ) Notice: Subject to any disclaimer, the term of this patent is extended or adjusted under 35 U.S.C. 154(b) by 282 days.

(21) Appl. No.: 10/825,378

(22) Filed: Apr. 16, 2004

(65) Prior Publication Data

US 2004/0185498 A1  Sep. 23, 2004

Related U.S. Application Data

(60) Division of application No. 08/841,636, filed on Apr. 30, 1997, now Pat. No. 6,723,549, which is a continuation of application No. PCT/FI96/00550, filed on Oct. 17, 1996, and a continuation-in-part of application No. 08/732,181, filed on Oct. 16, 1996, now abandoned.

(60) Provisional application No. 60/020,840, filed on Jun. 28, 1996, provisional application No. 60/007,926, filed on Dec. 4, 1995, provisional application No. 60/005,335, filed on Oct. 17, 1995.

(51) Int. Cl.
| | |
|---|---|
| *D06M 16/00* | (2006.01) |
| *C12N 9/42* | (2006.01) |
| *C12P 21/06* | (2006.01) |
| *C11D 3/00* | (2006.01) |
| *C11D 9/42* | (2006.01) |
| *C07H 21/02* | (2006.01) |
| *C07H 21/04* | (2006.01) |

(52) U.S. Cl. ............. 435/263; 435/209; 435/203; 435/69.1; 435/267; 435/274; 435/277; 426/53; 510/392; 510/530; 536/23.1; 536/23.2

(58) Field of Classification Search ............. None
See application file for complete search history.

(56) References Cited

U.S. PATENT DOCUMENTS

| | | | |
|---|---|---|---|
| 3,438,864 A | 4/1969 | Tendler | |
| 3,664,961 A | 5/1972 | Norris | |
| 4,106,989 A | 8/1978 | Komura et al. | |
| 4,832,864 A | 5/1989 | Olson | |
| 4,894,338 A | 1/1990 | Knowles et al. | |
| 4,912,056 A | 3/1990 | Olson | |
| 5,006,126 A | 4/1991 | Olson et al. | |
| 5,120,463 A | 6/1992 | Bjork et al. | |
| 5,122,159 A | 6/1992 | Olson et al. | |
| 5,213,581 A | 5/1993 | Olson et al. | |
| 5,232,851 A | 8/1993 | Cox et al. | |
| 5,246,853 A | 9/1993 | Clarkson et al. | |
| 5,290,474 A | 3/1994 | Clarkson et al. | |
| 5,298,405 A | 3/1994 | Nevalainen et al. | |
| 5,443,750 A | 8/1995 | Convents et al. | |
| 5,520,838 A | 5/1996 | Baeck et al. | |
| 5,525,507 A | 6/1996 | Clarkson et al. | |
| 5,650,322 A | 7/1997 | Clarkson et al. | |
| 5,958,082 A * | 9/1999 | Lund et al. ............. 8/102 |
| 6,001,639 A | 12/1999 | Schulein et al. | |
| 6,184,019 B1 | 2/2001 | Miettinen-Oinonen et al. | |
| 6,723,549 B2 | 4/2004 | Miettinen-Oinonen et al. | |

FOREIGN PATENT DOCUMENTS

| | | |
|---|---|---|
| DE | 1 767 737 | 9/1971 |
| EP | 0 220 016 | 4/1987 |
| EP | 0 238 216 | 9/1987 |
| EP | 0 307 564 | 3/1989 |
| EP | 0 383 828 | 8/1990 |
| EP | 0 406 314 | 1/1991 |
| EP | 0 510 091 | 10/1992 |
| EP | 0 521 999 | 1/1993 |
| EP | 0 531 372 | 3/1993 |
| EP | 0 576 526 | 1/1994 |
| GB | 2 075 028 | 11/1981 |
| WO | WO89/09259 | 10/1989 |
| WO | WO91/14822 | 10/1991 |

(Continued)

OTHER PUBLICATIONS

Schuelein, M, et al. (2002) Sequence search, ABB04137.*

(Continued)

*Primary Examiner*—Rebecca E. Prouty
*Assistant Examiner*—Ganapathirama Raghu
(74) *Attorney, Agent, or Firm*—Sterne, Kessler, Goldstein & Fox, PLLC

(57) ABSTRACT

Genes encoding novel cellulases, and a gene encoding a protein that facilitates the action of such novel cellulases, the novel cellulases and a protein that facilitates the action of such cellulases, and enzyme preparations containing such proteins are described. The native hosts and the culture medium of said hosts containing said novel cellulases are also disclosed. These proteins are especially useful in the textile and detergent industry and in pulp and paper industry.

74 Claims, 37 Drawing Sheets

FOREIGN PATENT DOCUMENTS

| WO | WO91/17243 | 11/1991 |
| --- | --- | --- |
| WO | WO91/17244 | 11/1991 |
| WO | WO92/06165 | 4/1992 |
| WO | WO92/06209 | 4/1992 |
| WO | WO92/06210 | 4/1992 |
| WO | WO92/06221 | 4/1992 |
| WO | WO92/17572 | 10/1992 |
| WO | WO92/17574 | 10/1992 |
| WO | WO92/18599 | 10/1992 |
| WO | WO93/11249 | 6/1993 |
| WO | WO93/22428 | 11/1993 |
| WO | WO93/24621 | 12/1993 |
| WO | WO93/24622 | 12/1993 |
| WO | WO94/07983 | 4/1994 |
| WO | WO94/07998 | 4/1994 |
| WO | WO94/14953 | 7/1994 |
| WO | WO94/23113 | 10/1994 |
| WO | WO95/02675 | 1/1995 |
| WO | WO95/16782 | 6/1995 |
| WO | WO95/24471 | 9/1995 |
| WO | WO95/25840 | 9/1995 |
| WO | WO96/17994 | 6/1996 |
| WO | WO96/29397 | 9/1996 |
| WO | WO96/34945 | 11/1996 |

OTHER PUBLICATIONS

Aho, S., et al., "Monoclonal antibodies against core and cellulose-binding domains of *Trichoderma reesei* cellobiohydrolases I and II and endoglucanase I," *Eur. J. Biochem. 200*:643-649, Springer International (1991).

Bailey, M.J. and Nevalainen, K.M.H., "Induction, isolation and testing of stable *Trichoderma reesei* mutants with improved production of solubilizing cellulase," *Enzyme Microb. Technol. 3*:153-157, Elsevier (1981).

Bhat, K.M., et al., "The Endo-(1→4)-β-D-glucanase System of *Penicillium pinophilum* Cellulase: Isolation, Purification, and Characterization of Five Major Endoglucanase Components," *Carbohydrate Res. 190*:279-297, Elsevier Science Publishers B.V. (1989).

Bhikhabhai, R., et al., "Isolation of Cellulolytic Enzymes from *Trichoderma reesei* QM 9414," *J. Appl. Biochem. 6*:336-345, Academic Press, Inc. (1984).

Bowie, J.U., et al., "Deciphering the Message in Protein Sequences: Tolerance to Amino Acid Substitutions," *Science 247*:1306-1310, American Association for the Advancement of Science (1990).

Bühler, R., "Double-Antibody Sandwich Enzyme-Linked Immunosorbent Assay for Quantitation of Endoglucanase I of *Trichoderma reesei,*" *Appl. Environ. Microbiol. 57*:3317-3321, American Society for Microbiology (1991).

Commission on Biotechnology, *Measurement of Cellulase Activities*, Commission on Biotechnology, International Union of Pure and Applied Chemistry, Indian Institute of Technology, Delhi, 17 pages (1984).

Davies, G.J., et al., "Structure and function of endoglucanase V," *Nature 365*:362-364, Nature Publishing Company (1993).

El-Gindy, A.A., "Production of Cellulase(s) by *Myriococcum albomyces,*" *Zentralbl. Mikrobiol. 146*:193-196, Gustav Fischer Verlag Jena (1991).

Harkki, A., et al., "Genetic engineering of *Trichoderma* to produce strains with novel cellulase profiles," *Enzyme Microb. Technol. 13*:227-233, Elsevier (1991).

Henrissat, B. and Bairoch, A., "New families in the classification of glycosyl hydrolases based on amino acid sequence similarities," *Biochem. J. 293*:781-788, The Biochemical Society (1993).

Karhunen, T., et al., "High frequency one-step gene replacement in *Trichoderma reesei*. I. Endoglucanase I overproduction," *Mol. Gen. Genet. 241*:515-522, Springer Verlag (1993).

Klahorst, S., et al., "Optimizing the Use of Cellulases for Denim Finishing," *AATCC Int. Conf. & Exhibit.*, Atlanta, GA, pp. 243 (1992).

Klahorst, S., et al., "Optimizing the Use of Cellulase Enzymes," *Textile Chemist and Colorist 26*:13-18, Enzyme Technical Association (Feb. 1994).

Kochavi, D., et al., "Optimizing Processing Conditions in Enzymatic Stonewashing," *Am. Dyestuff Reporter 79*:24, 26, 28, SAF Publications Inc. (1990).

Lange, N.K., "Application of cellulases in the textile industry," in: *Trichoderma ressei Cellulases and Other Hydrolases*, Suominen, P. and Reinikainen, T., eds., Foundation for Biotechnical and Industrial Fermentation Research, Espoo, Finland, pp. 263-272 (1993).

Lantto, R., et al., "Backstaining in Denim Wash With Different Cellulases," *Am. Dyestuff Reporter. 85*:64-65, 72, SAF Publications Inc. (Aug. 1996).

Latif, F., et al., "Saccharification of *Leptochloa fusca* (Kallar Grass Straw) Using Thermostable Cellulases," *Biores. Technol. 50*:107-111, Elsevier Science Ltd. (Jul. 1994).

Mach, R.L., et al., "Transformation of *Trichoderma reesei* based on hygromycin B resistance using homologous expression signals,"*Curr. Genet. 25*:567-570, Springer International (Jun. 1994).

Mandels, M. and Reese, E.T., "Induction of Cellulase in *Trichoderma viride* as Influenced by Carbon Sources and Metals," *J. Bacteriol. 73*:269-278, The Williams & Wilkins Company (1957).

Mattern, I.E., et al., "Transformation of *Aspergillus oryzae,*" in: *Abstracts of the 19th Lanteren Lectures on Molecular Genetics of Yeasts and Filamentous Fungi and its Impact on Biotechnology*, p. 34 (1987).

Miettinen-Oinonen, A., "Effects of Cellulases on Cotton Fiber and Fabric," *Proc. Of the 77th World Conf. of the Textile Inst. 1*:197-207, The Textile Institute (May 1996).

Moloney, A.P., "Cellulose Hydrolysis by the Cellulases Produced by *Talaromyces emersonii*when Grown on Different Inducing Substrates," *Biotechnol. & Bioeng. 25*:1169-1173, John Wiley & Sons, Inc. (1983).

Nevalainen, H., "Genetic improvement of enzyme production in industrially important fungal strains," Presented at *The University of Helsinki*, VTT, Technical Research Centre of Finland, Publications 26, Espoo, Finland, pp. 3-58 (1985).

Nilsson, T.E., "Enzymes for the Textile Industry—Traditional and New Applications," Presented at *Aachen Textile Conference*, Nov. 1994, published in *DWI Reports 114*:85-88, Das Institut (Feb. 1995).

Offord, D.A., et al., "Preparative Purification of *Trichoderma reesei* Native and "Core" Cellobiohydrolase I by Electrophoresis and Chromatofocusing," *Appl. Biochem. & Biotechnol. 28/29*:377-386, The Humana Press (1991).

Penttilä, M., et al., "Homology between cellulase genes of *Trichoderma reesei*: complete nucleotide sequence of the endoglucanase I gene," *Gene 45*:253-263, Elsevier Science Publishers B.V. (1986).

Penttilä, M., et al., "A versatile transformation system for the cellulolytic filamentous fungus *Trichoderma reesei,*" *Gene 61*:155-164, Elsevier Science Publishers B.V. (1987).

Saloheimo, M., et al., "EGIII, a new endoglucanase from *Trichoderma reesei*: the characterization of both gene and enzyme," *Gene 63*:11-21, Elsevier Science Publishers B.V. (1988).

Saloheimo, A., et al., "A novel, small endoglucanase gene, *egl5*, from *Trichoderma reesei* isolated by expression in yeast," *Molec. Microbiol. 13*:219-228, Blackwell Scientific Publications (1994).

Schindler, M., et al., "Characterization of the pyruvate kinase-encoding gene (pkiI) of *Trichoderma reesei,*" *Gene 130*:271-275, Elsevier Science Publishers B.V. (1993).

Schülein, M., "Cellulases of *Trichoderma reesei,*" *Meth. Enzymol. 160*:234-242, Academic Press, Inc. (1988).

Schülein, M., et al., "*Humicola insolens* Alkaline Cellulases," in: *Proceedings of the Second TRICEL symposium on Trichoderma reesei Cellulases and Other Hydrolases*, Suominen, P. and Reinikainen, T., eds., Foundation for Biotechnical and Industrial Fermentation Research, Espoo, Finland, pp. 109-116 (1993).

Shoemaker, S., et al., "Molecular Cloning of Exo-Cellobiohydrolase I Derived from *Trichoderma reesei* Strain L27," *Bio/Technol. 1*:691-696, Nature Publishing Company (1983).

Suominen, P.L., et al., "High frequency one-step gene replacement in *Trichoderma reesei*. II. Effects of deletions of individual cellulase genes," *Mol. Gen. Genet. 241*:523-530, Springer-Verlag (1993).

Teeri, T., et al., "The Molecular Cloning of the Major Cellulase Gene from *Trichoderma reesei*," *Bio/Technol. 1*:696-699, Nature Publishing Company (1983).

Teeri, T. T., "The cellulolytic enzyme system of *Trichoderma reesei*: Molecular cloning, characterization and expression of the cellobiohydrolase genes," *Presented at the University of Helsinki, VTT, Technical Research Centre of Finland Publications 38*, Espoo, Finland, pp. 1-52 (1987).

Teeri, T., et al., "Homologous domains in *Trichoderma reesei* cellulolytic enzymes: gene sequence and expression of cellobiohydrolase II," *Gene 51*:43-52, Elsevier Science Publishers B.V. (1997).

Tomme, P., et al., "Studies of the cellulolytic system of *Trichoderma reesei* QM 9414: Analysis of domain function in two cellobiohydrolases by limited proteolysis," *Eur. J. Biochem. 170*:575-581, Blackwell Science Ltd. (1988).

Tyndall, R.M., "Application of Cellulase Enzymes to Cotton Fabrics and Garments," *AATCC Book of Papers: 1991 International Conference & Exhibition*, American Association of Textile Chemists and Colorists, Research Triangle Park, NC, pp. 269-273 (1991).

Tyndall, R. M., "Improving the Softness and Surface Appearance of Cotton Fabrics and Garments by Treatment with Cellulase Enzymes," *Textile Chemist & Colorist 24*:23-26, Enzyme Technical Association (1992).

van Tilbeurgh, H., et al., "Fluorogenic and Chromogenic Glycosides as Substrates and Ligands of Carbohydrates," *Methods Enzymol. 160*:45-59, Academic Press (1988).

Videbaek, T., et al., "The jeans effect comes into being," *ITB Dyeing/Printing/Finishing 1*:25-29, Bandung Institute of Technology (1994).

Wood, T.M., et al., "Aerobic and Anaerobic Fungal Cellulases, with Special Reference to Their Mode of Attack on Crystalline Cellulose," in: *Biochemistry and Genetics of Cellulose Degradation*, Aubert, J.-P., et al., eds., Academic Press, London, UK, pp. 31-52 (1988).

"Celluzyme™," Product Sheet, Detergent Enzymes Division, Novo Nordisk A/S, 2 pages (date unknown).

"Denimax™ T," Product Sheet, Enzyme Process Division, Novo Nordisk A/S, 1 page (date unknown).

"Denimax™ L," Product Sheet, Enzyme Process Division, Novo Nordisk A/S, 1 page (date unknown).

"Denimax™ PB," Product Sheet, Enzyme Process Division, Novo Nordisk A/S, 1 page (date unknown).

"Denimax® BT," Product Sheet, NOVO Enzyme Process Division, Novo Nordisk A/S, 1 page (date unknown).

International Search Report for International Patent Appl. No. PCT/FI96/00550, mailed Feb. 14, 1997, European Patent Office, Netherlands.

Biotechnology Abstracts, Accession No. 91-08942, abstract for El-Gindy, A.A., "Production of cellulase(s) by *Myriococcum albomyces*," *Zbl. Mikrobiol. 146*:193-196, Gustav Fischer Verlag Jena (1991) (Document AT3).

Biotechnology Abs., Accession No. 95-04270, Abstract for Latif, F., et al., "Saccharification of *Leptochloa fusca* (Kallar Grass Straw) Using Thermostable Cellulases," *Biores. Technol. 50*:107-111, Elsevier Science Ltd. (1994) (Document AT6).

STNEasy Database, Accession No. DE1767737, no English abstract available for DE 1 767 737 (Document AL1).

Co-pending U.S. Appl. No. 10/782,002, inventors Miettinen-Oinonen et al., filed Feb. 20, 2004 (Not Published).

* cited by examiner

429
ANGQSTRYWDCCKPSCGWRGKGPVNQPVYS

430
YGGISSR

431
CGWR

432
PSCGWR

433
YWDCCK

439
QECDSFPEPLKPGCQWR fr 9
RHDDGGFA fr 14
YWDCCKP fr 16
GKGPVNQPVYSCDANFQR fr 17
VQCPEELVAR fr 28
DWFQNADNPSFTFER fr 30
TMWQSTSTGGDLGSNHFDLNIPGGGVGLF

FIG.17

```
        -30               -20               -10                 1                10                20                30                40                50
TCGCCCCTAACCGAGAACCAAAGACTCCAAGAATGCGCTCTACTCCCGGTTCTCCGGCCCTCCTGGCCGCAGCATTGCCCCTGGGGGCCCTCGCGCCAA
                                    M  R  S  T  P  V  L  R  A  L  L  A  A  A  L  P  L  G  A  L  A ↓ A  N 60                70                80                90               100               110               120               130               140               150
CGGTCAGTCCACGAGgtaactgatcacccgctcattacgcgtgccgaccggcgttcagggctcactgctcaccgcatccagATACTGGGACTGCT
 G  Q  S  T  R                                                                          Y  W  D  C  C 160               170               180               190               200               210               220               230               240               250
GCAAGCCGTCGTGCGGCTGGCGGGAAAGGGCCCCGTGAACCAGCCGTCTACTGTGCGACGCCAACTTCCAGCGCATCCACGACTTCGATGCCGTCTC
 K  P  S  C  G  W  R  G  K  G  P  V  N  Q  P  V  Y  S  C  D  A  N  F  Q  R  I  H  D  F  D  A  V  S 260               270               280               290               300               310               320               330               340               350
GGGCTGGCGAGGGCGGCCCCGCCTTCTCGTGCGCCGACCACAGCCCCTGGGCCATTAATGACAACCTCTCGTACGGCTTCGCGGCGACTGCACTCAGCGGC
 G  C  E  G  G  P  A  F  S  C  A  D  H  S  P  W  A  I  N  D  N  L  S  Y  G  F  A  A  T  A  L  S  G 360               370               380               390               400               410               420               430               440               450
CAGACCGAGGAGTCGTGGTGCTGTGCCTGCTACGCgtgagtgtgcttgggccaacgtcggtgattccggagttcagacacactgaccagcgacccgctc
 Q  T  E  E  S  W  C  C  A  C  Y  A
```

FIG.19A

```
470
     .         .         .         .         .         .
gccagTCTGACCTTTACATCGGGTCCCGTGTGGCCGGCAAGACCATGGTCGTCCAGTCGACCAGCACGGGCGGCGACCTCGGCAGCAACCACTTCGACCTCA
 L T  F T S G P V A G K T M V V Q S T S T G G D L G S N H F D L N
          490       510       530       550

.         .         .         .         .         .
ACATCCCCGGCGGCGGCGTCGGCCTCTTCGACGGCTGCACTCCCCAGTTCGGCGGCCTCCCCGGCGCGCGGTACGGCGGCATCTCGTCGCGCCAGGAGTG
 I P  G G G V G L F D G C T P Q F G G L P G A R Y G G I S S R Q E C
          590       610       630       650

.         .         .         .         .         .
CGACTCGTTCCCCGAGCCGCTCAAGCCCGGCTGCCAGTGGCGCTTCGACTGGTTCCAGAACGCCGACAACCCGTCCTTTACCTTCGAGCGGGTCCAGTGC
 D S  F P E P L K P G C Q W R F D W F Q N A D N P S F T F E R V Q C
          690       710       730       750

.         .         .         .         .         .
CCCGAGGAGCTGGTCGCCCGCACCGGCTGCCGGCGGCACGACGACGGCGGCTTCGCCGTCTTCAAGGCCCCCAGCGCCTGATCCGTTTTTGGGCAGTGTC
 P E  E L V A R T G C R R H D D G G F A V F K A P S A *
          790       810       830       850

.
CGTGTGACGGGCAGCTACGTGGAACGACCTGGAGCTC
          890
```

Fig. 19B

```
-230                -210                -190                -170                -150
GAATTCGGGGGTTGCCAGGGAGTCGTACAGGGGTGGGTGGAGGGGGATGGAGAGAAAGCATATATGGGACGTTTGTGCTC

-130                -110                -90                 -70                 -50
GCCGGCTCCCCTCTGCCACGTTCCCTTGCCTGGGTTGTTGTTGGTCTTCCCTTCACCATCCGACAAACCAACCTGCTGCGGGTGAACTCGCA

-30                 -10                 10                  30                  50
GAGGCGCCTTCGGACGACGACAGAACGCACCATGACTCGCAACATCGCCCTGCTCGGCGCCGTCGGCGCTCCTGGGCCTCGCCCACGGCCAGAAGC
                         M  T  R  N  I  A  L  L  G  A  A  S  A  L  L  G  L  A  H  G  Q  K  P 70                  90                  110                 130                 150
CGGGGCGAGACGCCCGAGGTGCACCCGCAGCTGACGACGTTCCGGTGCACCAAGGCGGACGGTTGCCAGCCGCGGACCAACTACATTGTGCTGGACTCGCT
 G  E  T  P  E  V  H  P  Q  L  T  T  F  R  C  T  K  A  D  G  C  Q  P  R  T  N  Y  I  V  L  D  S  L 170                 190                 210                 230                 250
GTCGCACCCGGTGCACCAGGTGGACAACGACTACAACTGCGGCGACTGGGGCCAGAAGCCCAACGGACGGGTGCCCGACGTCGAGTCGTGCGCGCGC
 S  H  P  V  H  Q  V  D  N  D  Y  N  C  G  D  W  G  Q  K  P  N  A  T  A  C  P  D  V  E  S  C  A  R 270                 290                 310                 330                 350
AACTGCATCATGGAGGGCGTGCCCGACTACAGCCAGCACGGCGTCACGACGAGCGACACGTCGCTGCGCCTGCAGCAGCTTCGTCGACGGCCGCCTCGTCA
 N  C  I  M  E  G  V  P  D  Y  S  Q  H  G  V  T  T  S  D  T  S  L  R  L  Q  Q  L  V  D  G  R  L  V  T
```

FIG.21A

```
                                    390                       410                       430                       450
CGCCGGCGGTCTACTGCTCGACGAGACCGAGCACCGCTACGAGATGATGCACCTGACCGGCCAGGAGTTCACCTTTGAGGTCGACGCCACCAAGCTGCC
 P  R  V  Y  L  L  D  E  T  E  H  R  Y  E  M  M  H  L  T  G  Q  E  F  T  F  E  V  D  A  T  K  L  P 490                       510                       530                       550
CTGCGCGCATGAACAGCGCCCTCTACCTGTCCGAGATGGACCCGGCCCGCTCGGAGCTCAACCCCGGCGGTGCCTACTACGGCACCGGCTACTGC
 C  G  M  N  S  A  L  Y  L  S  E  M  D  P  P  T  G  A  R  S  E  L  N  P  G  G  A  Y  Y  G  T  G  Y  C 590                       610                       630                       650
GACGCCCAGTGCTTCGTGACGCCATTCATCAACGGCATTgtgagtgttccccttttggccccccctgaaaatagatgtacctgggtgctaaccccggg
 D  A  Q  C  F  V  T  P  F  I  N  G  I 690                       710                       730                       750
tgtcgcaccaaaacaggGCAACATCGAGGGCAAGGGCTCGTGCTGCAACGAGATGGACATCTGGGAGGCCAACTCGGGCCGCGCGACGCACGTGGCCGCGCAC
                  G  N  I  E  G  K  G  S  C  C  N  E  M  D  I  W  E  A  N  S  R  A  T  H  V  A  P  H 790                       810                       830                       850
ACGTGCAACCAGACGGGTCTGTACATGTGCGAGGGCGCCGAGTGCGAGTACGACGGCGTGTGCGACAAGGACGGCTGCGGGTGGAACCCGTACCGGGTCA
 T  C  N  Q  T  G  L  Y  M  C  E  G  A  E  C  E  Y  D  G  V  C  D  K  D  G  C  G  W  N  P  Y  R  V  N 890                       910                       930                       950
ACATCACCGACTACTACGGCAACTCGGACGCGTTCCGCGTCGACACGCGGCGGCCCTTCACCGTGGTGACGCAGTTCCCGGCCGACGCCGAGGGCCGGCT
 I  T  D  Y  Y  G  N  S  D  A  F  R  V  D  T  R  R  P  F  T  V  V  T  Q  F  P  A  D  A  E  G  R  L
```

FIG. 21B

```
              980         990        1000        1010        1020        1030        1040        1050
CGAGAGCATCCACCGGCTGTACGTGCAGGACGGCAAGGTGATCGAGTCGTACGTCGTCGACGCGCCGGGCCTGCCCCGGACGGACTCGCTCAACGACGAG
 E  S  I  H  R  L  Y  V  Q  D  G  K  V  I  E  S  Y  V  V  D  A  P  G  L  P  R  T  D  S  L  N  D  E 1080        1090        1100        1110        1120        1130        1140        1150
TTCTGCGCCGCCACGGGGGCGCCCGGCTACCTCGACCTCGGCGGCACCGCGGGCATGGGCGACGCCATGACGCGGGGCATGGTGCTGGCCATGAGCATCT
 F  C  A  A  T  G  A  A  R  Y  L  D  L  G  G  T  A  G  M  G  D  A  M  T  R  G  M  V  L  A  M  S  I 1180        1190        1200        1210        1220        1230        1240        1250
GGTGGGACGAGTCCGGCTTCATGAACTGGCTCGACAGCGGGGAGGCCGGCCCCTGCCTGCCCGACGAGGGCGACCCCAAGAACATTGTCAAGGTCGAGCC
 W  D  E  S  G  F  M  N  W  L  D  S  G  E  A  G  P  C  L  P  D  E  G  D  P  K  N  I  V  K  V  E  P 1280        1290        1300        1310        1320        1330        1340        1350
CAGCCCCGAGGTCACCTACAGCAACCTGCCTCGGGGCGAGATCGGGTCGACCTTTGAGGCCGAGTCCGACGACGACGGCGACGGCGACGACTGCTAGATA
 S  P  E  V  T  Y  S  N  L  R  W  G  E  I  G  S  T  F  E  A  E  S  D  D  D  G  D  G  D  D  C  *

1380        1390        1400        1410        1420        1430        1440        1450
ACTAACTAGTGGGCGGAAAGGGCGGGGGATGCGTAACTTACATACAGCCCGGAGTTGTTTTGAGTGTAGAGTATTGAGCTTTCGATGTGTTAGTTGAGTG 1480        1490        1500        1510        1520        1530        1540        1550
GAATGGAAAATTCGCGTCTTTGCCCCGGTGTTGCGATAAACAATAGTCGGCTGGTGCATTTGTGACACTTCAATTGCGCTGTTGGCTTGGTGACAGACA 1580        1590        1600        1610        1620        1630        1640        1650
CGGCAGCGTCGATGACCCGACACCCAGAATAATTCGCATGGTTGATTANTGTTATTGTGCTTTAAATCGGAGGCTGATGCTCATCTCTTCGAATTC

FIG.21C
```

```
-150                    -130                    -110                     -90                     -70
CCCGGTCTGGAGAGACGGGGAGCGCGCCAGCGACGCAGGATAAGAAGGCGACGACGCGCTCCGAGCCCAGGCCAGGACAGCAGGAGAACTCGGCACGCGC

-50                     -30                     -10                      10                      30
AAGCAGCACGCCGATCGACAGTGTCCCGCTCTGCCCACAGCACTCTGCAACCATGATGATGAAGCAGTACCTCCAGTACCTGGCGGCGGCTGCCGCT
                                                          M  M  M  K  Q  Y  L  Q  Y  L  A  A  A  L  P  L 50                      70                      90                     110                     130
CGTCGGCCTCGCCGCGGCCAGCGGCTGGTAACGAGAGCGGCGCTGGTAACGAGACGCCCGAGAACCACCCCCCGCTCACCTGGCAGAGGTGCACGGCCCCGGGCAACTGCCAGACC
 V  G  L  A  A  G  Q  R  A  G  N  E  T  P  E  N  H  P  P  L  T  W  Q  R  C  T  A  P  G  N  C  Q  T 150                     170                     190                     210                     230
GTGAACGCGAGGTGCGTCATTGACGCTGAGAAGTGCATGATCGAGGGTGCCGGCGACTACCTGGGCACTACGTACGGAGCCAGCACCAGTGGACGCAACCAGCCTGCAGCA
 V  N  A  E  V  V  I  D  A  N  W  R  W  L  H  D  D  N  M  Q  N  C  Y  D  G  N  Q  W  T  N  A  C  S  T 250                     270                     290                     310                     330
CCGCCACCGACTGCGCTGAGAAGTGCATGATCGAGGGTGCCGGCGACTACCTGGGCACTACGTACGGAGCCAGCACCAGTGGCGACGCCCTGACGCTCAAGTT
 A  T  D  C  A  E  K  C  M  I  E  G  A  G  D  Y  L  G  T  Y  G  A  S  T  S  G  D  A  L  T  L  K  F 350                     370                     390                     410                     430
CGTCACCAAGCACGAGTACGGCACCAACGTCGGCTCGCGCTTCTACCTCATGAACGGCCCGGACAAGTACCAGATGTTCAACCTCATGGGCAACGAGCTT
 V  T  K  H  E  Y  G  T  N  V  G  S  R  F  Y  L  M  N  G  P  D  K  Y  Q  M  F  N  L  M  G  N  E  L
```

FIG. 23A

```
450                   470                   490                   510                   530
GCCTTTGACGTCGACCTCTCGACGTCGAGTGCGGGCATCAACAGCGCCCTGTACTTCGTCGCCATGGAGGAGGACGGCGGCATGGCCAGCTACCCGAGCA
 A  F  D  V  D  L  S  T  V  E  C  G  I  N  S  A  L  Y  F  V  A  M  E  E  D  G  G  M  A  S  Y  P  S  N 550                   570                   590                   610                   630
ACCAGGCGCGGCGCCGGTACGGCACTGGGgtgagttgagctccgctttgtttcgagtcgcaacgaggcactttctgggcgccgctaactctctgattc
 Q  A  G  A  R  Y  G  T  G 650                   670                   690                   710                   730
ctccgacagTACTGCGATGCCCAATGCGCTCGTGATCTCAAGTTCGTTGGCGGCAAGGCCAACATTGAGGGCTGGAAGTCGTCCACCAGCGACCCCAACG
            Y  C  D  A  Q  C  A  R  D  L  K  F  V  G  G  K  A  N  I  E  G  W  K  S  S  T  S  D  P  N  A 750                   770                   790                   810                   830
CTGGCGTGGGCCCGTACGGCAGCTGTGCGCTGAGATCGACGTCTGgtgagtgcgagaccgtccaccaggttcggatgcggggtggaatttcgcggct
 G  V  G  P  Y  G  S  C  C  A  E  I  D  V  W 850                   870                   890                   910                   930
aacggagcacccccaggGAGTCGAATGCCTATGCCTTCGCTTTCACGCCGCACGCGTGCACGACCAACGAGTACCACGTCTGCGAGACCACCAACTGCG
                    E  S  N  A  Y  A  F  A  F  T  P  H  A  C  T  T  N  E  Y  H  V  C  E  T  T  N  C  G 950                   970                   990                   1010                  1030
GTGGCACCTACTCGGAGGACCGCTTCGCCGGCAAGTGCGACGCCAACGGCTGCGACTACAACCCCTACGCATGGGCAACCCGACTTCTACGGCAAGGG
 G  T  Y  S  E  D  R  F  A  G  K  C  D  A  N  G  C  D  Y  N  P  Y  R  M  G  N  P  D  F  Y  G  K  G 1050                  1070                  1090                  1110                  1130
CAAGACGCTCGACACCAGCCGCAAGTTCACgtgcgtgaccctgtggcgcaaccttctctgcctggacacactgaaactgacacgtcgttttcg
 K  T  L  D  T  S  R  K  F  T
```

FIG.23B

```
1150              1170                  1190                 1210                  1230
      gctgcagCGTGTCTCCCGCTTCGAGGAGAACAAGCTCTCCCAGTACTTCATCCAGGACGGCCGCAAGATCGAGATCCCGCCGACGTGGGAGGGCAT
              V  V  S  R  F  E  E  N  K  L  S  Q  Y  F  I  Q  D  D  G  R  K  I  E  I  P  P  T  W  E  G  M 1250              1270                  1290                 1310                  1330
      GCCCAACAGCAGCGAGATCACCCCGAGCTCTGCTCCACCATGTTCGATGTGTTCAACGACCGCAACCGCTTCGAGGAGGTCGGCGGCTTCGAGCAGCTG
       P  N  S  S  E  I  T  P  E  L  C  S  T  M  F  D  V  F  N  D  R  N  R  F  E  E  V  G  G  F  E  Q  L 1350              1370                  1390                 1410                  1430
      AACAACGCCCTCCGGGTTCCCATGGTCCTCGTCATGTCCATCTGGGACGACgtaagtaccccgccagctccctagcacacaagccgcatccggcgaggc
       N  N  A  L  R  V  P  M  V  L  V  M  S  I  W  D  D 1450              1470                  1490                 1510                  1530
      acgccatcgctgctaacacgagaccgttcgtagCACTACGCCAACATGCTCTGGCTCGACTCCATCTACCCGCCGAGAAGGAGGCCAGCCCGGCG
                                       H  Y  A  N  M  L  W  L  D  S  I  Y  P  P  E  K  E  G  Q  P  G  A 1550              1570                  1590                 1610                  1630
      CCGCCCGTGGGACTGCCCGGGACTCGGGTGTCCCGCCGAGGTCGAGGCTCAGTTCCCCGACGgtaagacttgccccgacccccaagcttccactt
       A  R  G  D  C  P  T  D  S  G  V  P  A  E  V  E  A  Q  F  P  D  A 1650              1670                  1690                 1710                  1730
      ctggatgccaatgctaacacgcgaaacagCCAGGTGGTCTGGTCCAACATCCGCTTCGGCCCCATCGGCTCGACTTACGACTTCTAAGCCGGTCCATGC
                                   Q  V  V  W  S  N  I  R  F  G  P  I  G  S  T  Y  D  F  *

1750              1770                  1790                 1810                  1830
      ACTCGGCAGCCCTGGGCCCGTCACGCCCGCCACCTCCCCCTGCGGGAAACTCTCCGTGCTGCGCGGGCTCCAAAGCATTTTGGCCTCAAGTTTTTTCGTTC
```

FIG.23C

```
          10                    30                    50                    70                    90
CCATGGACGCGAACTGCGACGTCTTTCTGCCCCGAGCTGAAAGACCCAGAGCATCCAGACGGGCAACCAGTGCACCCAGGAGATGAAGGTCTACGAGAACAT 110                   130                   150                   170                   190
TGACGGCTGCTCGACAGCCTGCCCGGCAACGTCCCCATCACCGGTCCGCAGCCGGCTCTGGTAAGTCAAAGAGATGATGCCTACTACCTTCCCACCT 210                   230                   250                   270                   290
TCCCACCCAGCGCGCAAATACCTTTCTCCCTCCCCGTGCCCCCGTATTCTTTCAACGCCCCGAGACTGACAGACCCGCTCGTCCCAGGCGGCAACCCCGGCA 310                   330                   350                   370                   390
ACGGCGGGCGGCAGCAACCCGGGCAACGGCGGGCGGCTGCACGGTCCAGAAGTGGGGCCAGTGCGGCGGCATCGGCTACTCGGGCTGCACCACCTG
                                                  Q  K  W  G  Q  C  G  G  I  G  Y  S  G  C  T  T  C 410                   430                   450                   470                   490
CAAGGCCGGCTCGACCTGCCCGCGCCCAGAACGAGTACTACTCGCAGTGCCTGTAAAGGCGGCCGTGGGCTAGGTGGCCGAGCGCGGGGGGTTTCTTCATTGG
 K  A  G  S  T  C  P  A  Q  N  E  Y  Y  S  Q  C  L  *

510                   530                   550                   570                   590
TTGAGCAAATAGAACAGGATTTCCGGCTGCCCGTGGCGGCGCGGCAAGGTAGATAGCCCTTCATTGCTGTAACTAGTATGCTATATACCTCTGCACATT 610                   630                   650                   670                   690
GTCAGTCTGCTTGTACGGAGGCTGGCTGCCCCGTGGCGGCGCGGCAAGGTAGATAGCCCTTCATTGCTGTAACTAGTATGCTATATACCTCTGCACATT 710                   730                   750                   770                   790
TGCAGCCCCATGGTGTGAACAACAAGCTGACAAGGCTTCCAGTTCCAGCCTCGGCAATTGTCACGATATCCTTGGTCCATCTATATGTATGGGCATGAGC 810                   830                   850                   870
GAGTCGAGAAAATGTACCGGAAAAATCGTAGTGACCTGGCCACTGCGCCGTTCTACCACCGTAGGATTGAAGTGAATCTCGAATTC
```

CELLULASES, THE GENES ENCODING THEM AND USES THEREOF

CROSS REFERENCE TO RELATED APPLICATION

This application is a DIV of Ser. No. 08/841,636 filed on Apr. 30, 1997, now matured into a patent U.S. Pat. No. 6,723,549, which is a continuation of International Application No. PCT/FI96/00550, filed Oct. 17, 1996, and a continuation-in-part of U.S. application Ser. No. 08/732,181, filed Oct. 16, 1996 (abandoned), which claims the benefit of U.S. Provisional Application Nos. 60/005,335, filed Oct. 17, 1995; 60/007,926, filed Dec. 4, 1995; and 60/020,840, filed Jun. 28, 1996.

BACKGROUND OF THE INVENTION

1. Field of the Invention

The present invention is related to genes encoding novel neutral cellulases and compositions containing the novel neutral cellulases. These compositions are especially useful in the textile, detergent and pulp and paper industries.

2. Related Art

Cellulose is a linear polysaccharide of glucose residues connected by β-1,4 linkages. In nature, cellulose is usually associated with lignin together with hemicelluloses such as xylans and glucomannans. The practical use of cellulases has been hampered by the nature of the known cellulases, which are often mixtures of cellulases having a variety of activities and substrate specificities. For that reason, it is desirable to identify sources from which cellulases having only the desired activities may be obtained.

A wide variety of cellulases are known in the art, most of which are acid cellulases. However, some neutral and alkaline cellulases have also been identified. Celluzyme® is a commercially-available cellulase preparation from *Humicola insolens* (Novo Nordisk, A/S). GB 2,075,028 and EP 406,314 describe the use of a *Humicola insolens* cellulase as an enzymatic additive in a wash detergent to reduce the harshness (stiffness) of cotton-containing fabrics. The cloning of a cellulase containing endoglucanase activity from *Humicola insolens* is described in WO 93/11249 and EP 531,372. EP 510,091 describes a cellulase from *Bacillus* spp. NCIMB 40250 that is useful in detergent compositions. EP 220,016 describes cellulases that are useful as clarification agents for colored fabrics. WO 94/07998 describes modified cellulases that possess an improved alkaline activity. WO 95/02675 describes detergent compositions that contain two different cellulases: a first cellulase that is catalytically amenable to particulate soil removal, and a second cellulase that is catalytically amenable to color clarification. WO 92/18599 describes a detergent preparation that contains both a cellulase and a protease. Cellulases have also been used industrially as an aid for the removal of printing paste thickener and excess dye after textile printing (EP 576,526).

EP 383 828 describes granular detergent compositions, which contain surface-active agent, a fabric-softening clay material, and cellulase granulates containing calcium carbonate. U.S. Pat. No. 5,433,750 describes detergent compositions containing a surface active agent, a builder system, a softening clay, a clay flocculating agent and a high activity cellulase, preferably *Humicola insolens* cellulase. U.S. Pat. No. 5,520,838 describes granular detergent compositions, comprising surface-active agent, a builder and a cellulase, preferably a *Humicola insolens* cellulase, said compositions being in a compact form, having a relatively high density and containing a low amount of inorganic filler salt.

Cellulase enzymes are used in a wide variety of industries in addition to the textile industry. For example, cellulases are used industrially for the deinking of newspapers and magazines (EP 521,999), for improving the drainage of pulp (WO 91/14822, WO 91/17243), and as a treatment for animal feed.

The unique properties of each cellulase make some more suitable for certain purposes than others. While the enzymes differ in a number of ways, one of the most important difference is pH optimum. Neutral cellulases have useful cellulase activity in the pH range 6-8, alkaline cellulases have useful cellulase activity in the pH range 7.5-10. Acid cellulases are active in the range of pH 4.5-6, but have little cellulase activity at higher pH values.

Neutral and acid cellulases are especially useful in the textile industry Klahorst, S. et al., *Textile Chemist and Colorist* 26:13-18, 1994; Nilsson, T. E., Aachen Textile Conference, *DWI Reports* 114:85-88 (1995); Videbmk, T. et al., *ITB Dyeing/Printing/Finishing*, January 1994, pp. 25-29; Klahorst, S. et al., *AATCC Int. Conf & Exhibit*, Oct. 4-7, 1992, p. 243, Atlanta, Ga.; Kochavi, D. et al., *Am. Dyestuff Resporter*, September 1990, pp. 26-28; Tyndall, R. Michael, *Textile Chemist and Colorist* 24:23 (1992); Lange, N. K., in *Proc. Second TRICEL Symp. on Trichoderma reesei Cellulases and Other Hydrolases*, Espoo, Finland, 1993, ed. P. Suominen et al., Foundation for Biotechnical and Industrial Fermentation Research vol. 8, 1993, pp. 263-272. When used to treat fabric, cellulases attack the chains of cellulose molecules that form the cotton fibers, thereby affecting the characteristics of the fabric.

Traditionally, in "stonewashing," pumice stones have been used to change the characteristics of the fabric. Gradually, cellulases are replacing pumice stones, which also give the fabric its desired final look but can cause damage to the machines, garments and sewage processing equipment. U.S. Pat. Nos. 4,832,864, 4,912,056, 5,006,126, 5,122,159, 5,213,581 and EP 307,564 disclose the use of cellulases in biostoning.

Cellulases are especially useful for stonewashing denim dyed with indigo as the dye mostly stays on the surface of the yarn and does not penetrate the fibers well. When used to treat cotton fabric, neutral cellulases generally require a longer wash time than do the acid cellulases. However, available neutral cellulases are less aggressive (active) against cotton than acid cellulases, and are reported not to compromise the strength of the fabric as readily as acid cellulases. Neutral cellulases have a broader pH profile and thus the pH increase that occurs during biostoning has little effect on the activity of the neutral enzyme.

The use of acid cellulases is hampered by their tendency to promote backstaining and a weakening of fabrics. In addition, the pH must be adjusted to to a range suitable for the function of the acid cellulases. Consequently, there is a clear demand for neutral cellulase enzyme preparations that do not cause backstaining or weakening of fabrics.

While it has become popular to use cellulases in the textile industry, simply changing the cellulase mixture that is used may produce a different finish. These problems have focused increasing attention on the search for reproducible mixtures of cellulases with desired properties. Thus there is a clear demand especially in the textile and detergent industry for novel cellulases active at neutral and alkaline pH values, not compromising the strength of fabrics, with good cleaning and/or fabric care and harshness reducing properties.

SUMMARY OF THE INVENTION

Recognizing the importance of identifying enzymes useful in textile biofinishing and biostoning and in detergent applications, the inventors have screened fungal species for neutral and alkaline cellulases with enzymatic characteristics that would be useful in such technologies.

These studies have resulted in novel cellulases originating from the genera *Myceliophthora, Myriococcum, Melanocarpus, Sporotrichum* and *Chaetomium*.

The invention is further directed to the spent culture medium or enzyme preparations prepared from the native hosts producing such novel cellulases.

The invention is further directed to the use of such culture medium or the use of such enzyme preparations in the textile and detergent industry and in the pulp and paper industries.

These studies have further resulted in the identification of three novel cellulases that are especially useful in the textile and detergent industry. Purified preparations from *Melanocarpus* sp. or *Myriococcum* sp. have revealed a 20 kDa cellulase with endoglucanase activity (designated herein as "20K-cellulase"), a 50 kDa cellulase ("50K-cellulase"), and a second 50 kDa cellulase ("50K-cellulase B"). A novel gene product with high homology to the cellulase family, herein called "protein-with-CBD" (where CBD means "cellulose binding domain") was also discovered.

It is an object of the invention to provide enzyme preparations that contain one or more of the novel cellulases of the invention, especially the 20K-cellulase, the 50K-cellulase, the 50K-cellulase B and/or the protein-with-CBD.

It is a further object of this invention to provide a method for using such preparations for the finishing of textiles, especially the biostoning of denim, for the use said preparations in detergent compositions, and especially methods that use the 20K-cellulase, the 50K-cellulase, the 50K-cellulase B and/or the protein-with-CBD.

The invention is also directed to other neutral and/or alkaline cellulases having one or more of the amino acid sequences as described herein.

The invention is further directed to the genes encoding the 20K-cellulase, 50K-cellulase, 50K-cellulase B and the protein-with-CBD.

The invention is further directed to novel expression vectors comprising such genes and to novel hosts transformed with the vectors, especially hosts that are capable of high levels of expression of the proteins encoded by such genes.

The invention is further directed to the spent culture medium of such transformed hosts, the culture medium containing the novel 20K-cellulase, 50K-cellulase, the 50K-cellulase B and/or the protein-with-CBD, or enzyme compositions (enzyme preparations) containing one or more of these proteins that have been prepared from such culture media.

The invention is further directed to the use of such culture medium or the use of such enzyme preparations in the textile and detergent industry and in the pulp and paper industries.

A Partially crystalline material precipitated from the active S-Sepharose™ fractions (lane 1).

B Fractions from chromatography of the partially crystalline material on G50 Sephadex. Fractions shown in lanes 19 and 25 contained no endoglucanase activity. For the other fractions, the amounts of activity (in ECU) applied to the gel was as follows: fraction 27, 0.4; 29, 2.4 (as 3.0 µg of protein); 30, 2.1; 31, 1.9; 33, 0.46; and 35, 1.1.

Figure 10:
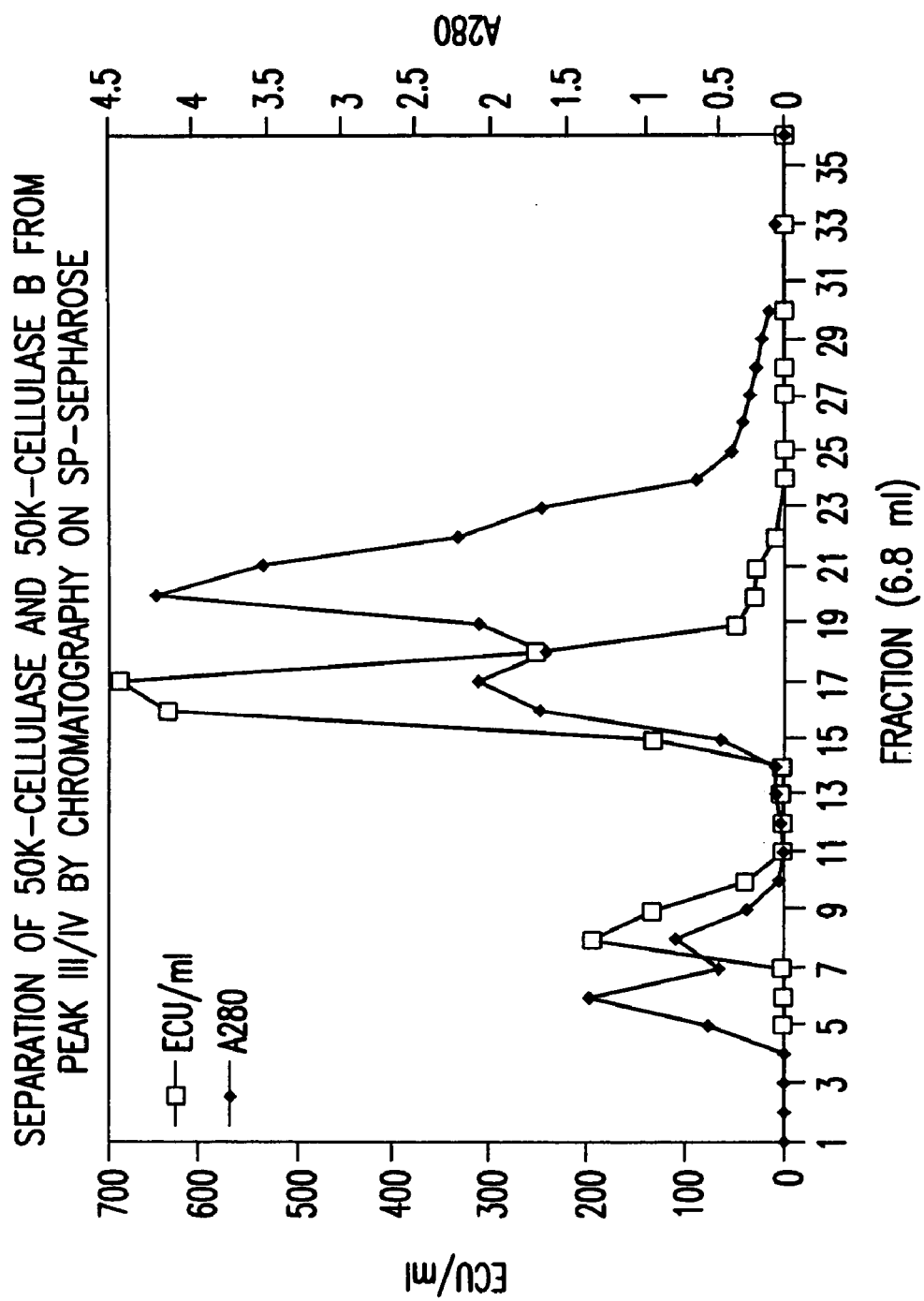

FIG. 10 shows the separation of 50K-cellulase and 50K-cellulase B from Peak III/IV by chromatography on SP-Sepharoser™. A sample containing 200 mg of protein and 14,800 ECU was applied to the 2.5×11 cm column, which was developed as described in Example 9. Fractions of 6.8 ml were collected. A minor amount of 50K-cellulase eluted before the NaCl gradient, whereas most of the 50K-cellulase eluted at about 50 mM NaCl. 50K-cellulase B was found in the major protein peak at about 80 mM NaCl.

Figures 11A, 11B:
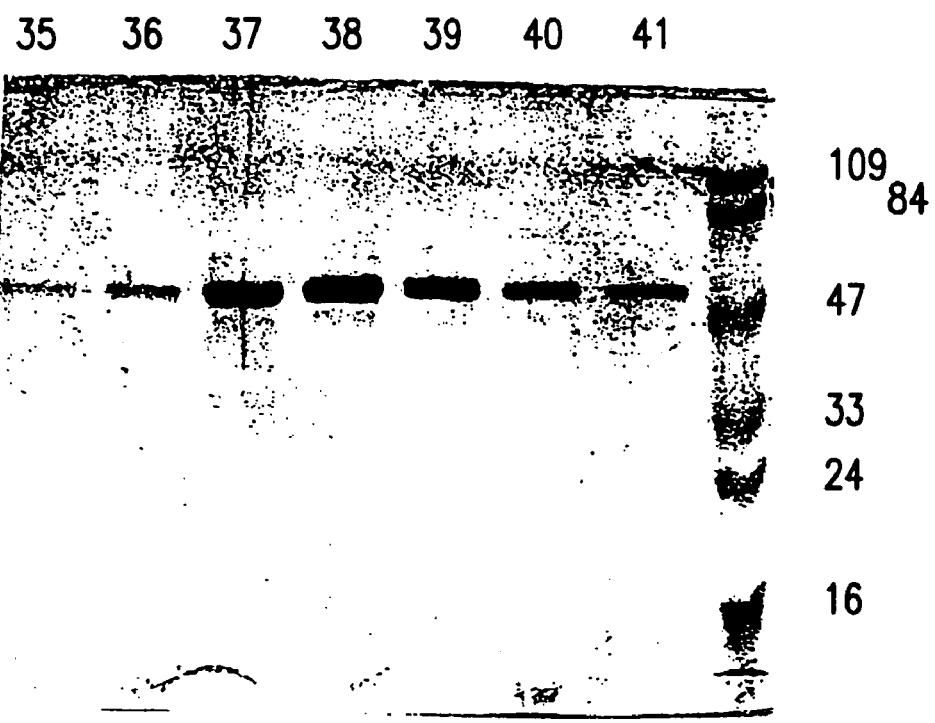

FIG. 11 shows an SDS-PAGE analysis of purified 50K-cellulase (11A) and 50K-cellulase B (11B). Lane numbers indicate the fractions (3.3 ml) eluted from Phenyl-Sepharose. For fractions 36-41, 2.5 μl of each fraction was applied to the gel. For the other fractions, 2 μl was applied. The 50K-cellulase peak was found in fractions 37-38 (11A) (containing 780 and 880 ECU/ml, respectively). The 50K-cellulase B peak was in fractions 30 and 31 (11B), which contained negligible activity (less than 4 ECU/ml).

Figure 12:
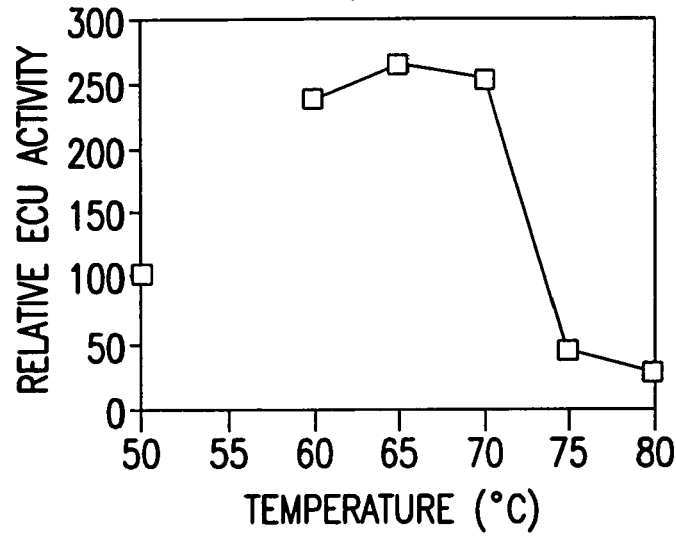

FIG. 12 shows the temperature dependence of the endoglucanase activity of 50K-cellulase at pH 7.0 and a reaction time of 60 min.

Figure 13:
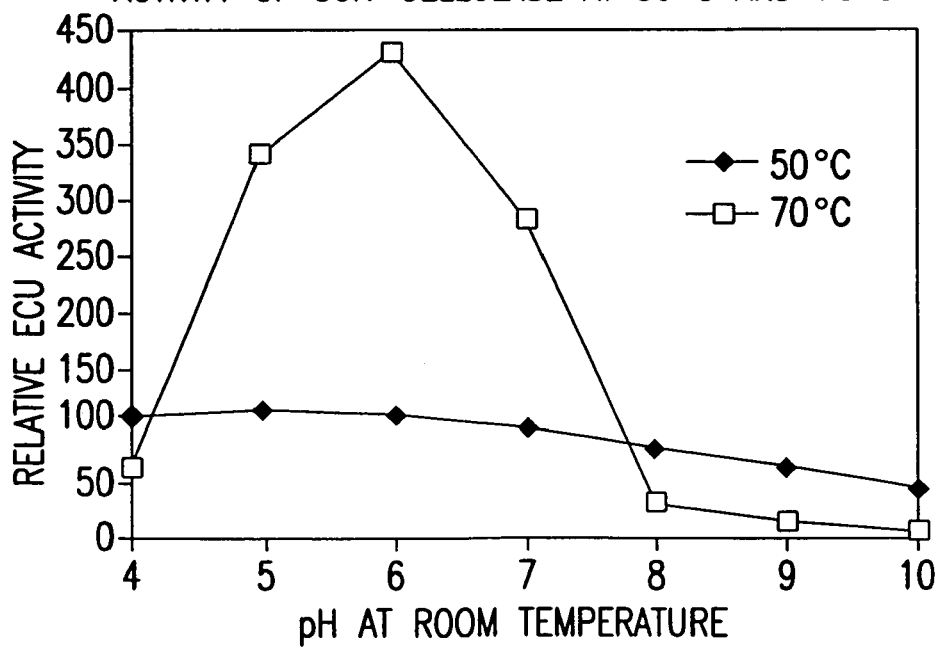

FIG. 13 shows the pH dependence of the endoglucanase activity of 50K-cellulase at 50° C. (♦) and 70° C. (□).

Figure 14:
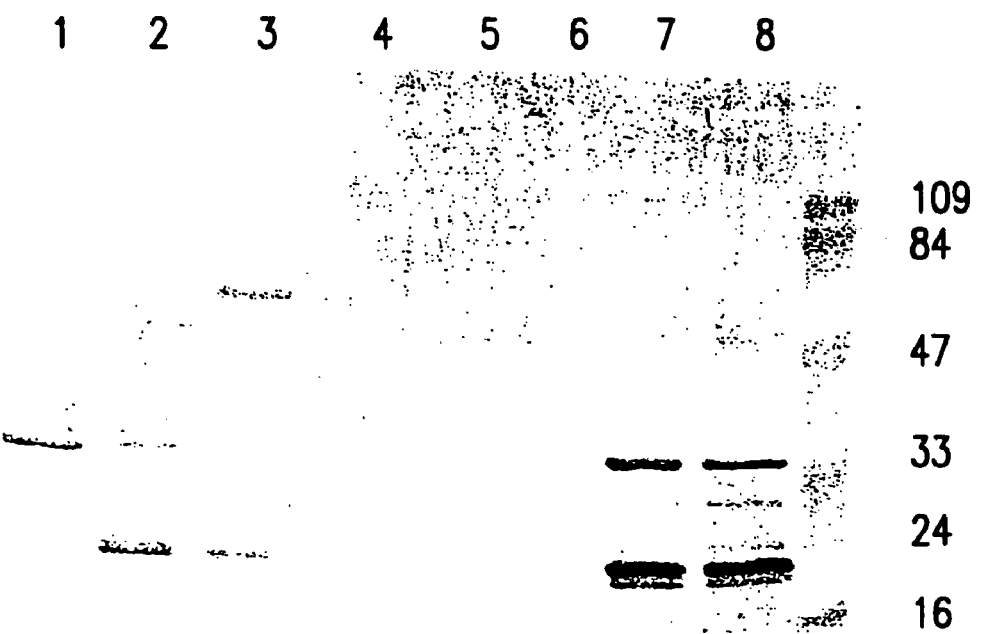

FIG. 14 shows a Western analysis using 20K-cellulase antiserum as a probe. Lanes 1, 2 and 3 contain 25 μg of protein from the DEAE-Sepharose peaks I, III and IV, respectively. Lanes 4 and 5 contain 2.0 and 0.2 μg of pure 50K-cellulase and lane 6 contains 0.6 μg of pure 50K-cellulase B. Lanes 7 and 8 contain about 25 μg protein from the whole growth medium of ALKO4237 and ALKO4124, respectively.

Figure 15:
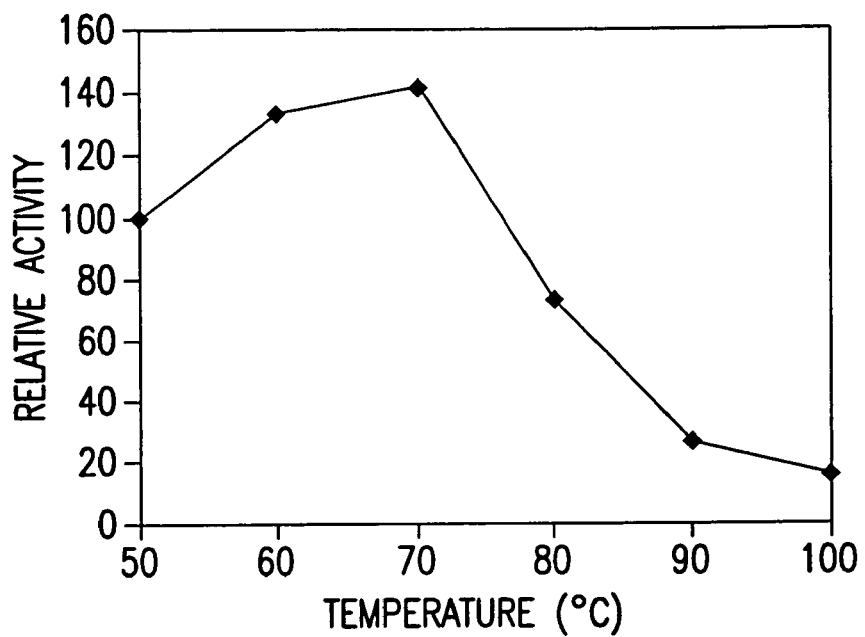

FIG. 15 shows the temperature dependence of the endoglucanase activity of 20K-cellulase at pH 7 (10 min reaction times).

FIGS. 16 (A and B) show the pH-dependence of the endoglucanase activity of the 20K-cellulase for the reaction time of (a) 10 minutes or (b) 60 minutes.

FIG. 17 shows amino acid sequence data derived from sequencing the 20K-cellulase described in the exemplary material herein. Sequence 429 (SEQ ID NO:1) is from the N terminus of the protein and the other sequences are from internal tryptic peptides. Sequence #430 corresponds to SEQ ID NO: 2; sequence #431 corresponds to SEQ ID NO: 3; sequence #432 corresponds to SEQ ID NO: 4; sequence #433 corresponds to SEQ ID NO: 5; sequence #439 corresponds to SEQ ID NO: 6; fr 9 corresponds to SEQ ID NO: 7; fr 14 corresponds to SEQ ID NO: 8; fr 16 corresponds to SEQ ID NO: 9; ft 17 corresponds to SEQ ID NO: 10; fr 28 corresponds to SEQ ID NO: 11 and fr 30 corresponds to SEQ ID NO: 12.

Figure 18:
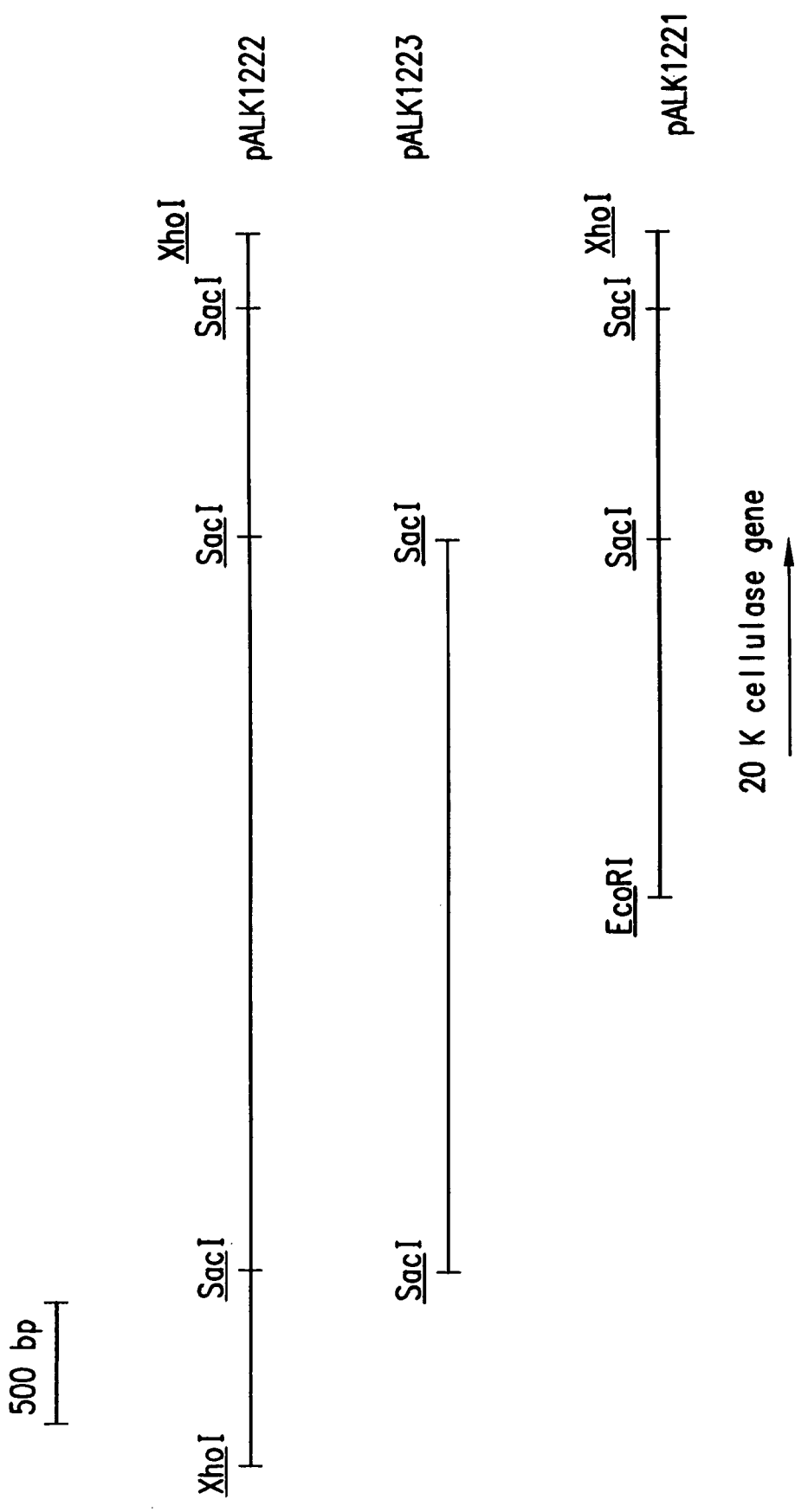

FIG. 18 shows the restriction maps of the *Melanocarpus albomyces* DNA in plasmids pALK1221, pALK1222 and pALK1223, which carry the 20K-cellulase gene.

FIGS. 19 (A and B) shows the DNA sequence of the 20K-cellulase gene (SEQ ID No: 30 ). The arrow indicates the predicted signal peptidase processing site.

Figure 20:
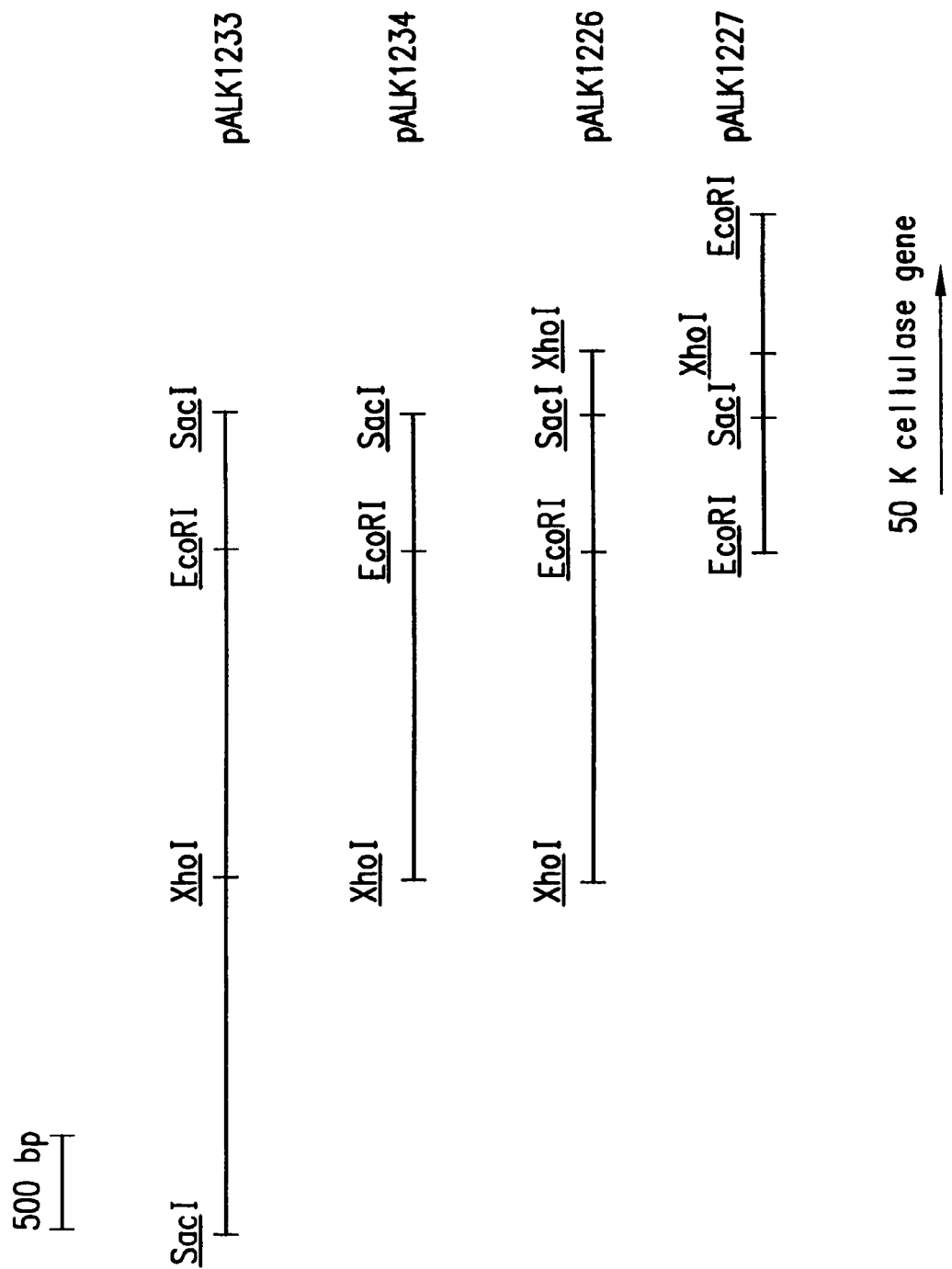

FIG. 20 shows the restriction maps of the *Melanocarpus albomyces* DNA in plasmids pALK1233, pALK1234, pALK1226 and pALK1227, which carry the 50K-cellulase gene.

FIGS. 21 (A, B and C) show the DNA sequence of the 50K-cellulase gene (SEQ ID NO: 32). The arrow indicates the predicted signal peptidase processing site.

Figure 22:
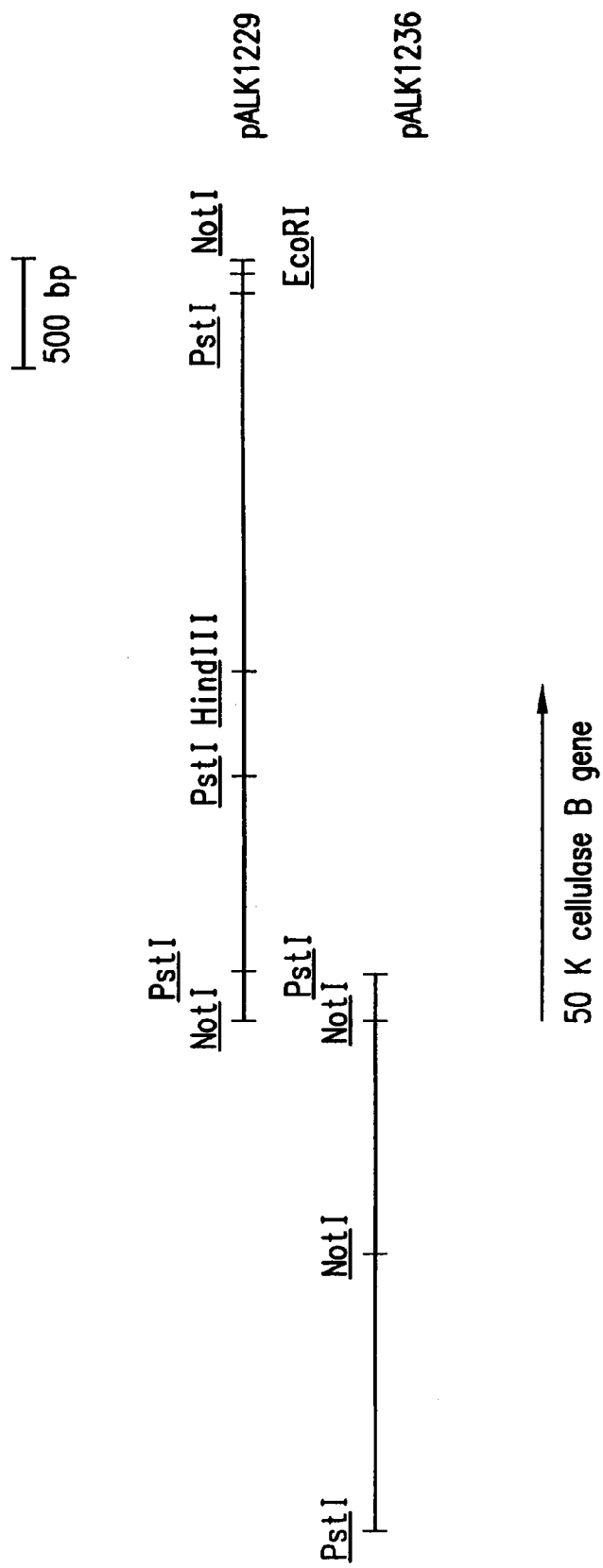

FIG. 22 shows the restriction maps of the *Melanocarpus albomyces* DNA in plasmids pALK1229 and pALK1236, which carry the 50K-cellulase B gene.

FIGS. 23 (A, B and C) show the DNA sequence of the 50K-cellulase B gene (SEQ ID NO: 34). The arrow indicates the predicted signal peptidase processing site.

Figure 24:
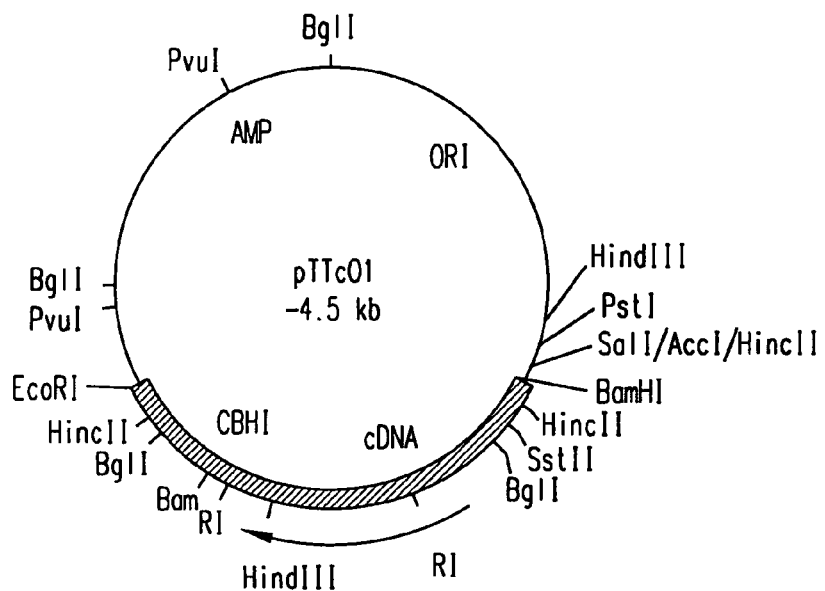

FIG. 24 shows the plasmid map of pTTc01.

Figure 25:
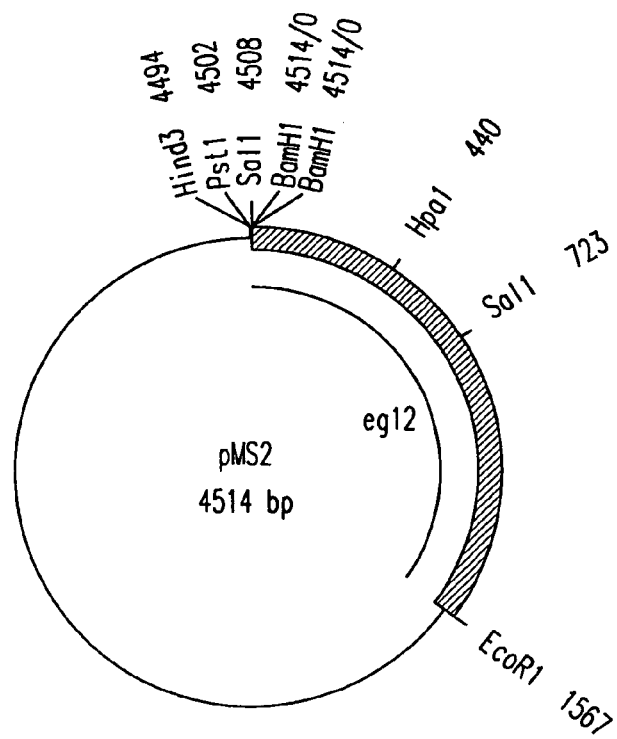

FIG. 25 shows the plasmid map of pMS2.

Figure 26:
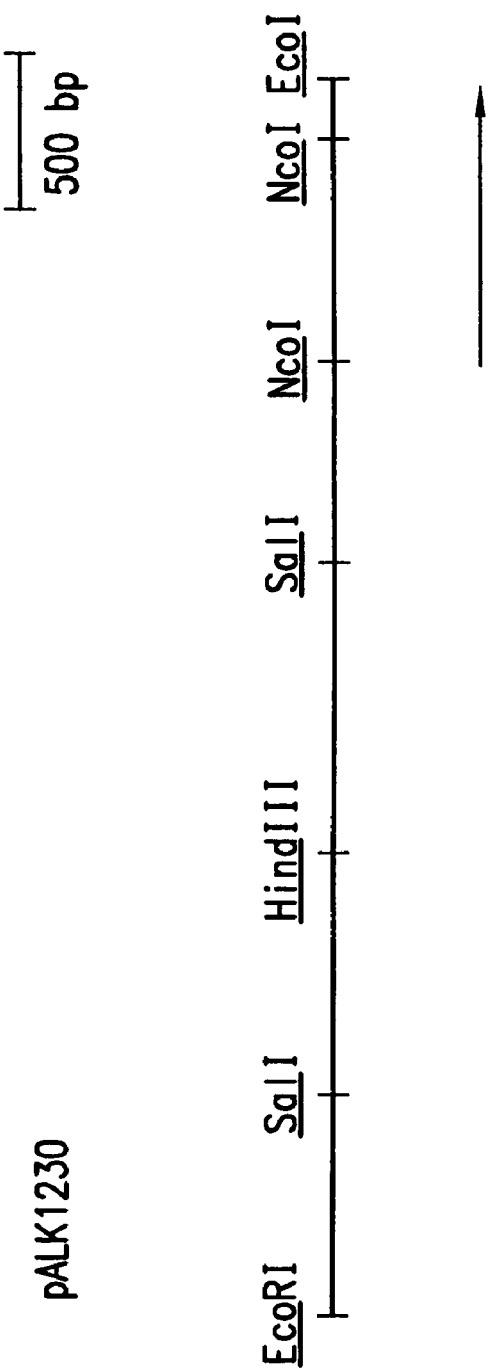

FIG. 26 shows the restriction map of the *Melanocarpus albomyces* DNA in plasmid pALK1230, which carries DNA encoding the protein-with-CBD. The sequence presented in FIG. 27 is marked with an arrow in FIG. 26.

FIG. 27 shows the DNA sequence of the the protein-with-CBD cellulase gene (SEQ ID NO: 36) in pALK1230.

Figure 28:
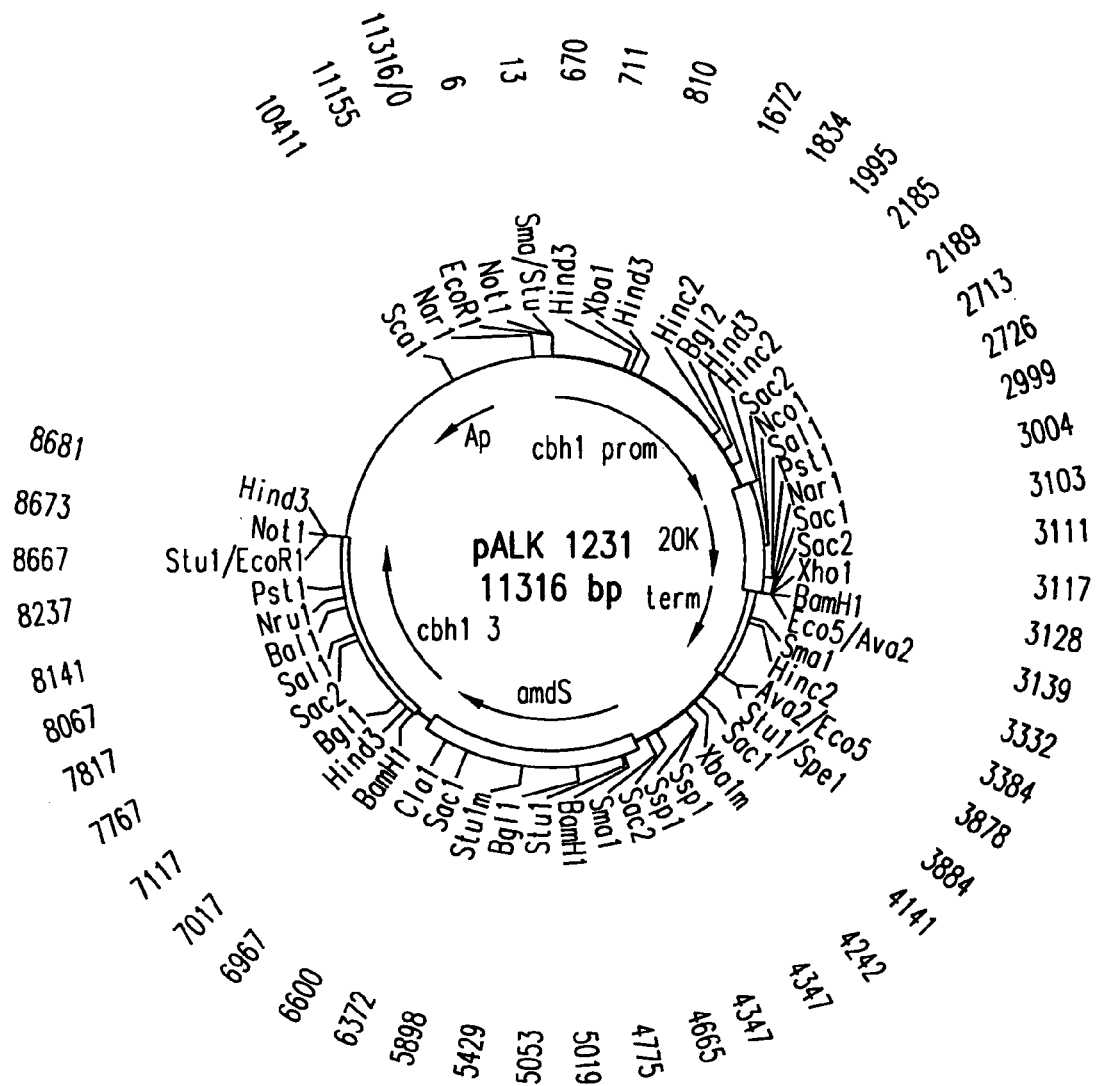

FIG. 28 shows the plasmid map of pALK1231.

Figure 29:
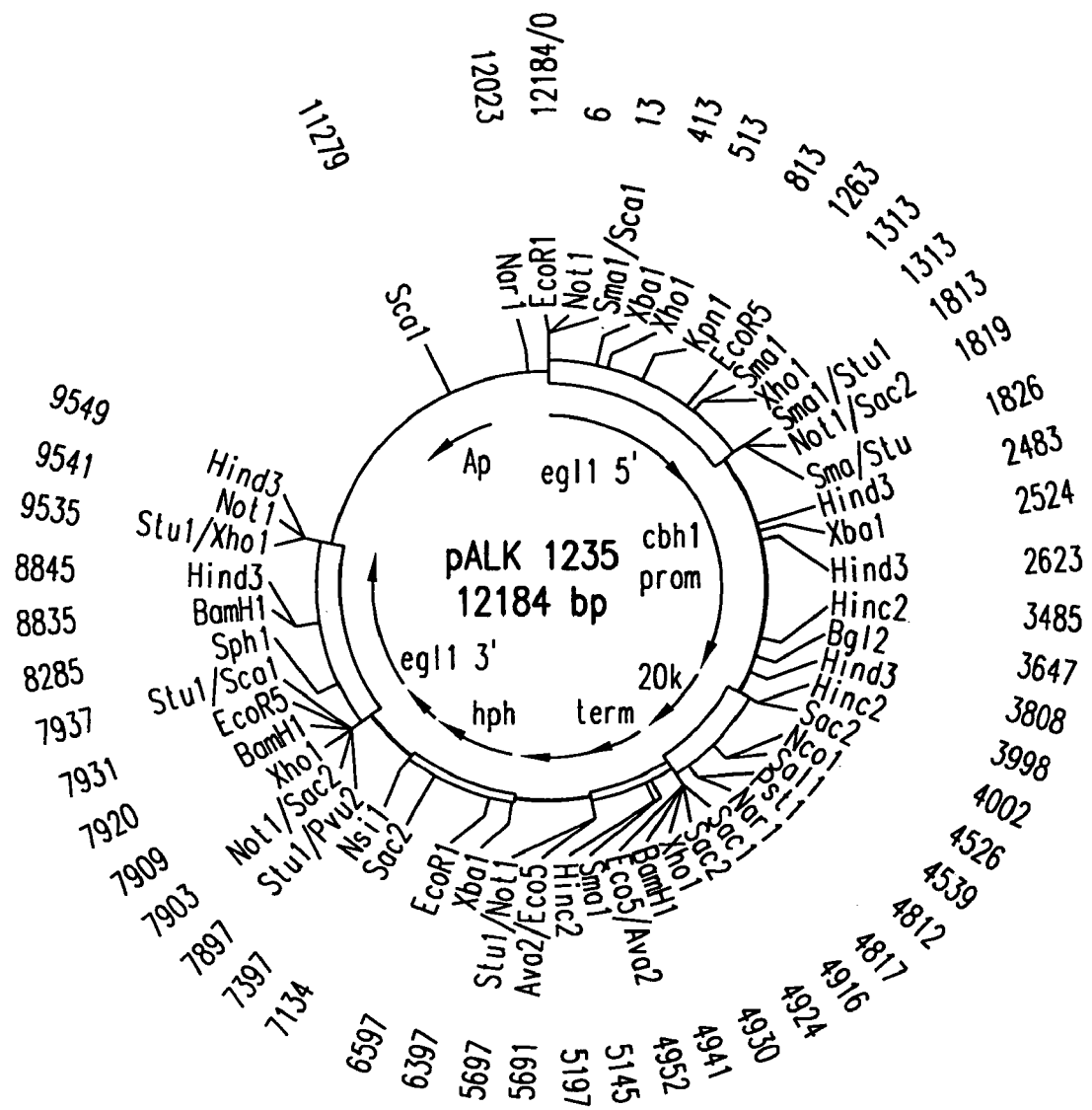

FIG. 29 shows the plasmid map of pALK1235.

Figure 30:
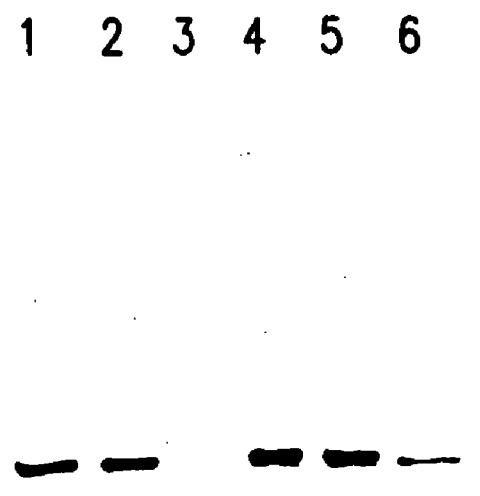

FIG. 30 shows a Western analysis using 20K-cellulase antiserum as a probe. Lanes 1 and 2 contain about 10 μg protein from the whole growth medium of transformants ALKO3620/pALK1235/49 and ALKO3620/pALK1235/40. Lane 3 contains about 10 μg protein from the whole growth medium of ALKO3620. Lanes 4 and 5 contain about 10 μg protein from the whole growth medium of transformants ALKO3620/pALK1231/16 and ALKO3620/pALK1231/14. Lane 6 contains 100 ng of pure 20K-cellulase.

Figure 31:
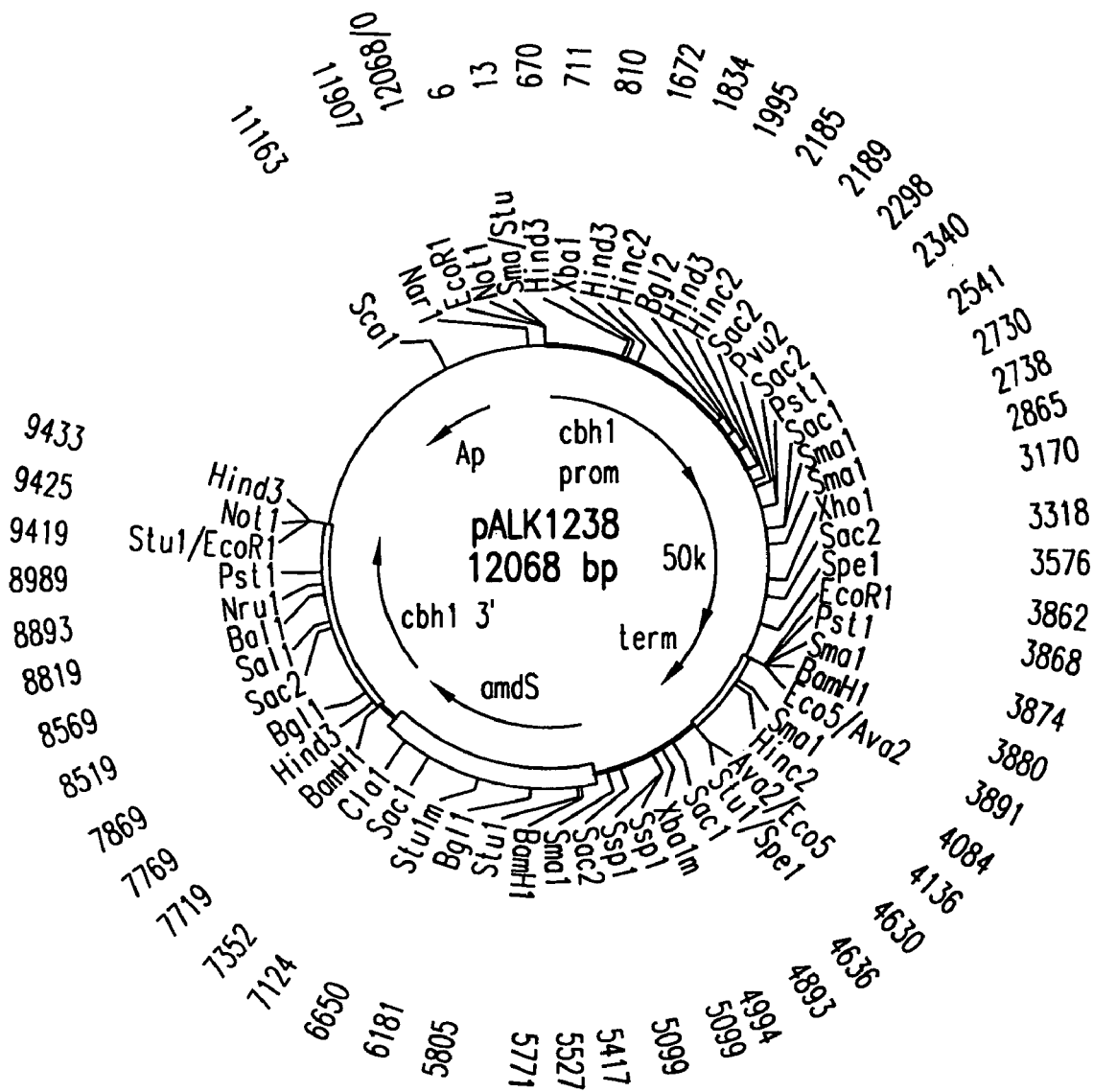

FIG. 31 shows the plasmid map of pALK1238.

Figure 32:
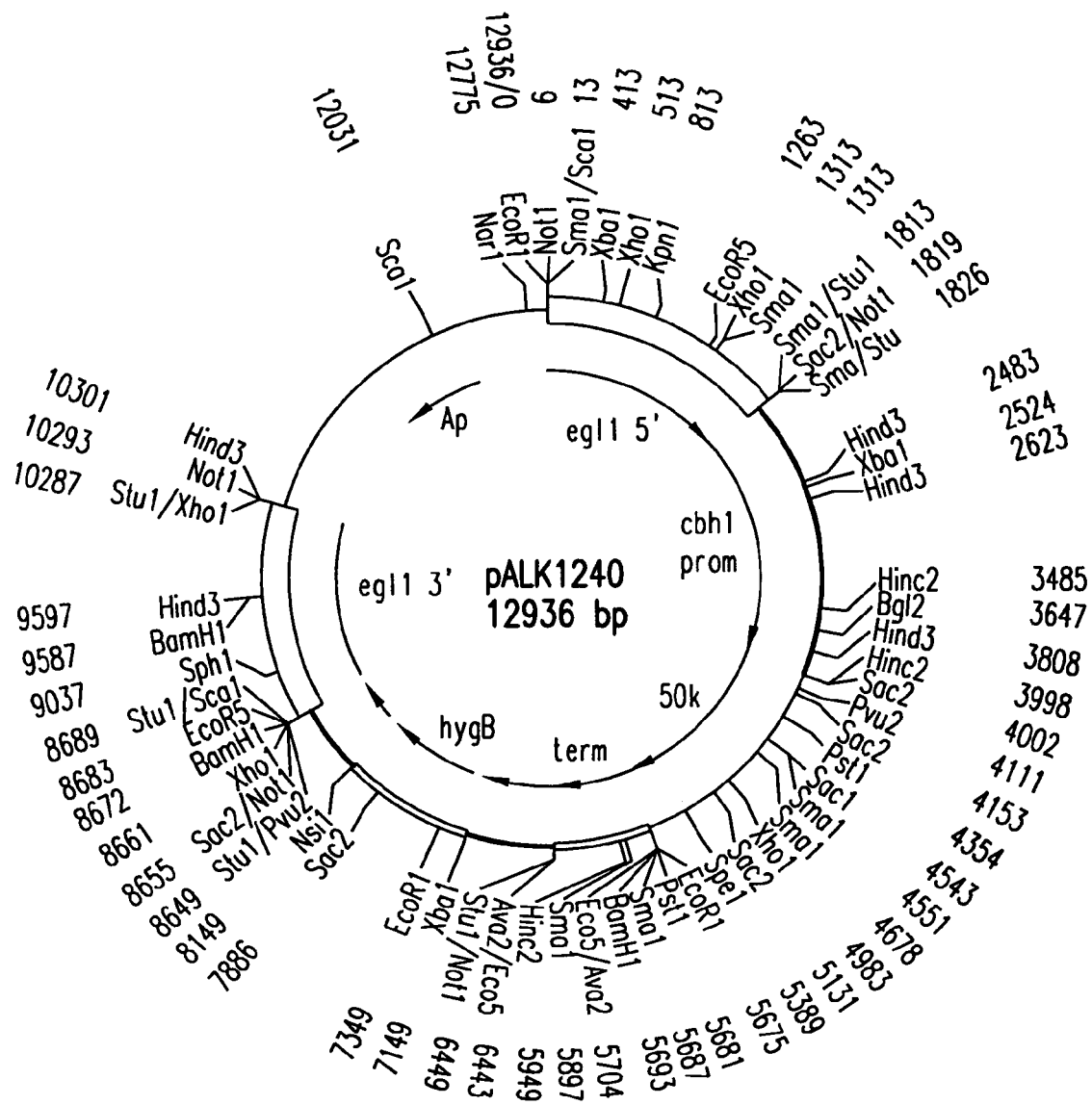

FIG. 32 shows the plasmid map of pALK1240.

DEPOSITS

ALKO4179, *Myceliophthora thermophila* was deposited as CBS 689.95 on Oct. 12, 1995, at the Centraalbureau voor Schimmelcultures, P.O. Box 273, 3740 AG BAARN.

ALKO4124, *Myriococcum* sp. was deposited as CBS 687.95 on Oct. 12, 1995, at the Centraalbureau voor Schimmelcultures, P.O. Box 273, 3740 AG BAARN.

ALKO4237, *Melanocarpus albomyces* (=*Myriococcum albomyces*=*Thielavia albomyces*; Guarro et al., 1996, *Mycol. Res.* 100(1):75.) was deposited as CBS 685.95 on Oct. 11, 1995, at the Centraalbureau voor Schimmelcultures, P.O. Box 273, 3740 AG BAARN.

ALKO4125, *Sporotrichum thermophile* was deposited as CBS 688.95 on Oct. 12, 1995, at the Centraalbureau voor Schimmelcultures, P.O. Box 273, 3740 AG BAARN.

ALKO4265, *Chaetomium thermophilum* La Touche was deposited as CBS 730.95 on Nov. 8, 1995, at the Centraalbureau voor Schimmelcultures, P.O. Box 273, 3740 AG BAARN.

Plasmid pALK1221 was deposited as DSM 11024 on Jun. 21, 1996 and λ4237/5.1 was deposited as DSM 11012 on Jun. 21, 1996, at the Deutsche Sammlung von Mikroorganismen und Zellkulturen GmbH, Mascheroder Weg 1B, D-38124 Braunschweig, Germany. Both contain the 20K-cellulase gene from *Melanocarpus albomyces* CBS 685.95.

Plasmid pALK1227 was deposited as DSM 11025 on Jun. 21, 1996 and λ4237/35 was deposited as DSM 11014 on Jun. 21, 1996, at the Deutsche Sammlung von Mikroorganismen und Zellkulturen GmbH, Mascheroder Weg 1B, D-38124 Braunschweig, Germany. Both contain the 50K-cellulase gene from *Melanocarpus albomyces* CBS 685.95.

Plasmid pALK1229 was deposited as DSM 11026 on Jun. 21, 1996 and λ4237/3 was deposited as DSM 11011 on Jun. 21, 1996, and λ4237/18 was deposited as DSM 11013 on Jun. 21, 1996, at the Deutsche Sammlung von Mikroorganismen und Zellkulturen GmbH, Mascheroder Weg 1B, D-38124 Braunschweig, Germany. pALK1229 contains DNA coding for the 50K-cellulase B, λ4237/3 and λ4237/18 contain the 50K-cellulase B gene from *Melanocarpus albomyces* CBS 685.95.

Plasmid pALK1230 was deposited as DSM 11027 on Jun. 21, 1996 at the Deutsche Sammlung von Mikroorganismen und Zellkulturen GmbH, Mascheroder Weg 1B, D-38124 Braunschweig, Germany. pALK1230 contains the protein-with-CBD gene from *Melanocarpus albomyces* CBS 685.95.

DETAILED DESCRIPTION OF THE PREFERRED EMBODIMENTS

In the description that follows, a number of terms used in textile industry technology are extensively utilized. In order to provide a clear and consistent understanding of the specification and claims, including the scope to be given such terms, the following definitions are provided.

Biostoning. "Biostoning" of fabric or garment means the use of enzymes in place of, or in addition to, the use of pumice stones for the treatment of fabric or garment, especially denim.

Biofinishing. "Biofinishing" refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colours, improves the drapability of the fabric, improves moisture absorbability and which may improve also the dyeability.

Backstaining. Released dye has a tendency to redeposit on the surface of the fabric fibers. This effect is termed "backstaining."

Detergent. By "detergent" is meant a cleansing agent that can contain surface active agents (anionic, non-ionic, cationic and ampholytic surfactants), builders and other optional ingredients such as antiredeposition and soil suspension agents, optical brighteners, bleaching agents, dyes and pigments and hydrolases. Suitable listing of the contents of detergents is given in U.S. Pat. No. 5,433,750, a suitable list of surfactants is given in U.S. Pat. No. 3,664,961.

Enzyme preparation. By "enzyme preparation" is meant a composition containing enzymes. Preferably, the enzymes have been extracted from (either partially or completely purified from) a microbe or the medium used to grow such microbe. "Extracted from" means that the desired enzymes are separated from the cellular mass. This can be performed by any method that achieves this goal, including breaking cells and also simply removing the culture medium from spent cells. Therefore, the term "enzyme preparation" includes compositions containing medium previously used to culture a desired microbe(s) and any enzymes that have been released from the microbial cells into such medium during the culture or downstream processing steps.

By a host that is "substantially incapable" of synthesizing one or more enzymes is meant a host in which the activity of one or more of the listed enzymes is depressed, deficient, or absent when compared to the wild-type.

By an amino acid sequence that is an "equivalent" of a specific amino acid sequence is meant an amino acid sequence that is not identical to the specific amino acid sequence, but rather contains at least some amino acid changes (deletions, substitutions, inversions, insertions, etc) that do not essentially affect the biological activity of the protein as compared to a similar activity of the specific amino acid sequence, when used for a desired purpose. The biological activity of a cellulase, is its catalytic activity, and/or its ability to bind to cellulosic material. The biological activity of the 50K-cellulase B further includes its ability to act synergistically with the cellulases. Preferably, an "equivalent" amino acid sequence contains at least 80%-99% identity at the amino acid level to the specific amino acid sequence, most preferably at least 90% and in an especially highly preferable embodiment, at least 95% identify, at the amino acid level.

Cloning vehicle. A cloning vehicle is a plasmid or phage DNA or other DNA sequence (such as a linear DNA) that provides an appropriate nucleic acid carrier environment for the transfer of a gene of interest into a host cell. The cloning vehicles of the invention may be designed to replicate autonomously in prokaryotic and eukaryotic hosts. In fungal hosts such as *Trichoderma*, the cloning vehicles generally do not autonomously replicate and instead, merely provide a vehicle for the transport of the gene of interest into the *Trichoderma* host for subsequent insertion into the *Trichoderma* genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Markers, for example, are antibiotic resistance. Alternatively, such markers may be provided on a cloning vehicle which is separate from that supplying the gene of interest. The word "vector" is sometimes used for "cloning vehicle."

Expression vehicle. An expression vehicle is a cloning vehicle or vector similar to a cloning vehicle but which is capable of expressing a gene of interest, after transformation into a desired host. When a fungal host is used, the gene of interest is preferably provided to a fungal host as part of a cloning or expression vehicle that integrates into the fungal chromosome, or allows the gene of interest to integrate into the host chromosome. Sequences that are part of the cloning vehicle or expression vehicle may also be integrated with the gene of interest during the integration process. In *T. reesei*, sites of integration to which the gene of interest can be directed include the cbh and/or the egl loci. Most preferably, the gene of interest is directed to replace one or more genes encoding undesirable characteristics.

The gene of interest is also preferably placed under the control of (i.e., operably linked to) certain control sequences such as promoter sequences provided by the vector (which integrate with the gene of interest). Alternatively, the control sequences can be those at the insertion site.

The expression control sequences of an expression vector will vary depending on whether the vector is designed to express a certain gene in a prokaryotic or in a eukaryotic host (for example, a shuttle vector may provide a gene for selection in bacterial hosts). Expression control sequences can contain transcriptional regulatory elements such as, promoters, enhancer elements, and transcriptional termination sequences, and/or translational regulatory elements, such as, for example, translational initiation and termination sites.

According to the invention, there are provided neutral and alkaline cellulases, and methods for producing such useful neutral and alkaline cellulases, that are desirable for the treatment of textile materials.

The native hosts that produce the proteins of the invention are:

1) ALKO4179, *Myceliophthora thermophila*; deposited as CBS 689.95 at the Centraalbureau voor Schimmelcultures, P.O. Box 273, 3740 AG BAARN.

2) ALKO4124, *Myriococcum* sp.; deposited as CBS 687.95;

3) ALKO4237, *Melanocarpus albomyces*, deposited as CBS 685.95;

4) ALKO4125, *Sporotrichum thermophila*, deposited as CBS 688.95; and

5) ALKO4265, *Chaetomium thermophilum* La Touche, deposited as CBS 730.95

One specific preferred embodiment of the invention is the spent culture medium of the native hosts or enzyme preparations prepared from the culture medium.

In specific preferred embodiments of the invention, the purified 20K-cellulase, 50K-cellulase, 50K-cellulase B and/or protein-with-CBD is provided. These proteins can be obtained for example from *Melanocarpus* sp. or *Myriococcum* sp. as described herein, and especially in Example 9.

Amino acid sequence data have been generated from the cellulases described herein. Accordingly, the invention is also directed to neutral or alkaline cellulases containing one or more of the amino acid sequences shown herein. Thus, the invention is intended to be directed to any neutral or alkaline cellulase that is a functional equivalent of the 20K-cellulase, the 50K-cellulase, the 50K-cellulase B and/or protein-with-CBD and having one or more of the amino acid sequences described herein, or substantially the same sequence. Such neutral or alkaline cellulases can be derived from other strains of the same species or from divergent organisms.

In further preferred embodiments, the 20K-cellulase is provided with the material from separate peaks formed during the exemplified purification procedures (e.g., DEAE-Sepharose Pools I, III, or IV in Table VIII herein). In still further embodiments, other proteins in the *Melanocarpus albomyces* ALKO 4237 medium may be used, either alone or in combination with other such proteins.

In further preferred embodiments, the 50K-cellulase is provided with the material from separate peaks formed during the exemplified purification procedures. In still further embodiments, other proteins in the ALKO 4237 medium may be used, either Alone or in combination with other such proteins.

In further preferred embodiments, the 50K-cellulase B is provided with the material from separate peaks formed during the exemplified purification procedures. In still further embodiments, other proteins in the ALKO 4237 medium may be used, either alone or in combination with other such proteins.

As described herein, ALKO 4265, *Chaetomium thermophilum* La Touche, deposited as CBS 730.95, is used herein as an example of a neutral cellulase that is not preferred in biostoning method of the invention because it causes back-staining. However, there is evidence that it is useful in other applications (e.g. in detergents).

The process for genetically engineering the hosts of the invention is facilitated through the cloning of genetic, sequences that encode the desired protein and through the expression of such genetic sequences. As used herein the term "genetic sequences" is intended to refer to a nucleic acid molecule (preferably DNA). Genetic sequences that encode the desired protein are derived from a variety of sources. These sources include genomic DNA, cDNA, synthetic DNA and combinations thereof. Vector systems may be used to produce hosts for the production of the enzyme preparations of the invention. Such vector construction (a) may further provide a separate vector construction (b) which encodes at least one desired gene to be integrated to the genome of the host and (c) a selectable marker coupled to (a) or (b). Alternatively, a separate vector may be used for the marker.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two DNA sequences does not (1) result in the introduction of a frame-shift mutation, (2) interfere with the ability of the expression regulatory sequences to direct the expression of the mRNA, antisense RNA, or protein, or (3) interfere with the ability of the template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively. Expression of the protein in the transformed hosts requires the use of regulatory regions functional in such hosts. A wide variety of transcriptional and translational regulatory sequences can be employed. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

As is widely known, translation of eukaryotic mRNA is initiated at the codon which encodes the first methionine. For this reason, it is preferable to ensure that the linkage between a eukaryotic promoter and a DNA sequence which encodes the protein, or a functional derivative thereof, does not contain any intervening codons which are capable of encoding a methionine. The presence of such codons results either in a formation of a fusion protein (if the AUG codon is in the same reading frame as the protein encoding DNA sequence) or a frame-shift mutation (if the AUG codon is not in the same reading frame as the protein encoding sequence).

In a preferred embodiment, a desired protein is secreted into the surrounding medium due to the presence of a secretion signal sequence. If a desired protein does not possess its own signal sequence, or if such signal sequence does not function well in the host, then the protein's coding sequence may be operably linked to a signal sequence homologous or heterologous to the host. The desired coding sequence may be linked to any signal sequence which will allow secretion of the protein from the host. Such signal sequences may be designed with or without specific protease sites such that the signal peptide sequence is amenable to subsequent removal. Alternatively, a host that leaks the protein into the medium may be used, for example a host with a mutation in its membrane.

If desired, the non-transcribed and/or non-translated regions 3' to the sequence coding for a protein can be obtained by the above-described cloning methods. The 3'-non-transcribed region may be retained for its transcriptional termination regulatory sequence elements; the 3-non-translated region may be retained for its translational termination regulatory sequence elements, or for those elements which direct polyadenylation in eukaryotic cells.

The vectors of the invention may further comprise other operably linked regulatory elements such as enhancer sequences.

In a preferred embodiment, genetically stable transformants are constructed whereby a desired protein's DNA is integrated into the host chromosome. The coding sequence for the desired protein may be from any source. Such integration may occur de novo within the cell or, in a most preferred embodiment, be assisted by transformation with a vector which functionally inserts itself into the host chromosome, for example, DNA elements which promote integration of DNA sequences in chromosomes.

Cells that have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transformation.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) is prepared for expression, the DNA construct(s) is introduced into an appropriate host cell by any of a variety of suitable means, including transformation as described above. After the introduction of the vector, recipient cells are grown in a selective medium, which selects for the growth of transformed cells. Expression of the cloned gene sequence(s) results in the production of the desired protein, or in the production of a fragment of this protein. This expression can take place in a continuous manner in the transformed cells, or in a controlled manner.

Accordingly, the protein encoding sequences described herein may be operably linked to any desired vector and transformed into a selected host, so as to provide for expression of such proteins in that host.

The subject matter of the invention are also nucleic acid molecules coding for proteins having the biological activity of a cellulase and that hybridize to any of the nucleic acid molecules described above or which are defined in the following:

A nucleic acid molecule encoding a polypeptide having the enzymatic activity of a cellulase, selected from the group consisting of:

(a) nucleic acid molecules encoding a polypeptide comprising the amino acid sequence as depicted in FIG. 19 (SEQ ID NO: 31) or 21 (SEQ ID NO: 33);

(b) nucleic acid molecules encoding a polypeptide comprising the amino acid sequence as depicted in FIG. 23 (SEQ ID NO: 35) or 27 (SEQ ID NO: 37);

(c) nucleic acid molecules comprising the coding sequence of the nucleotide sequence as depicted in FIG. 19 (SEQ ID NO: 30) or 21 (SEQ ID NO: 32);

(d) nucleic acid molecules comprising the coding sequence of the nucleotide sequence as depicted in FIG. 23 (SEQ ID NO: 34) or 27 (SEQ ID NO: 36);

(e) nucleic acid molecules encoding a polypeptide comprising the amino acid sequence encoded by the DNA insert contained in DSM 11024, DSM 11012, DSM 11025 or DSM 11014;

(f) nucleic acid molecules encoding a polypeptide comprising the amino acid sequence encoded by the DNA insert contained in DSM 11026, DSM 11011, DSM 11013 or DSM 11027;

(g) nucleic acid molecules comprising the coding sequence of the DNA insert contained in DSM 11024, DSM 11012, DSM 11025 or DSM 11014;

(h) nucleic acid molecules comprising the coding sequence of the DNA insert contained in DSM 11026, DSM 11011, DSM 11013 or DSM 11027;

(i) nucleic acid molecules hybridizing to a molecule of any one of (a), (c), (e) or (g); and (j) nucleic acid molecules the coding sequence of which differs from the coding sequence of a nucleic acid molecule of any one of (a) to (i) due to the degeneracy of the genetic code; and (k) nucleic acid molecules encoding a polypeptide having cellulase activity and having an amino acid sequence which shows at least 80% identity to a sequence as depicted in FIG. 19 (SEQ ID NO: 31), 21 (SEQ ID NO: 33), 23 (SEQ ID NO: 35) or 27 (SEQ ID NO: 37).

The term "hybridization" in this context means hybridization under conventional hybridization conditions, preferably under stringent conditions such as described by, e.g. Sambrook et al. (1989, *Molecular Cloning, A Laboratory Manual* 2nd Edition, Cold Spring Harbor Laboratory Press, Cold Spring Harbor, N.Y.). These nucleic acid molecules that hybridize to the nucleic acid molecules according to the present invention in principle can be derived from any organism possessing such nucleic acid molecules. Preferably, they are derived from fungi, namely from those of the genera *Melanocarpus, Myriococcum, Sporotrichum, Myceliophthora* and *Chaetomium*. Nucleic acid molecules hybridizing to the nucleic acid molecules of the present invention can be isolated, e.g., from genomic libraries or cDNA libraries of various organisms, namely fungi.

Such nucleic acid molecules can be identified and isolated by using the nucleic acid molecules of the present invention or fragments of these molecules or the reverse complements of these molecules, e.g. by hybridization according to standard techniques (see Sambrook et al. (1989)).

As hybridization probe, e.g. nucleic acid molecules can be used that have exactly or substantially the same nucleotide sequence indicated in the Figures or fragments of said sequence. The fragments used as hybridization probes can also be synthetic fragments obtained by conventional synthesis techniques and the sequence of which is substantially identical to that of the nucleic acid molecules according to the invention. Once genes hybridizing to the nucleic acid molecules of the invention have been identified and isolated it is necessary to determine the sequence and to analyze the properties of the proteins coded for by said sequence.

The term "hybridizing DNA molecule" includes fragments, derivatives and allelic variants of the above-described nucleic acid molecules that code for the above-described protein or a biologically active fragment thereof. Fragments are understood to be parts of nucleic acid molecules long enough to code for the described protein or a biologically active fragment thereof. The term "derivative" means in this context that the nucleotide sequences of these molecules differ from the sequences of the above-described nucleic acid molecules in one or more positions and are highly homologous to said sequence. Homology is understood to refer to a sequence identity of at least 40%, particularly an identity of at least 60%, preferably more than 80% and still more preferably more than 90%. The deviations from the nucleic acid molecules described above can be the result of deletion, substitution, insertion, addition or combination.

Homology furthermore means that the respective nucleotide sequences or encoded proteins are functionally and/or structurally equivalent. The nucleic acid molecules that are homologous to the nucleic acid molecules described above and that are derivatives of said nucleic acid molecules are regularly variations of said molecules which represent modifications having the same biological function. They may be naturally occurring variations, such as sequences of other organisms or mutations. These mutations may occur naturally or may be achieved by specific mutagenesis. Furthermore, these variations may be synthetically produced sequences. The allelic variants may be naturally occurring variants as well as synthetically produced or genetically engineered variants.

The proteins encoded by the various variants of the nucleic acid molecules of the invention share specific common characteristics, such as enzymatic activity, molecular weight, immunological reactivity, conformation, etc., as well as physical properties, such as electrophoretic mobility, chromatographic behaviour, sedimentation coefficients, solubility, spectroscopic properties, stability, pH optimum, temperature optimum, etc. Enzymatic activity of the cellulase can be detected e.g. as described on page 11 and in Examples 1 and 25.

The present invention furthermore relates to nucleic acid molecules the sequences of which differ from the sequences of the above-identified molecules due to degeneracy of the genetic code, and which code for a protein having the biological activity of a cellulase.

The nucleic acid molecules of the invention are preferably RNA or DNA molecules, most preferably genomic DNA or cDNA.

The present invention also relates to antibodies which specifically recognize one of the above-described proteins according to the invention as well as to antibody fragments which have this property. These antibodies may be monoclonal or polyclonal. Methods for their production are well known in the art and are described in detail, for example, in Harlow and Lane "*Antibodies, A Laboratory Manual*", CSH Press, Cold Spring Harbor Laboratory (1988).

Furthermore, the present invention relates to oligonucleotides which specifically hybridize with a nucleic acid molecule according to the invention or with the complementary strand of such a nucleic acid molecule. In this respect the term "specifically hybridize" means that such an oligonucleotide hybridizes under stringent hybridization conditions specifically to a nucleic acid molecule of the invention and does not show under such conditions cross-hybridization with sequences coding for other polypeptides. Preferably such oligonucleotides have a length of at least 10 nucleotides, more preferably of at least 15 nucleotides and most preferably of at least 30 nucleotides. They are preferably no longer than 100 nucleotides, more preferably no longer than 80 nucleotides and most preferably no longer than 60 nucleotides. In order to ensure that they specifically hybridize to a nucleic acid molecule of the present invention such oligonucleotides show over their total length an identity of at least 80%, preferably of at least 95% and most preferably of at least 99% with a corresponding nucleotide sequence of a nucleic acid molecule of the present invention. These oligonucleotides may be used, e.g., as probes for screening for sequences encoding cellulases in genomic or cDNA libraries or as PCR primers.

The protein encoding sequences described herein may be fused in frame to other sequences so as to construct DNA encoding a fusion protein. For example, a recombinant vector encoding a 50K-cellulase, a 20K-cellulase, a 50K-cellulase B or the protein-with-CBD gene can be prepared as above, except that the protein encoding sequence is fused with the sequence of a *T. reesei* cellulase, hemicellulase or mannanase, or at least one functional domain of such cellulase, hemicellulase, or mannanase as described in U.S. Pat. No. 5,298,405, WO 93/24622 and in GenBank submission L25310, each incorporated herein by reference. Especially, the cellulase, hemicellulase, or mannanase is selected from the group consisting of CBHI, CBHII, EGI, EGHI, XYLI, XYLII and MANI, or a domain thereof, such as the secretion signal or the core sequence. Mannanase has the same domain structure as that of the cellulases: a core domain, containing the active site, a hinge domain containing a serine-threonine rich region, and a tail, containing the binding domain.

Fusion peptides can be constructed that contain a mannanase or cellobiohydrolase or endoglucanase or xylanase core domain or the core and the hinge domains from the same, fused to the desired protein encoding sequence of the invention. The result is a protein that contains mannanase or cellobiohydrolase or endoglucanase or xylanase core or core and hinge regions, and a 50K-cellulase, 20K-cellulase, 50K-cellulase B or the protein-with-CBD sequence. The fusion protein contains both the mannanase or cellobiohydrolase or endoglucanase or xylanase, and the 50K-cellulase, 20K-cellulase, 50K-cellulase B or the protein-with-CBD activities of the various domains as provided in the fusion construct.

Fusion proteins can also be constructed such that the mannanase or cellobiohydrolase or endoglucanase or xylanase tail or a desired fragment thereof, is included, placed before the 50K-cellulase, 20K-cellulase, 50K-cellulase B or the protein-with-CBD sequence, especially so as to allow use of a nonspecific protease site in the tail as a protease site for the recovery of the 50K-cellulase, 20K-cellulase, 50K-cellulase B or the protein-with-CBD sequence from the expressed fusion protein. Alternatively, fusion proteins can be constructed that provide for a protease site in a linker that is placed before the 50K-cellulase, 20K-cellulase, 50K-cellulase B or the protein-with-CBD sequence, with or without tail sequences.

New properties for the 20K- and 50K-cellulases and for the 50K-cellulase B can be created by fusing domains, such as a cellulose binding domain (CBD), preferably with its linker, to the proteins of the invention. Preferably, such CBD's and linkers are the corresponding CBD and linker domains of a *Trichoderma* cellulase, mannanase or of the *Melanocarpus albomyces* protein-with-CBD.

The invention provides methods for producing enzyme preparations that are partially or completely deficient in an undesirable cellulolytic activity (that is, in the ability to degrade cellulose) and enriched in the 50K-cellulase, 20K-cellulase, 50K-cellulase B or the protein-with-CBD protein, as desired for the textile or detergent industry or for pulp and paper processing. By "deficient in cellulolytic activity" is meant a reduced, lowered, or repressed capacity to degrade cellulose to smaller oligosaccharides. Such cellulolytic activity deficient preparations, and the making of same by recombinant DNA methods, are described in U.S. Pat. No. 5,298,405, incorporated herein by reference. Preferably, the preparation is deficient in EG activities, and/or CBHI activity.

As described herein, the 50K-cellulase, 20K-cellulase, 50K-cellulase B or the protein-with-CBD may be provided directly by the hosts of the invention. Alternatively, spent medium from the growth of the hosts, or purified 50K-cellulase, 20K-cellulase, 50K-cellulase B or the protein-with-CBD therefrom, can be used. Further, if desired activities are present in more than one recombinant host, such preparations may be isolated from the appropriate hosts and combined prior to use in the method of the invention.

To obtain the enzyme preparations of the invention, the native or recombinant hosts described above having the desired properties (that is, hosts capable of expressing economically feasible quantities of the desired 50K-cellulase, 20K-cellulase, 50K-cellulase B or protein-with-CBD, and optionally, those that are substantially incapable of expressing one or more other, undesired cellulase enzymes) are cultivated under suitable conditions, the desired enzymes are secreted from the hosts into the culture medium, and the enzyme preparation is recovered from said culture medium by methods known in the art.

The enzyme preparations of the invention can be produced by cultivating the recombinant hosts or native strains in a fermentor on a suitable growth medium (such as, for example, shown in Example 1 or in Example 30).

The enzyme preparation can be the culture medium with or without the native or transformed host cells, or is recovered from the same by the application of methods well known in the art. However, because the 50K-cellulase, 20K-cellulase or 50K-cellulase B are secreted into the culture media and display activity in the ambient conditions of the cellulolytic liquor, it is an advantage of the invention that the enzyme preparations of the invention may be utilized directly from the culture medium with no further purification. If desired, such preparations may be lyophilized or the enzymatic activity otherwise concentrated and/or stabilized for storage. The enzyme preparations of the invention are very economical to provide and use because (1) the enzymes may be used in a crude form; isolation of a specific enzyme from the culture medium is unnecessary and (2) because the enzymes are secreted into the culture medium, only the culture medium need be recovered to obtain the desired enzyme preparation; there is no need to extract an enzyme from the hosts. Preferably the host for such production is *Trichoderma*, and especially *T. reesei*.

The enzyme preparations of the invention may be provided as a liquid or as a solid, for example, in a dried powder or granular or liquid form, especially nondusting granules, or a stabilized liquid, or the enzyme preparation may be otherwise concentrated or stabilized for storage or use. It is envisioned that enzyme preparations containing one or more of the neutral cellulases of the invention can be further enriched or made partially or completely deficient in specific enzymatic activities, so as to satisfy the requirements of a specific utility in various applications e.g. in the textile industry. A mixture of enzyme activities secreted by a host and especially a fungus, can be chosen to be advantageous in a particular industrial application, for example biostoning.

The enzyme preparations of the invention can be adjusted to satisfy the requirements of specific needs in various applications in the textile, detergent or the pulp and paper industry.

Blends may be prepared with other macromolecules that are not all secreted from the same host (for example, other enzymes such as endoglucanases, proteases, lipases, peroxidases, oxidases or amylases) or chemicals that may enhance the performance, stability, or buffering of the desired enzyme preparation. Non-dusting granules may be coated. Liquid enzyme preparations can be stabilized by adding a polyol such as propylene glycol, a sugar or sugar alcohol, lactic acid or boric acid, according to established methods. Liquid detergents generally contain up to 90% water and 0-20% organic solvent. Protected forms of the enzymes of the invention may be prepared as described in EP 238,216.

The enzyme preparations of the invention can contain a surfactant which can be anionic, non-ionic, cationic, amphoteric or a mixture of these types, especially when used as a detergent composition. Useful detergent compositions are described e.g. in WO 94/07998, U.S. Pat. Nos. 5,443,750 and 3,664,961.

If required, a desired enzyme may be further purified in accordance with conventional conditions, such as extraction, precipitation, chromatography, affinity chromatography, electrophoresis, or the like.

The enzyme preparations of this invention are especially useful in textile industry preferably in biostoning and in biofinishing or in detergent industry. Other useful areas are in pulp and paper industry.

Non-enzymatic stonewashing has three steps: desizing, abrasion and aftertreatment. The first step, desizing, involves the removal of the starch coating, or that of its derivatives, by amylase. The second step, abrasion, when performed without cellulase, is generally performed by washing the denim with pumice stones, and, when lightening is desired, bleach. The abrasive effect is the result not only of the effect of the stones but also the rubbing together of the denim fabric. Abrasion is generally followed by the third step, a washing step to remove excess dye, during which softeners or optical brighteners can be added.

In enzymatic stonewashing, or biostoning, abrasion with pumice stones is completely or partially eliminated and cellulase is added to facilitate the abrasion of indigo dye from the fiber surface. After this treatment, the cellulase is removed with a detergent wash to ensure that the mechanical strength of the fiber is not further compromised by the continued presence of the enzyme. Treatment with a cellulase(s) can completely replace treatment with pumice stones (for example, 1 kg commercial enzyme per 100 kg stones). However, cellulase treatment can be combined with pumice stone treatment when it is desired to produce a heavily abraded finish. A peach skin effect in which a fine protruding hair-like covering is created is also achieved by a wash combining a neutral cellulase with pumice stones. The cellulases of this invention are useful especially to minimize backstaining and enhance lightening (abrasion) in biostoning.

Biostoning is preferably performed from about pH 4.5-9.5, and most preferably between pH 6.0-8.5. The temperature of the reaction can range from about 40-80° C., preferably between 50-70° C., and most preferably between 50-60° C. The liquid ratio (the ratio of the volume of liquid per weight of fabric) may range from about 2:1-20:1, preferably 4:1-10:1, and most preferably 4:1-7:1. The enzyme dosage can range from about 25-1500 nkat/g fabric, preferably 50-500 nkat/g fabric and most preferably 75-300 nkat/g fabric.

The cellulases of the invention are useful in the textile industry for biofinishing of fabrics or garments e.g. depilling, defuzzing, colour clarification, harshness reduction, the creation of different finishes (for example, a 'peach skin,' 'worn out,' 'sand washed,' or 'antique look' effect) and biofinishing of yarn (for example reduction of hairiness, improvement of smoothness). The cellulases of this invention can be used in biofinishing in acidic and in neutral conditions.

The cellulases of this invention are useful in detergent compositions to improve the textile cleaning effect e.g. soil removal, to improve the fabric-care properties by reducing the harshness of the textiles, the cellulases having also defuzzing and colour clarification and restoring effects.

The textile material that is treated with the enzyme preparations of the invention may be manufactured of natural cellulose containing fibers or manmade cellulose containing fibers or mixtures thereof. Examples of natural cellulosics are cotton, linen, hemp, jute and ramie. Examples of manmade cellulosics are viscose, cellulose acetate, cellulose triacetate, rayon, cupro and lyocell. The above mentioned cellulosics can also be employed as blends of synthetic fibers such as polyester, polyamide or acrylic fibers. The textile material may be yarn or knitted or woven or formed by any other means.

The cellulases of the invention, besides being especially useful for the treatment of fabric, are useful in general in any area requiring cellulase activity. In the pulp and paper industry, neutral cellulases can be used, for example, in deinking of different recycled papers and paperboards having neutral or alkaline pH, in improving the fiber quality, or increasing the drainage in paper manufacture. Other examples include the removal of printing paste thickener and excess dye after textile printing, and as a treatment for animal feed. For example, if the intended application is improvement of the strength of the mechanical pulp, then the 50K-cellulase, 20K-cellulase, 50K-cellulase B or the protein-with-CBD preparations of the invention may provide one or more of these proteins so as to enhance or facilitate the ability of cellulose fibers to bind together. In a similar manner, in the application of pulp refining, the 50K-cellulase, 20K-cellulase, 50K-cellulase B or protein with CBD preparations of the invention may provide one or more of these proteins at a level that enhance or facilitate such swelling.

The invention is described in more detail in the following examples, These examples show only a few concrete applications of the invention. It is self evident for one skilled in the art to create several similar applications. Hence the examples should not be interpreted to narrow the scope of the invention only to clarify the use of the invention.

EXAMPLES

Example 1

Shake Flask and Fermentor Cultivations

For maintenance, the strains ALKO4179, ALKO4124, ALKO4237, ALKO4265 and ALKO4125 were streaked on sporulation agar (ATCC medium 5, American Type Culture Collection, Catalogue of Filamentous Fungi, 18th edition, eds., S. C. Jong and M. J. Edwards, (1991): 1 liter contains 1 g yeast extract, 1 g beef extract, 2 g tryptose, a trace amount of $FeSO_4$, 10 g glucose and 15 g agar; the pH was 7.2. Agar slants were incubated at 45° for 3-6 days.

For the applications tests of ALKO4237 (Examples 3 and 4), a colony was inoculated in 500 ml of the following mineral medium (Moloney, A. P. et al., *Biotechnol. Bioeng.* 25:1169 (1983)): 1 liter contains 15 g $KH_2PO_4$, 15 g $(NH_4)_2SO_4$, 2.4 ml of 1 M $MgSO_4 \times 7H_2O$, 5.4 ml 1 M $CaCl_2$, 20 g Solka floc, 15 g corn steep powder, 1 g yeast extract and 10 ml 100×trace element solution 1, where 1 liter of 100×trace element solution 1 contains 0.5 g $FeSO_4 \times 7H_2O$, 0.156 g $MnSO_4 \times H_2O$, 0.14 g $ZnSO_4 \times 7H_2O$ and 0.49 g $CoS_4O \times 7H_2O$; the pH was adjusted to pH 6.5. Cultivation was performed at 45° C. for 3 days in a rotatory shaker (250 rpm). Endoglucanase activity of about 20-25 nkat/ml was obtained.

Cellulase activity was routinely measured as endoglucanase activity according to Bailey, M. J. et al., *Enzyme Microb. Technol.* 3:153 (1981)), using 1% (w/v) hydroxyethylcellulose, HEC (Fluka AG #54290) as a substrate. The assay conditions were, if not otherwise stated, pH 7.0 and 50° C. with a 10 minute reaction time. One endoglucanase unit (1 nkat=1 ECU) is defined as the amount of enzyme that produces reducing carbohydrates having a reducing power corresponding to one nanomole of glucose in one second from HEC under the assay conditions. However, with the purified enzymes described in Examples 9-12, the assay conditions of Bailey et al., *Enzyme Microb. Technol.* 3:153 (1981) exceed the linear range, and the assay was therefore modified as described in Example 10. With every strain, the filter paper activity assay (which measures the total hydrolysis of cellulose and indicates the presence of cellobiohydrolase activity) was either under the reliable detection limit or very low.

For the determination of pH and temperature dependency (Example 2), as well as for the application tests of the strains ALKO4179, ALKO4124, ALKO4265 and ALKO4125 (Examples 3 and 4), colonies were inoculated in 500 ml of the modified thermomedium B (G. Szakacs, Technical University of Budapest, Hungary): 1 liter contained 6 g Solka floc, 6 g distiller's spent wheat grain, 3 g oat spelt xylan, 2 g $CaCO_3$, 1.5 g soybean meal, 1.5 g $(NH_4)_2HPO_4$, 1 g barley bran, 0.5 g $KH_2PO_4$, 0.5 g $MgSO_4 \times 7H_2O$, 0.5 g NaCl, 0.5 ml trace element solution 1 (1 liter contains: 1.6 g $MnSO_2$, 3.45 g $ZnSO_4 \times 7H_2O$, and 2.0 g $CoCl_4 \times 6H_2O$) and 0.5 ml trace element solution 2 (1 liter contains: 5.0 g $FeSO_4 \times 7H_2O$ and two drops of concentrated $H_2SO_4$); the pH was adjusted to pH 6.5. Cultivations were performed at 45° C. for 3 days in a rotatory shaker (250 rpm). Because in thermomedium B the endoglucanase activities of the strains ALKO4179, ALKO4124, and ALKO4237 were about 5 nkat/ml, culture filtrates were concentrated about 10 fold in an Amicon concentrator using a cut-off of 30 kDa. Endoglucanase activity obtained with ALKO 4265 was about 20 nkat/ml and with ALKO 4125 30-40 nkat/ml.

The 1 liter fermentor cultivation of ALKO4179 was performed in the following medium: 1 liter contained 10 g Solka floc, 3 g cellobiose, 4 g corn steep powder, 1.5 g $(NH_4)_2HPO_4$, 0.3 g $MgSO_4 \times 7H_2$, 0.5 g NaCl, 2 g $CaCO_3$, 0.5 ml trace element solution 1 and 0.5 ml trace element solution 2, 0.5 g $KNO_3$, 0.3 g $CaCl_2$, 1 g Tween 80; the pH was adjusted to pH 6.5.

The 1 liter fermentor cultivation of ALKO4124 was performed in the modified thermomedium B: 1 liter contained: 10 g Solka floc, 1 g Roth's xylan, 40 g whey, 30 g soybean meal, 2 g $CaCO_3$, 5 g $(NH_4)_2SO_4$, 0.5 g $KH_2PO_4$, 1.0 g $MgSO_4 \times 7H_{20}$, 1.0 g NaCl, 1 g antifoam, 0.5 ml trace element solution 1 and 0.5 ml trace element solution 2.

The 1 liter fermentor cultivation of ALKO4237 was performed in the mineral medium mentioned above. 10% (v/v) inoculum was used. pH was maintained at pH 6.5±0.4 by the addition of ammonia [12.5% (v/v)] and phosphoric acid [17% (v/v)]. The fermentation temperature was 45° C. The fermentor (Biostat M, B. Braun, Melsungen, Germany) was stirred at 400 rpm and the air flow as 1 vvm. The endoglucanase activities obtained were the following: ALKO4179 about 40 nkat/ml, ALKO4124 about 90 nkat/ml and ALKO4237 about 30 nkat/ml. ALKO4265 and ALKO4125 were not cultivated in a fermentor.

ALKO4179, ALKO4124, ALKO4237 and ALKO4125 were cultivated in a 100 liter pilot fermentor in media and conditions described above. Endoglucanase activities obtained were about 40 nkat/ml with ALKO4179 and ALKO4237, about 90 nkat/ml with ALKO4124 and about 100 nkat/ml with ALKO4125. Culture filtrates were concentrated 10-20 fold in a Millipore PUF100 ultra filter and a Pellicon Us cassette concentrator using a cut-off of 10 kDa.

Example 2

Figure 1A:
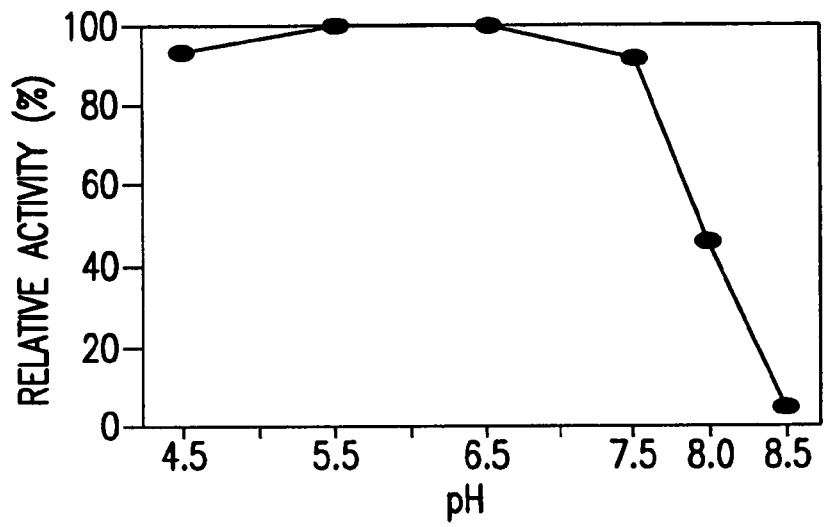
FIGS. 1 (A and B) show the pH (FIG. 1A) and temperature (FIG. 1B) dependencies of the endoglucanase activities of ALKO4179, CBS 689.95
Figure 2A:
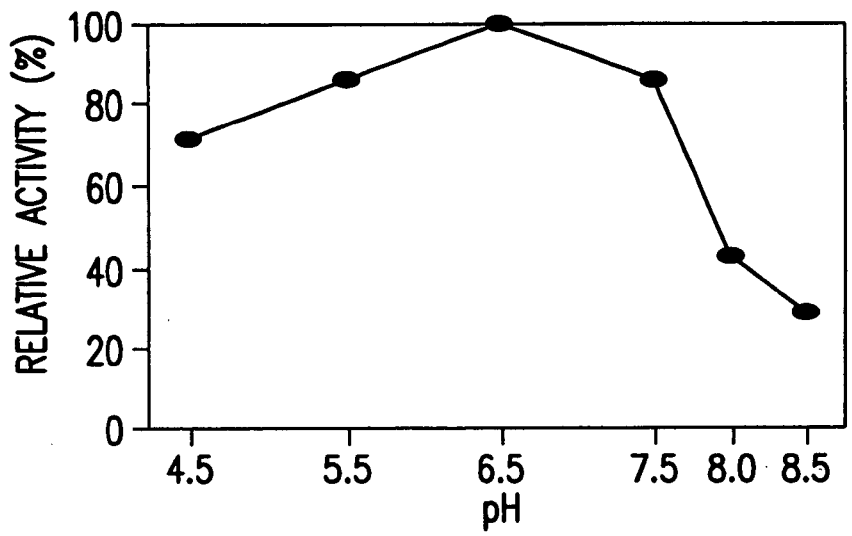
FIGS. 2 (A and B) show the pH (FIG. 2A) and temperature (FIG. 2B) dependencies of the endoglucanase activities of ALKO4124, CBS 687.95.
Figure 3A:
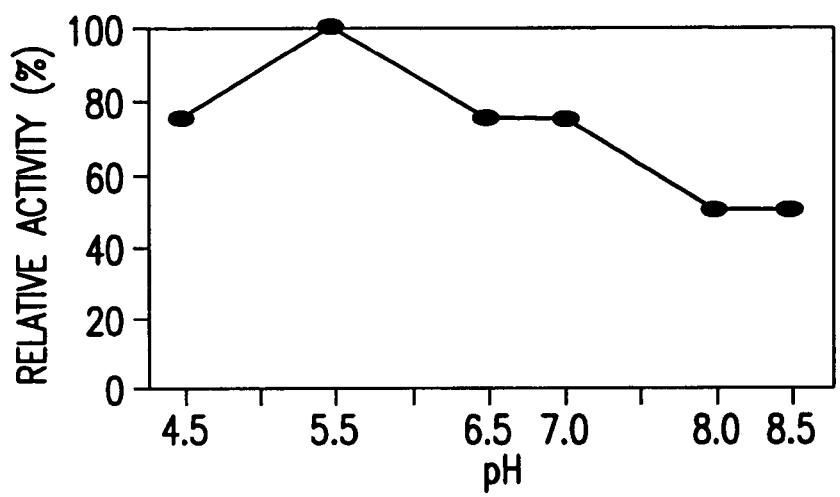
FIGS. 3 (A and B) show the pH (FIG. 3A) and temperature (FIG. 3B) dependencies of the endoglucanase activities of ALKO4237, CBS. 685.95.
Figure 4A:
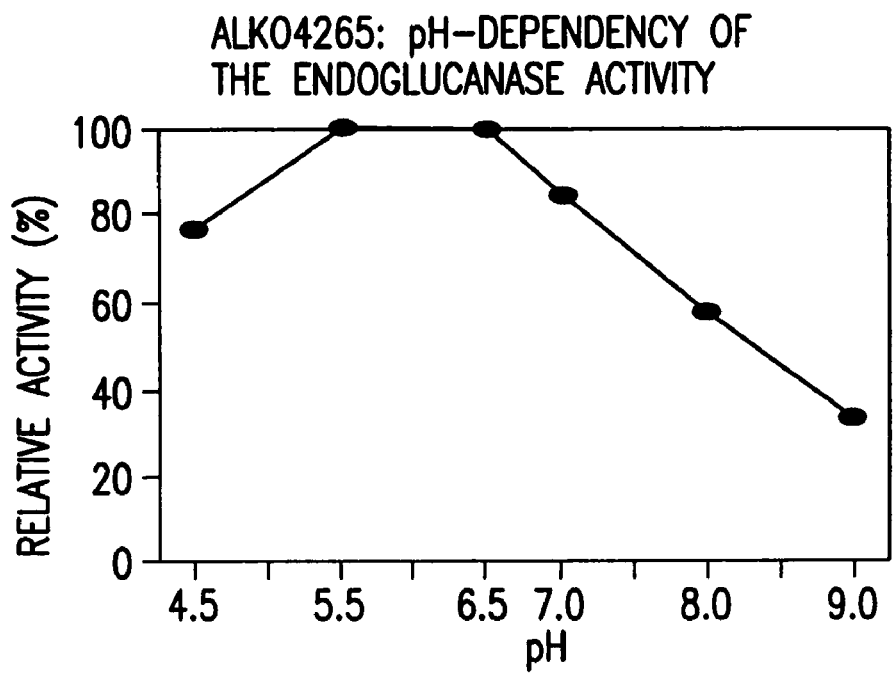
FIGS. 4 (A and B) show the pH (FIG. 4A) and temperature (FIG. 4B) dependencies of the endoglucanase activities of ALKO4265, CBS 730.95.
Figure 5A:
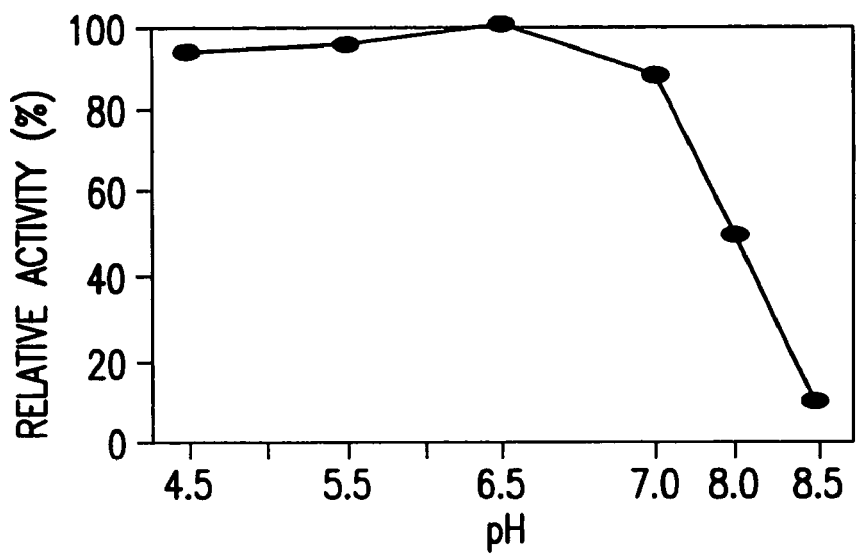
FIGS. 5 (A and B) show the pH (FIG. 5A) and temperature (FIG. 5B) dependencies of the endoglucanase activities of ALKO4125, CBS 688.95.

Determination of the pH and the Temperature Dependence of the Endoglucanase Activities in the Culture Filtrates For the determination of pH and temperature dependence, the strains ALKO4179, ALKO4124, ALKO4237, ALKO4265 and ALKO4125 were grown in the modified thermomedium B. Samples from the shake flask cultivations (culture filtrates) were diluted in 50 mM McIlvain's buffers (50 mM citric acid-100 mM $Na_2HPO_4$) of pH range 4.5-8.5. The final pH values of the culture filtrate buffer mixtures were 4.3, 5.4, 6.3, 7.3, 8.1 and 8.7 for the strain ALKO4179; 4.3, 5.4, 6.4, 7.3, 8.1 and 8.5 for the strain ALKO4124; 4.4, 5.3, 6.2, 7.1, 8.0 and 8.5 for the strain ALKO4237; 4.3, 5.4, 6.3, 7.2, 8.1 and 8.5 for the strain ALKO4265 and 4.3, 5.4, 6.4, 7.3, 8.1 and 8.5 for the strain ALKO4125. BSA was added as a protein carrier to the concentration of 100 µg/ml. Pepstatin A and phenyl methyl sulphonyl fluoride (PMSF) were added as protease inhibitors at 10 µg/ml and 174 µg/ml, respectively. Endoglucanase activity was measured at each pH at 50° C. with 60 minutes reaction time. The endoglucanase activity of ALKO4179 exhibited more than 90% of its maximum in the pH range of about 4.5-7.5, the maximum activity was detected at about pH 5.4-6.3 (FIG. 1A). The endoglucanase activity of ALKO4124 exhibited more than 80% of its maximum activity in the pH range about 5.5-7.5, the maximum activity was detected at about pH 6.4 (FIG. 2A). The endoglucanase activity of ALKO4265 exhibited more than 80% of its maximum activity in the pH range about 4.5-7.0, the maximum activity was detected at about pH 5.5-6.5 (FIG. 4A). The endoglucanase activity of ALKO4237 exhibited more than 80% of its maximum in the pH range of about 4.5-6.0, the maximum activity was detected at about pH 5.3 (FIG. 3A). The endoglucanase activity of ALKO4125 exhibited about 90% of its maximum in the pH range of about 4.5-7.5, the maximum activity was detected at about pH 6.5 (FIG. 5A).

Figure 1B:
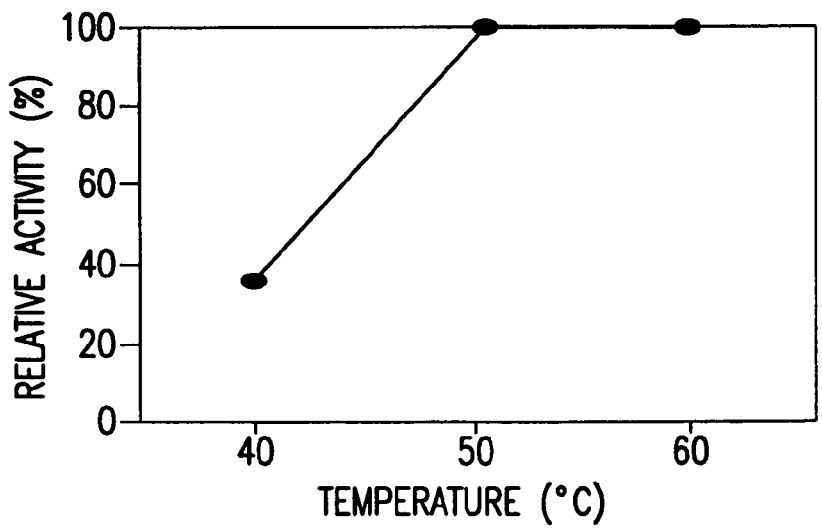
Figure 2B:
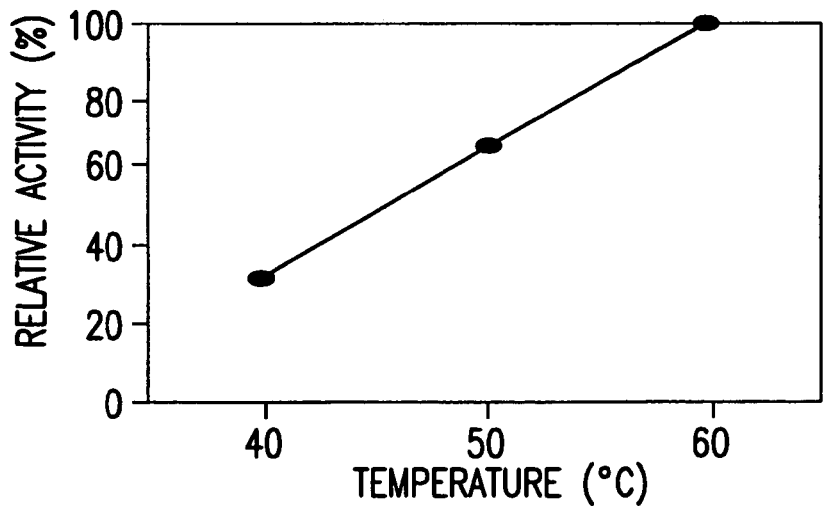
Figure 3B:
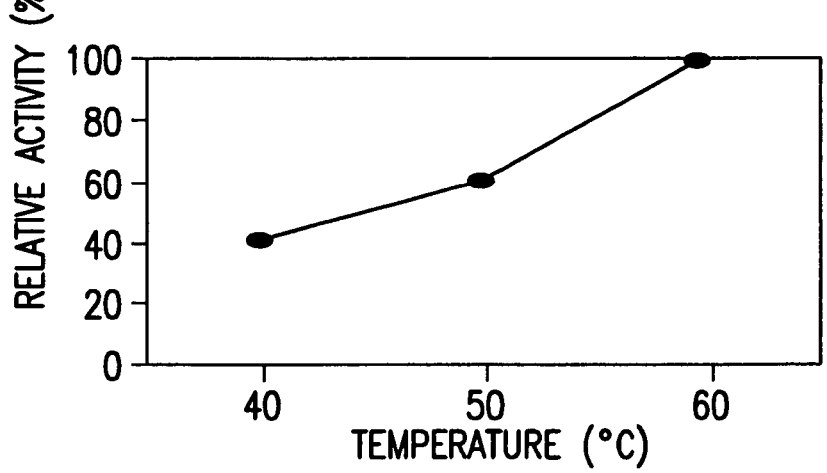
Figure 4B:
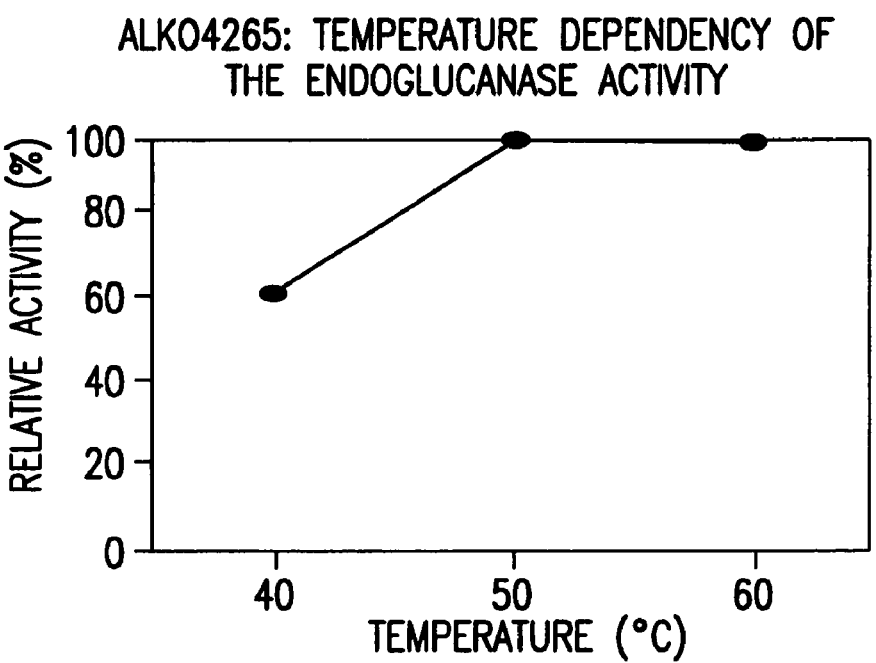
Figure 5B:
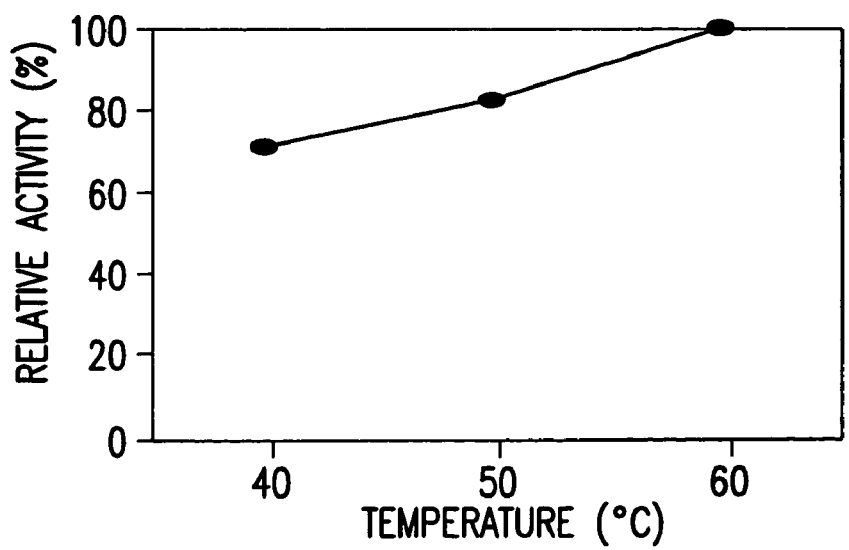

For the temperature dependency determination of the endoglucanase activity, samples from the culture filtrates were diluted in 50 mM McIlvain's buffer, pH 7.0. BSA was added as a protein carrier to the concentration of 100 µg/ml. Pepstatin A and phenyl methyl sulphonyl fluoride (PMSF) were added as protease inhibitors to 10 µg/ml and 174 µg/ml, respectively. The final pH values of the culture filtrate buffer mixtures were 7.3 (ALKO4179, ALKO4124 and ALKO4125) and 7.2 (ALKO4237 and ALKO4265). Samples were incubated at 40° C., 50° C. and 60° C. for 60 minutes. The maximum endoglucanase activity of ALKO4179 was detected at 50° C. and 60° C., about 30% of the activity was retained at 40° C. (FIG. 1B). The maximum endoglucanase activity of ALKO4124 was detected at 60° C., about 70% of the activity was retained at 50° C. and 30% at 40° C. (FIG. 2B). The maximum endoglucanase activity of ALKO4237 was detected at 60° C., about 60% of the activity was retained at 50° C. and 40% at 40° C. (FIG. 3B). The maximum endoglucanase activity of ALKO4265 was detected at 60° C., about 50% of the activity was retained at 50° C. and 30% at 40° C. (FIG. 4B). The maximum endoglucanase activity of ALKO4125 was detected at 60° C., about 80% of the activity was retained at 50° C. and 70% at 40° C. (FIG. 5B).

Example 3

Indigo Dye Release in Neutral Conditions

Cellulase preparations derived from the strains ALKO4179, ALKO4124, ALKO4237, ALKO4265 and ALKO4125 (Examples 1 and 2) were tested for their ability to release dye in neutral conditions from the indigo dyed cotton-containing denim fabric to give a stone-washed look. Commercial acid cellulase product Ecostone L (Primalco Ltd, Biotec, Finland) was used as a control.

Denim fabric was obtained from Lauffenmuehl (Germany). Test fabric was prewashed 10 min at 60° C. with Ecostone A 200 (1 ml/liter, Primalco Ltd, Biotec, Finland). The fabric was then cut into 12×12 cm swatches. The colour from both sides of the fabric swatches was measured as reflectance values with the Minolta (Osaka, Japan) Chroma Meter CM 1000R L*a*b* system.

Cellulase treatments were performed in LP-2 Launder-Ometer (Atlas, Ill., USA) as follows. About 7 g of denim swatches were loaded into the 1.2 liter container that contained 200 ml of 0.05 M citrate/phosphate buffer at pH 7, or, 0.05 M citrate buffer at pH 5.2. 0.06 ml of 10% Berol 08 (Berol Nobel AS, Sweden) was added as a surfactant.

A quantity of steel balls were added into each container to help the fiber removal. Finally the cellulase solutions were added to the container as endoglucanase activity units (Example 1). The containers were then closed and loaded into a 50° C. Launder-Ometer bath. The Launder-Ometer was run at 42 rpm for 2 hours.

After removing swatches from the containers they were soaked for 10 min in 200 ml of 0.01 NaOH and rinsed for 10 min with cold water. Swatches were then dried for 1 hour at 105° C. and air dried overnight. The color from both sides of the swatches was measured with the Minolta Chroma Meter. Results from the color measurements of treated denim fabrics are shown in Table I.

TABLE I

Color Measurement of Denim Fabrics Treated with Different Cellulase Preparations.

| Source of Enzyme | ECU/g of fabric | Right side of the Fabric | | | Reverse side of the Fabric | | |
|---|---|---|---|---|---|---|---|
| | | L | b | delta E | L | b | delta E |
| pH 7* | | | | | | | |
| — | — | 2.3 | 0.8 | 3.1 | 1.5 | 0.1 | 0.9 |
| ALKO4237 | 200 | 6.4 | 3.3 | 7.6 | 2.4 | 1.7 | 3.2 |
| | 400 | 7.7 | 3.8 | 8.1 | 2.5 | 1.8 | 3.0 |
| ALKO4179 | 200 | 5.5 | 2.4 | 6.4 | 2.8 | 1.9 | 3.0 |
| | 400 | 4.6 | 2.8 | 5.1 | 2.2 | 1.5 | 3.0 |
| ALKO4124 | 200 | 4.8 | 2.8 | 6.1 | 3.3 | 1.2 | 2.5 |
| | 400 | ND | ND | ND | ND | ND | ND |
| ALKO4125 | 200 | 4.0 | 2.7 | 5.6 | 2.3 | 1.5 | 2.3 |
| | 400 | ND | ND | ND | ND | ND | ND |
| ALKO4265 | 200 | 2.2 | 3.6 | 5.1 | -4.9 | 6.6 | 9.2 |
| | 400 | ND | ND | ND | ND | ND | ND |
| Ecostone L | 200 | 1.6 | 0.7 | 1.6 | 0 | 1.7 | 1.6 |
| | 400 | 1.6 | 0.9 | 1.8 | -1.9 | 2.2 | 2.8 |
| pH 5.2** | | | | | | | |
| Ecostone L | 200 | 2.01 | 2.33 | 3.30 | -2.74 | 4.35 | 4.71 |
| | 400 | 3.19 | 2.76 | 4.35 | -2.56 | 4.83 | 6.71 |

L: Lightness unit of the fabric after the treatment minus lightness unit of the fabric before the treatment.
b: Blueness unit of the fabric after the treatment minus blueness unit of the fabric before the treatment.
delta E: Color difference in the L*a*b* color space between the specimen color and the target color (target fabric = untreated denim fabric).
ND = not done.
*the ECU activity was measured at pH 7.0.
**the ECU acticity was measured at pH 4.8.

To compare the final look of the denim fabrics after washing with different cellulase preparations, the color from both sides (reverse side and right side) of the fabrics was measured. From the results shown in Table I, it can be seen that the lightness and blueness units are clearly increased on the right side of the garments washed with preparations of ALKO4179, ALKO4124, ALKO4237 and ALKO4125 cellulases, showing a good stone-washed effect. The blueness unit was also increased on the right side of the fabric washed with the ALKO4265 preparation but there was no increase in the lightness unit. This is probably because the enzyme does work at this pH but at the same time causes a lot of backstaining. There was no stone washing effect on the fabric with commercial acid product Ecostone L at pH 7 at this ECU activity.

In this study, backstaining on the reverse side of the fabric is used as an indication of the degree of backstaining on the right side of the fabric. To quantify the level of backstaining, the color was measured on the reverse side of the fabric before and after the cellulase treatment. As shown in Table I, when the ECU amounts are the same, there was practically no backstaining in the fabrics treated with the ALKO4179, ALKO4124, ALKO4237 and ALKO4125 preparations when compared to the fabrics treated with ALKO4265 or Ecostone L (pH 5.2 and 7) preparations.

Example 4

Dye Release in Neutral Conditions, No Berol

The experimental set-up was as described in Example 3 except that no Berol was used. Results from the color measurements of treated denim fabrics are shown in Table II.

TABLE II

Color Measurement of Denim Fabrics Treated with Different Cellulase Preparations - no Berol.

| Source of Enzyme | ECU/g of fabric | Right side of the Fabric | | | Reverse side of the Fabric | | |
|---|---|---|---|---|---|---|---|
| | | L | b | delta E | L | b | delta E |
| pH 7* | | | | | | | |
| — | — | 2.1 | 0.5 | 2.2 | 1.7 | −1.1 | 2.0 |
| ALKO4237 | 200 | 5.5 | 3.1 | 7.0 | 1.8 | 2.3 | 3.5 |
| ALKO4179 | 200 | 4.4 | 3.2 | 5.6 | 1.4 | 2.2 | 2.7 |
| ALKO4124 | 200 | 4.2 | 2.9 | 5.0 | 1.1 | 2.0 | 2.4 |
| ALKO4125 | 200 | 3.5 | 2.6 | 4.4 | 1.6 | 1.4 | 2.5 |
| ALKO4265 | 200 | 3.3 | 3.3 | 5.3 | −5.7 | 6.6 | 10.0 |
| Ecostone L | 200 | 1.4 | 0.9 | 1.7 | 0.3 | 1.4 | 1.8 |
| | 400 | 1.4 | 0.8 | 1.7 | −0.1 | 1.7 | 1.8 |
| pH 5.2** | | | | | | | |
| Ecostone L | 200 | 2.0 | 2.1 | 2.9 | −4.0 | 4.8 | 5.4 |

L: Lightness unit of the fabric after the treatment minus lightness unit of the fabric before the treatment.
b: Blueness unit of the fabric after the treatment minus blueness unit of the fabric before the treatment.
delta E: Color difference in the L*a*b* color space between the specimen color and the target color (target fabric = untreated denim fabric).
ND = not done.
*the ECU activity was measured at pH 7.0.
**the ECU activity was measured at pH 4.8.

When compared with results obtained with the inclusion of Berol (Example 3), the data in Table II show that almost the same stone-washing effect can be achieved with the ALKO4179, ALKO4124, ALKO4237 and ALKO4125 cellulase preparations in the absence of the helping agent Berol.

Example 5

Backstaining in Denim Wash with Different Cellulases

In the literature, it is reported that backstaining is dependent on pH and/or the type of enzyme. However, as shown herein, it was found that backstaining depends only indirectly on pH (FIGS. 6A and 6B and 7A and 7B).

Figure 6A:
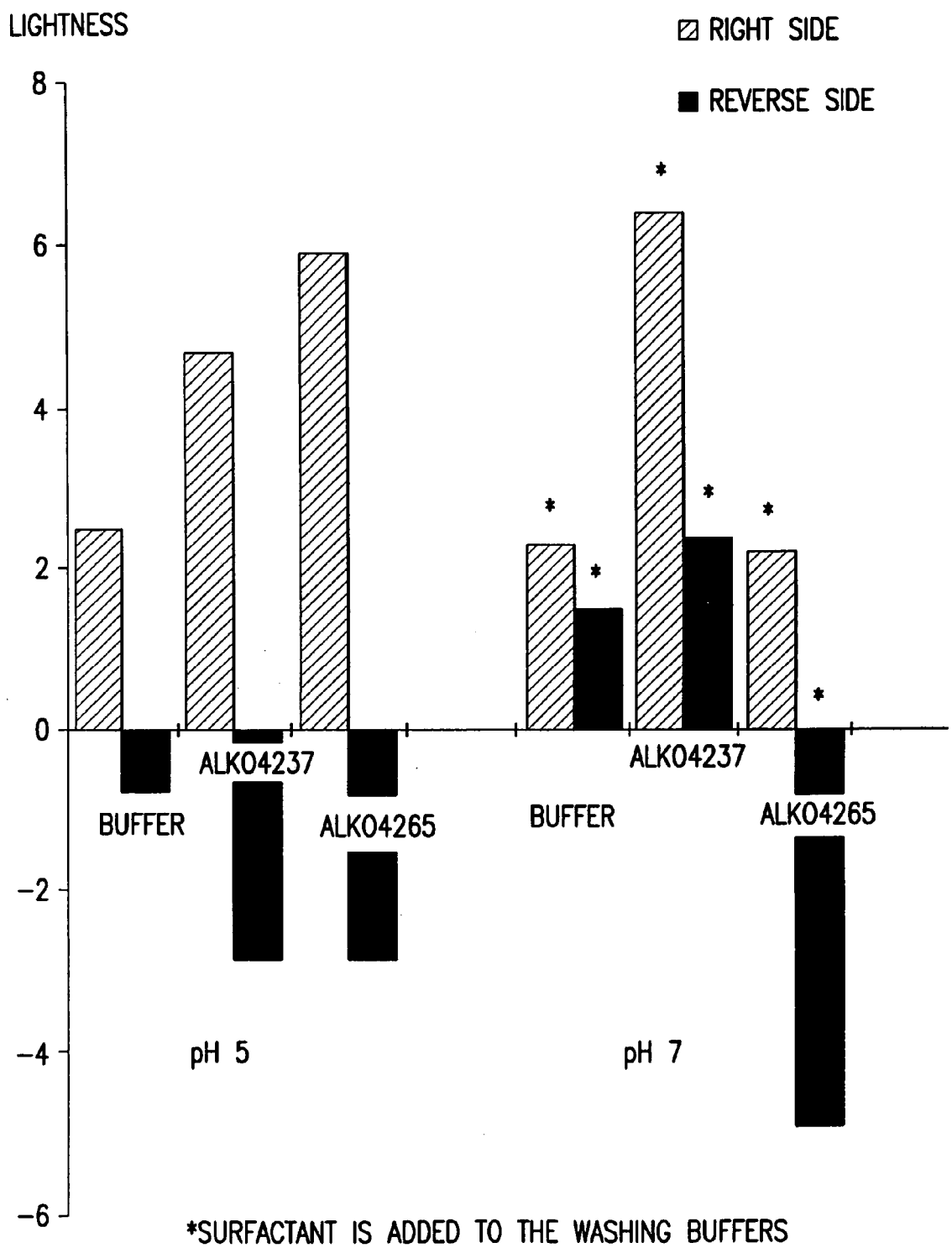
FIGS. 6 (A and B) show the wash effect and backstaining (FIG. 6A) and blueness (FIG. 6B) with the neutral cellulases.
Figure 6B:
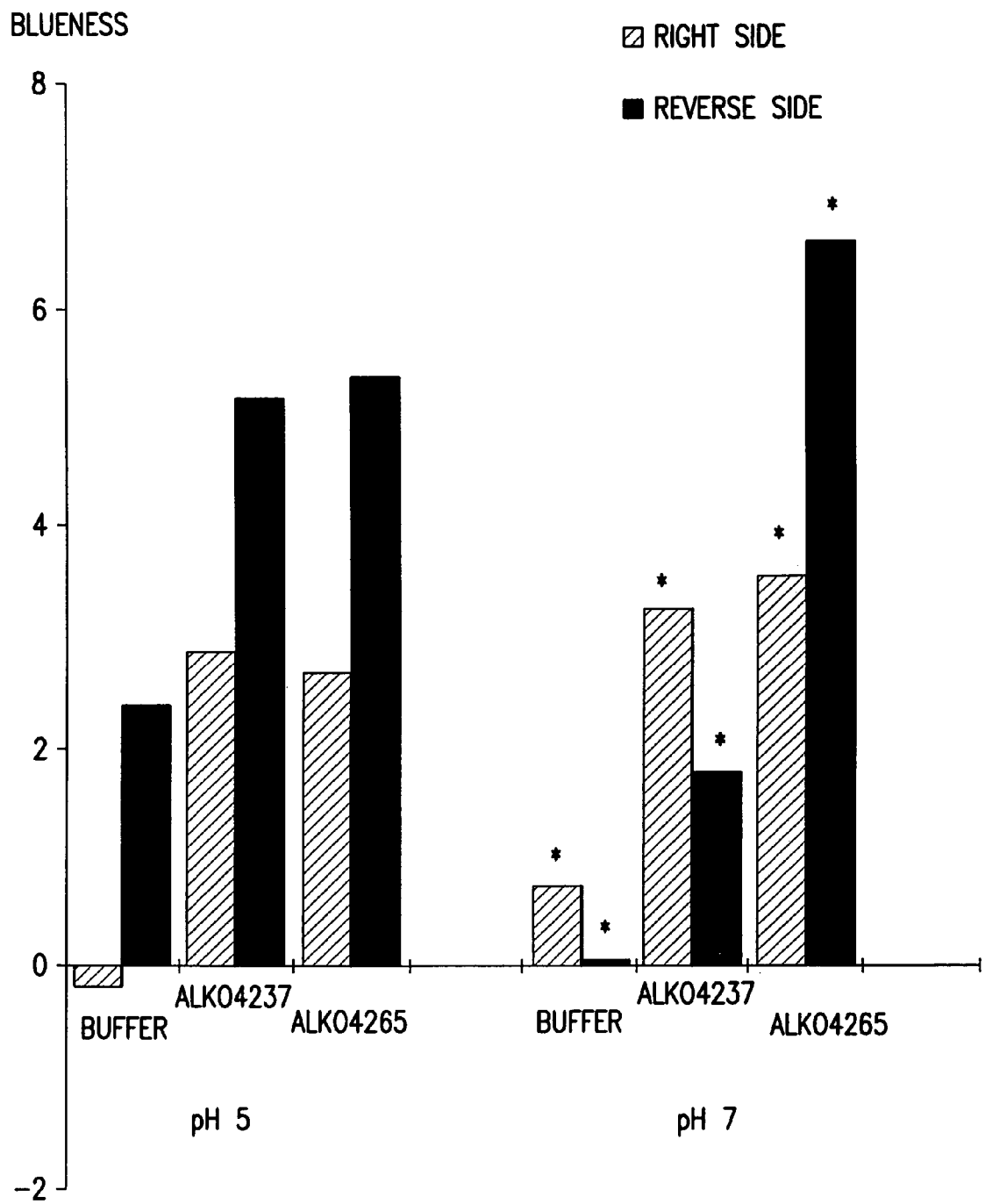
Figure 7A:
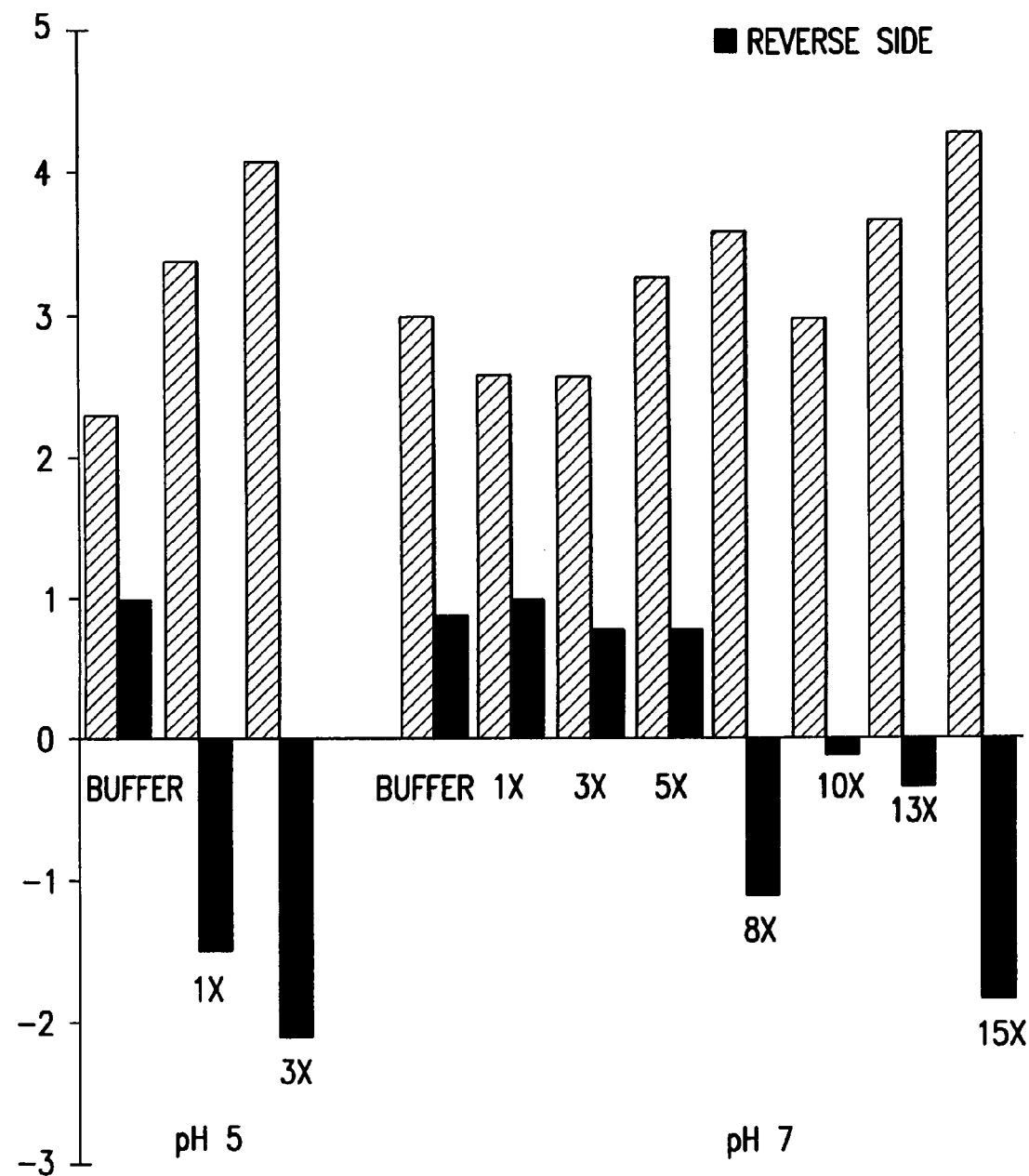
FIGS. 7 (A and B) show the wash effect and backstaining (FIG. 7A) and blueness (FIG. 7B) with Ecostone L with gradually increasing enzyme dosages. 1X corresponds the enzyme dosage of the neutral cellulases in FIGS. 6A and 6B.
Figure 7B:
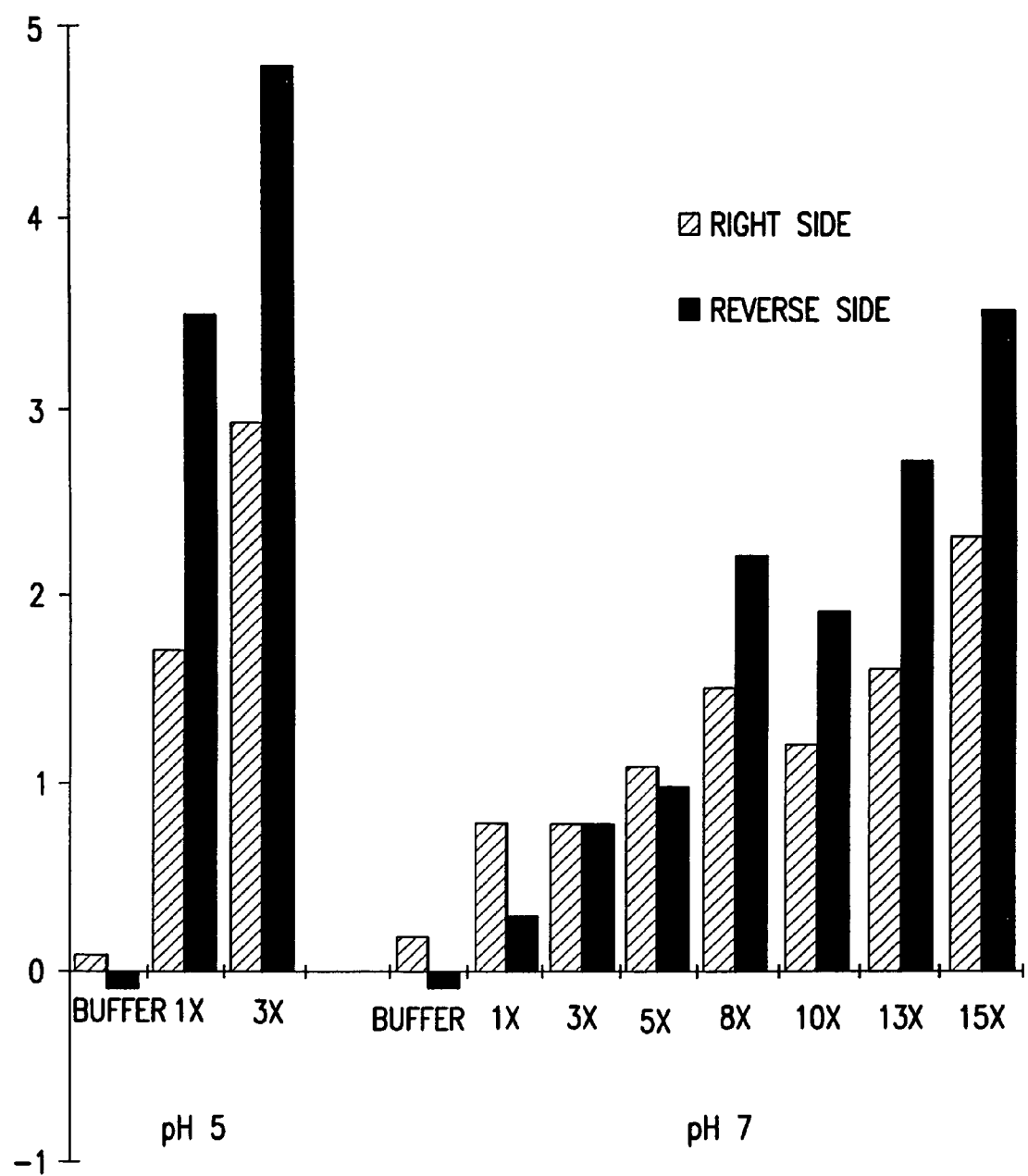

Two neutral cellulase preparations from ALKO4237 and from ALKO4265 and acid cellulase product Ecostone L were studied in small scale denim wash with an equal enzyme dosage at pH 5 and pH 7. The stonewash effect was determined by measuring the increase of lightness and blueness as reflectance units on the right side of the fabric and backstaining (redeposition of indigo on the surface of fibers) was determined as blueness increase and lightness decrease on the reverse side. At pH 7, the neutral cellulases from ALKO4237 caused a clear increase in lightness and blueness on the right side and no backstaining was observed (FIGS. 6A and 6B). A similar stonewash effect was found at pH 5 but with a slight backstaining. At pH 7, the other neutral cellulase, ALKO4265, brightened blueness on the right side but backstained intensively on the reverse side. At pH 5 similar effects were obtained with both ALKO4265 and ALKO4237 preparations. At pH 7, the acid cellulase did not backstain or impart a lightness on the right side (when using similar endoglucanase activity dosages as with ALKO4265 and ALKO4237, FIGS. 7A and 7B, 1× dosage), probably because it did not work at this pH. On the other hand, at pH 5, lightness and blueness were increased on the right side and backstaining was clearly perceptible on the reverse side. Based on these results, backstaining can occur at both pH values depending on the cellulase preparation used.

Example 6

Use of the Neutral Cellulase-Containing Enzyme Preparations in Biofinishing of Cotton-Containing Woven Fabric 100% cotton woven fabric was subjected to treatment with ALKO4237 (Example 1) and ALKO4467 cellulases in Launder-Ometer. ALKO4467 is a UV-mutant with higher cellulase activity derived from ALKO4125.

100% cotton woven fabric (obtained from Pirkanmaan Uusi Värjäämö Ltd) was pretreated as in Example 7. The cellulase treatment conditions were as described in Example 3 except that no Berol was used and the liquid ratio was 1:15 (volume of liquid per weight of fabric). Cellulases were dosed as ECU activity units (Example 1).

The following methods were used for evaluation of the effect of the enzyme preparations in biofinishing of cotton fabric: Weight loss of the treated fabrics was defined as percentage from weight of the fabric before and after the test (before weighing the fabrics were conditioning in a atmosphere of 21+2° C. and 50+5% RH). Evaluation of the surface cleaning effect of the enzyme treated fabrics was performed by a panel consisting of three persons. The fabrics were ranked on a score from 1 to 5, where 5 gave a clean surface. The Martindale Rubbing method (SFS-4328) was used for evaluation of pilling. Pilling was evaluated by a panel after 200 and 2000 cycles of abrasion (1=many pills, 5=no pills).

In Table III is shown that treatment of the cotton fabric with ALKO4237 and ALKO4467 cellulase preparations results in a good surface cleaning and marked reduction in the pilling tendency at both pH 5 and 7.

TABLE III

Weight loss, surface cleaning effect and pilling tendency of the cotton fabrics treated with neutral cellulases in Launder-Ometer.

| preparation | dosage ECU/g | time h | pH | weight loss % | surface cleaning effect | pilling 200 cycles | 2000 cycles |
|---|---|---|---|---|---|---|---|
| — | — | 1 | 5 | 0 | 1.0 | 1.0 | 1.0 |
| ALKO4237 | 200 | 1 | 5 | 2.3 | 3.5 | 4.0 | 3.8 |
| ALKO4237 | 400 | 1 | 5 | 3.2 | 3.5 | 4.0 | 3.8 |
| ALKO4467 | 200 | 1 | 5 | 1.2 | 2.5 | 3.7 | 3.4 |
| ALKO4467 | 400 | 1 | 5 | 1.9 | 2.8 | 3.7 | 3.4 |
| — | — | 2 | 5 | 0.1 | 1.0 | 1.0 | 1.0 |
| ALKO4237 | 200 | 2 | 5 | 4.4 | 4.0 | 4.2 | 4.1 |
| ALKO4237 | 400 | 2 | 5 | 6.0 | 4.3 | 4.2 | 4.3 |
| ALKO4467 | 200 | 2 | 5 | 3.0 | 3.5 | 4.0 | 3.8 |
| ALKO4467 | 400 | 2 | 5 | 4.0 | 3.8 | 4.0 | 3.9 |
| — | — | 1 | 7 | 0 | 1.0 | 1.0 | 1.0 |
| ALKO4237 | 200 | 1 | 7 | 2.5 | 3.0 | 3.7 | 3.5 |
| ALKO4237 | 400 | 1 | 7 | 3.8 | 4.0 | 4.0 | 3.9 |
| ALKO4467 | 200 | 1 | 7 | 0.8 | 2.0 | 3.5 | 3.3 |
| ALKO4467 | 400 | 1 | 7 | 1.4 | 2.0 | 3.6 | 3.7 |
| — | — | 2 | 7 | 0.1 | 1.0 | 1.2 | 1.1 |
| ALKO4237 | 200 | 2 | 7 | 4.8 | 4.0 | 3.8 | 4.0 |
| ALKO4237 | 400 | 2 | 7 | 6.0 | 4.3 | 4.0 | 4.3 |
| ALKO4467 | 200 | 2 | 7 | 2.2 | 2.5 | 4.0 | 3.4 |
| ALKO4467 | 400 | 2 | 7 | 3.0 | 3.3 | 3.8 | 3.7 |

Example 7

Use of the Neutral Cellulase-Containing Enzyme Preparations of the Invention in Biofinishing 7a. Use of Enzyme Preparations in the Biofinishing of Woven Fabric and Knit.

100% cotton woven fabric or 100% cotton knit are subjected to treatment with the cellulases of the invention (Example 1) in a semi-industrial drum washer (Esteri 20 HS-P). The treatment conditions are as follows:

A. Pretreatment (Only for Woven Fabrics)

60° C., 10 minutes, Ecostone A200 (Primalco Ltd, Biotec, Finland) 1 ml/l water.

B. Enzyme Treatment temperature 50-60° C., pH 7;

liquid ratio 5-20:1 (volume of liquid per weight of fabric);

treatment time 20-90 minutes, preferably 30-60 minutes; and enzyme dosage 50-900 nkat/g fabric or knit, preferably 200-600 nkat/g fabric or knit.

C. "After-Washing" Treatment

40° C., 10 minutes, alkaline detergent

D. Drying Treatment

The following standard methods are used for evaluation of the surface cleaning effect of enzyme preparations: The Martindale Rubbing Method (SFS-4328) and the Laundering Durability Test (SFS-3378). Treatment with the cellulase preparations of the invention results in a surface cleaning effect, an improvement in the softness and smoothness of the fabric and knit and a reduction in the pilling tendency.

7b. Use of Enzyme Preparations in the Finishing of Lyocell Fabrics and Knits.

The cellulase preparations of the invention can be used in fibrillation control and different finishing processes of 100% lyocell fabrics and knits and blends thereof. The following treatment conditions in semi-industrial drum washer (Esteri 20 HS-P) are used in order to create the peach effect on lyocell fabric:

A. Sodium carbonate 2.5 g/l; 60° C., treatment time of 60 minutes;

B. Rinse;

C. Enzyme treatment: temperature of 50-60° C., pH 7, liquid ratio 5-20:1, treatment time 40-120 minutes, preferably 45-90 minutes, and an enzyme dosage of 100-1500 nkat/g fabric, preferably 400-800 nkat/g fabric;

D. Aftertreatment; Alkaline detergent wash at 40° C. for 10 minutes;

E. Rinse; and

F. Dry.

The result is a peach skin effect.

Example 8

Use of Enzyme Preparations in Biostoning

Denim garments were subjected to treatment with the neutral cellulase preparations (Example 1) in a semi-industrial drum washer (Esteri 20 HS-P) to give the garments a stonewashed appearance. About 1.0 kg of denim garments (contained two different kinds of fabric) were used per machine load.

The treatment conditions were as follows.

A. Desizing. 100 liters water, 60° C., 10 minutes; 100 ml Ecostone A200 (Primalco Ltd, Biotec, Finland).

B. Cellulase Treatment. 100 liter water, 50° C., 45 minutes; 10 g Berol 08 (Berol Nobel AS, Sweden); 30 g citric acid+128 g $Na_2HPO_4 \times 2H_2O$ to give pH 7.

Neutral cellulase preparations were dosed as endoglucanase activity units (ECU, Example 1):

1. ALKO4237, 260 ECU/g of garment
2. ALKO4179, 260 ECU/g of garment
3. ALKO4124, 300 ECU/g of garment
4. ALKO4125, 250 ECU/g of garment C. Afterwashing. Alkaline detergent wash, 40° C., 10 minutes.

D. Drying.

The results were evaluated by visual appearance of the garments and by measuring the color as reflectance values with the Minolta Chroma Meter CM 1000R L*a*b system (Table IV). A good stonewashed effect was obtained with all these cellulase-treated garments. No backstaining (examined on the inside of the garment) could be seen visually in any of these cellulase-treated garments.

From the results of the color measurements shown in Table IV, it can be seen that the lightness and blueness units are clearly increased on the outside of the garments washed with the neutral cellulase preparations, showing a good stonewashed effect.

TABLE IV

Color Measurement of Denim Garments with Different Cellulase Preparations

| Source of Enzyme | Outside of the garment | | Inside of the garment | |
|---|---|---|---|---|
| | L | b | L | b |
| A. Fabric 1 | | | | |
| untreated | 24.1 | −8.5 | 57.1 | 0.17 |
| washed without cellulase | 21.4 | −14.0 | 54.5 | −4.3 |
| ALKO4237 | 26.7 | −17.3 | 56.5 | −4.9 |
| ALKO4179 | 26.8 | −17.0 | 56.3 | −4.5 |
| ALKO4125 | 28.0 | −17.4 | 57.8 | −4.1 |
| ALKO4124 | 26.4 | −17.5 | 57.1 | −4.8 |
| B. Fabric 2 | | | | |
| untreated | 22.5 | −8.3 | 57.6 | 0.66 |
| ALKO4237 | 25.0 | −16.3 | 56.1 | −4.3 |
| ALKO4179 | 25.0 | −15.8 | 55.4 | −4.4 |
| ALKO4125 | 26.7 | −17.0 | 56.8 | −4.0 |
| ALKO4124 | 25.6 | −17.0 | 56.4 | −4.0 |

L = Lightness unit of garment after the treatment (the higher the value, the lighter the garment).
b = Blueness unit of garment after the treatment (the more negative value, the more blueing in the garment).

Example 9

Purification of Neutral Cellulases

Concentrated growth medium from ALKO4237 was fractionated at 7° C. on DEAE Sepharose CL6B with a linear gradient from zero to 0.5 M NaCl in 25 mM Tris/HCl pH 7.2. Four peaks of endoglucanase activity at pH 4.8 were found. Peak I, containing about 10% of the recovered ECU, eluted at about 150 mM NaCl, Peak II (about 30% of ECU) at 230 mM NaCl, Peak III (about 20% of ECU) at 270 mM NaCl and Peak IV (about 40% of ECU) at 320 mM NaCl. Table V shows the results when these peaks were tested for their utility in biostoning at neutral pH and 50° C.

These results show that on both an ECU basis and a total protein basis, Peak II was more effective than any other peak or than the unfractionated concentrate. A mixture of Peaks I and II containing 70 ECU of each/g denim was also tested. This resulted in an L (right) value of 7.3 and b (reverse) of 2.5. Thus, this mixture was more effective than either peak alone.

The purification procedure was scaled up to obtain homogenous samples of some of the desired proteins in these peaks. Concentrated ALKO4237 growth medium (4.5 liters) was fractionated with ammonium sulphate. The proteins that precipitated between 17 g and 42 g of ammonium sulphate per 100 ml of concentrate were suspended in 0.9 liter of 25 mM Tris/HCl pH 7.2 containing 0.25 mM EDTA and then diluted with water to a conductivity of 4 mS/cm and adjusted with 1M NaOH to pH 8.0. The resulting solution (about 45 liters) was pumped at 150 ml/min through a 6.3 liter column of DEAE-Sepharose FF™ at room temperature. Peak I endoglucanase activity did not bind under these conditions. Bound proteins were eluted at 110 ml/min with a linear gradient from 0.0 to 0.5 M NaCl in 20 liters of 25 mM Tris/HCl pH 7.7 containing 0.25 mM EDTA. Peak II endoglucanase eluted at about 14 mS/cm. Instead of the separate Peaks III and IV seen with small scale separations in DEAE in the cold room, a single peak, called Peak III/IV, eluted at about 25 mS/cm.

TABLE V

Indigo Dye Release by DEAE-Sepharose ™ Pools in Neutral Conditions

| | ADDITION | | | | | | | | |
|---|---|---|---|---|---|---|---|---|---|
| | None | Concentrate | Peak I | | Peak II | | Peak III | | Peak IV |
| ECU/g | 0 | 100 | 200 | 310 | 185 | 340 | 97 | 260 | 95 | 190 |
| mg/g | 0 | 10 | 20 | 41 | 9 | 26 | 24 | 46 | 5 | 10 |
| L (right) | 2.9 | 5.2 | 7.0 | 5.5 | 7.3 | 10.3 | 4.4 | 5.8 | 3.9 | 4.3 |
| b (reverse) | 0.4 | 2.6 | 3.5 | 3.5 | 2.9 | 2.5 | 0.9 | 1.4 | 0.1 | 0.5 |

The parameter L (right) indicates the lightening of the right side of the blue denim, and b (reverse) indicates the blueing of the reverse side (i.e., backstaining). The fabric was washed in the LP-2 Launder-Ometer and then measured with the Minolta ChromaMeter, as described in Example 3, except that no Berol was used and the buffer that was used was 0.05 M McIlvaine pH 7 (see Data for Biochemical Research, Dawson, R., et al., eds., 1969, Oxford Univ. Press). The dosage is shown as both ECU/g of denim and mg protein/g of denim.

Figure 8:
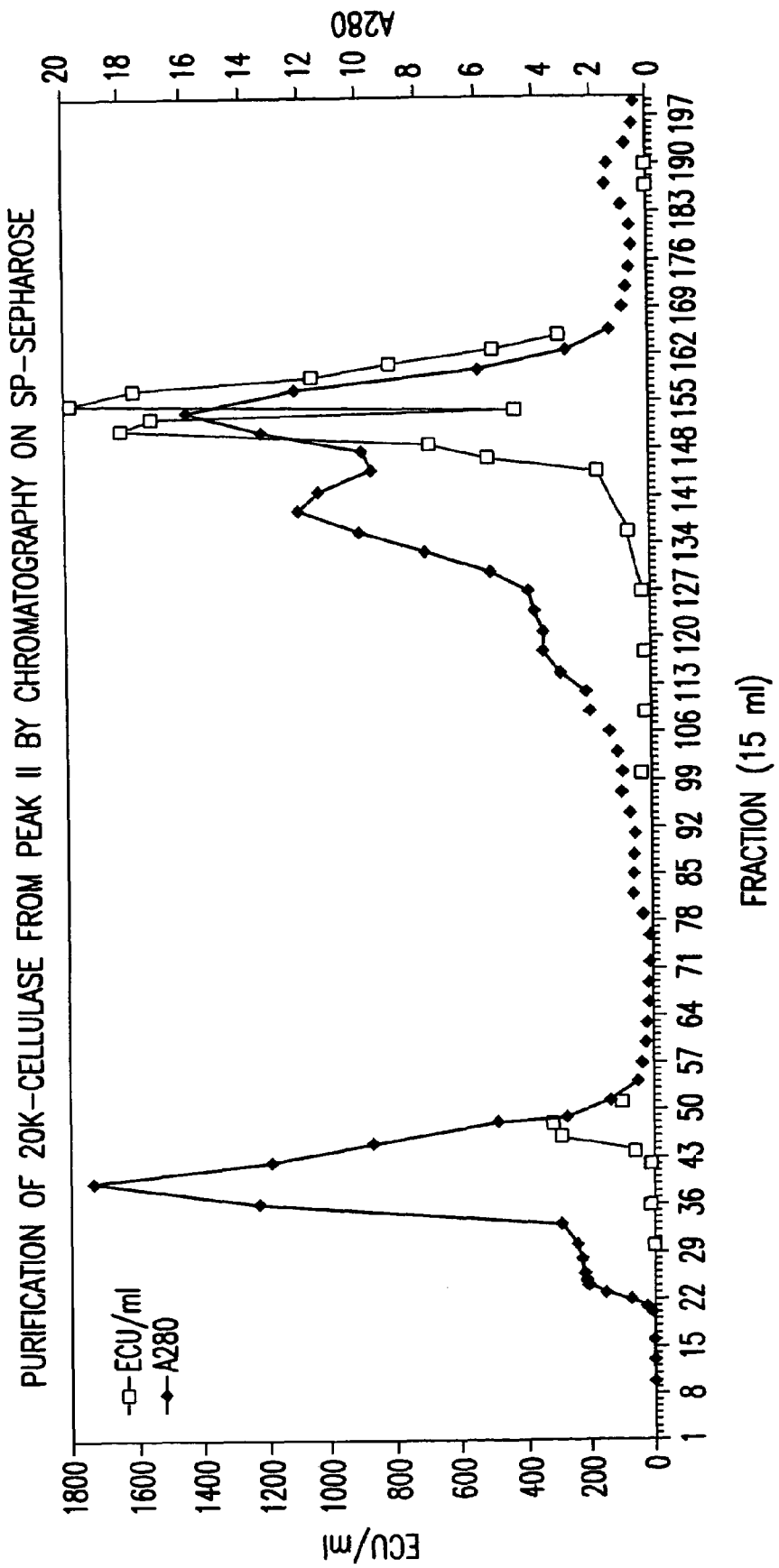
FIG. 8 shows the purification of 20K-cellulase from Peak II by chromatography on SP-Sepharose™. A sample containing 11.7 g of protein and 576,000 ECU was applied to a 4.5×31 cm column, which was developed as described in Example 9. Fractions of 15 ml were collected. Endoglucanase activities in the peak at fractions 148-161 are underestimated because crystallization occurred before the enzyme could be sufficiently diluted for assay. Crystalline material from these fractions contained 486,000 ECU.
Figure 9A:
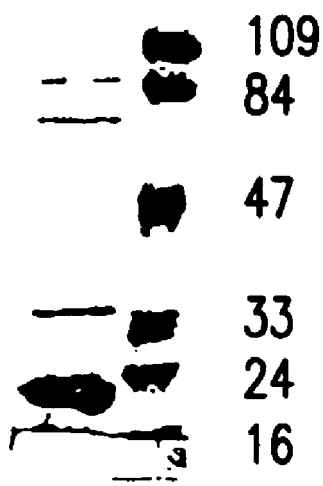
FIGS. 9 (A and B) show SDS-PAGE analysis of the 20K-cellulase. The molecular masses of the standards are shown in kDa.
Figure 9B:
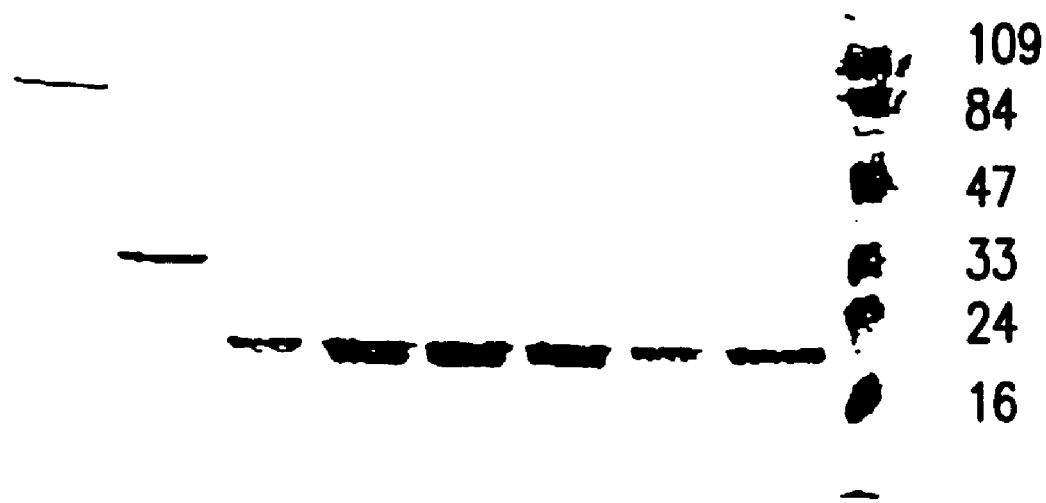

Proteins in Peak II (3.5 liters) were precipitated with ammonium sulphate (450 g/liter) and suspended in 170 ml 25 mM PIPES/KOH pH 6.0 containing 1 mM EDTA. Portions of this material were transferred to 25 mM sodium acetate pH 4.0 containing 1 mM EDTA by gel-filtration on a 5×29 cm column of G25 Sephadex™ (coarse) and then fractionated on SP-Sepharose™. FIG. 8 shows the result that was obtained when 11.7 g of these proteins was applied to a 4.5×31 cm column of SP-Sepharose™ in 25 mM sodium acetate pH 4.0 containing 1 mM EDTA at 150 ml/h and the column developed at 75 ml/h with a linear gradient from 0.0 to 0.4 M NaCl in 3.4 liters of the same buffer. Most of the endoglucanase eluted at 0.2 M NaCl. The modified assay described in Example 10 was used. When active fractions were stored at 7° C., a crystalline precipitate appeared in them and contained nearly all the endoglucanase activity. Active fractions (15 ml) in which crystallization was slow, were induced to form crystals by seeding with 30 µl of suspension from fractions already containing crystals. After 2 to 3 days, the crystals were collected by centrifugation, washed with 25 mM PIPES/KOH pH 6.0 containing 1 mM EDTA and disolved in 25 mM Tris/HCl pH 7.2 containing 0.25 mM EDTA. Analysis by SDS-PAGE showed the washed crystals contained a virtually homogenous protein with an apparent molecular mass close to 20 kDa (the error in SDS-PAGE estimations of molecular mass is at least±10%, and may be much greater for unusual proteins). This protein is called the 20K-cellulase. Contaminating protein could also be removed by gel-filtration on G50 Sephadex™ in 50 mM PIPES/KOH pH 6.0 containing 1 mM EDTA. An example of this is shown in FIG. 9, where unwashed crystals were purified by gel-filtration. The endoglucanase activity co-eluted with the 20 kDa protein well after the cytochrome c (11.2 kDa) volume, showing that this 20 kDa protein is abnormally retarded by interaction with Sephadex™.

Proteins in Peak III/IV were precipitated with ammonium sulphate and transferred to 25 mM sodium acetate pH 4.0 containing 1 mM EDTA in the same way as described for the Peak II proteins. Upon transfer to 25 mM sodium acetate pH 4.0, a large precipitate formed and was discarded. The active supernatant was fractionated on SP-Sepharose™. At low protein loading (e.g. 200 mg protein to a 2.5×11 cm column as shown in FIG. 10, most of the endoglucanase activity bound to the column and was eluted with a NaCl gradient at about 50 mM NaCl. This active peak was followed by a second peak of inactive protein.

SDS-PAGE analysis showed that the active and inactive peaks both contained several proteins, including proteins with apparent molecular masses close to 50 kDa that could not be distinguished from each other by SDS-PAGE. Both peaks were further purified by chromatography on Phenyl Sepharose™.

The active fractions (fractions 15 to 18 in FIG. 10) were pooled, adjusted to 50 mM PIPES/KOH pH 6.0 (by addition of 0.25 M PIPES/KOH pH 6.0) and 15 g % ammonium sulphate (by addition of solid ammonium sulphate) and applied to a 1.5×8.5 cm column of Phenyl Sepharose™ equilibrated with 25 mM PIPES/KOH pH 6.0 containing 1 mM EDTA and 15 g % of ammonium sulphate. The column was developed with a linear gradient from 15 to 0 g % ammonium sulphate in 104 ml of 25 mM PIPES/KOH pH 6.0. After the end of the gradient, the column was further washed with 25 mM PIPES/KOH pH 6.0. Two protein peaks eluted on the gradient, first a small peak of inactive protein and then a major peak containing most of the endoglucanase activity. SDS-PAGE analysis (FIG. 11A and B) showed that both peaks contained essentially homogenous proteins with apparent molecular masses close to 50 kDa (i.e., they migrate slightly slower than the BioRad prestained ovalbumin standard, which has an apparent molecular mass of 47 kDa). These two proteins could not be distinguished by the inventors' SDS-PAGE analyses, even when they were run together as mixtures. The protein in the active peak was called 50K-cellulase and the protein in the inactive peak was called 50K-protein B. Larger amounts of 50K-cellulase B were obtained by fractionation of the second (and inactive) peak eluted from SP-Sepharose™ (fractions 19 to 23 in FIG. 10) on Phenyl Sepharose™ in exactly the same way as described above for the active fractions.

Production of still larger amounts of 50K-cellulase and 50K-cellulase B was facilitated by overloading the SP-Sepharose™ column. For example, when 15 g of protein was applied to a 4.5×31 cm column of SP-Sepharose™, instead of binding to the column, the 50K-cellulase was apparently displaced by more strongly bound proteins, and eluted before the NaCl gradient. This material was already highly purified, and homogenous 50K-cellulase was isolated from it by chromatography on Phenyl Sepharose™ as described above.

In order to speed up the purification of larger amounts of 50K-cellulase the SP-Sepharose and Phenyl, Sepharose columns were reversed. After adjusting the ammonium sulphate concentration to about 15 g %, the proteins precipitated in Peak III/IV were applied into Phenyl Sepharose as described before. With high overloading (e.g. 17 g of protein applied to a 3.2×25 cm column of Phenyl Sepharose) most of the total protein ran through the column, but 50K-cellulase (containing most of the endoglucanase activity) was bound and eluted at the end of linear gradient from 15 to 0 g % of ammonium sulphate in 25 mM PIPES/KOH pH 6.0. Western analysis with a rabbit antiserum recognizing 50K-cellulase B showed that the 50K-cellulase B eluted just before 50K-cellulase. Further purification was achieved by fractionation on SP-Sepharose as described earlier. In this reversed order of SP-Sepharose and Phenyl Sepharose the proteins in Peak III/IV precipitated with ammonium sulphate could be applied directly to the next purification step without removing salt. The large protein precipitate, which appeared upon transfer of the concentrated proteins in Peak III/IV directly into 25 mM sodium acetate pH 4.0 for SP-Sepharose, could also be avoided this way. As the 50K-cellulase only just binds to SP-Sepharose, the preceeding fractionation on Phenyl Sepharose markedly reduced the apparently interfering total protein load on SP-Sepharose.

50K-cellulase and 50K-cellulase B were each tested in the Launder-Ometer to see if they are responsible for the beneficial effects of Peak IV reported in Example 10. Both proteins were found to have beneficial effects (Table VI). At the low concentrations used in this experiment, they did not themselves increase the release of indigo dye from the outer face of the denim (i.e., $L_{right}$ did not increase) but they effectively decreased the back-staining of dye onto the inner face of the denim ($L_{reverse}$ became more positive and $b_{reverse}$ became smaller) especially when used together with 20K-cellulase.

The 20K-cellulase performed well in Launder-Ometer tests at pH 5 as well as at pH 7. At pH 5, 0.2 mg of 20K-cellulase per g of denim increased $L_{right}$ from 3.2 to 5.2. Addition of 50K-cellulase at 0.1 mg per gram of denim together with the 20K-cellulase also decreased the back-staining at pH 5 ($L_{reverse}$ and $b_{reverse}$ changed from 0.0 and 2.6 with 20K-cellulase alone to 1.3 and 1.5, respectively, with the mixture of 20K- and 50K-cellulases).

TABLE VI

Indigo Dye Release by 20K-cellulase, 50K-cellulase and 50K-cellulase B

| Sample | Dose (mg/g) | $L_{right}$ | $L_{reverse}$ | $b_{reverse}$ |
|---|---|---|---|---|
| Buffer alone | — | 2.8 | −0.6 | 1.6 |
| 20K-cellulase | 0.18 | 5.6 | −1.0 | 4.0 |
|  | 0.09 | 4.8 | −1.5 | 3.3 |
| 50K-cellulase | 0.15 | 2.6 | −0.3 | 1.0 |
|  | 0.075 | 3.0 | 0.4 | 1.3 |
| 50K-cellulase B | 0.31 | 2.8 | 1.3 | 0.8 |
|  | 0.15 | 2.7 | 1.5 | 0.5 |
| 20K-cellulase + 50K-cellulase | 0.18 + 0.075 | 5.6 | 0.3 | 2.5 |
|  | 0.09 + 0.075 | 5.1 | 0.3 | 2.1 |
| 20K-cellulase + 50K-cellulase B | 0.18 + 0.15 | 4.7 | 0.0 | 3.0 |

Conditions were the same as in Table V. The dose is shown as mg protein per gram of denim.

Example 10

Properties of the 20K-Cellulase

Although polyclonal antibodies prepared against cellulases purified from *Trichoderma reesei* (designated anti-EGI, anti-CBHI and anti-CBHII antibodies) recognized proteins in the ALKO4237 growth medium, there was only a very weak cross-reaction with pure 20K-cellulase under the same conditions of Western blot analysis.

When growth medium from ALKO4237 was probed on Western analysis with antiserum raised in rabbits against pure 20K cellulase, a strong band at about 35 kDa was observed in addition to the 20 kDa band. No apparent endoglucanase activity could be detected for this 35 kDa protein. Also, a weaker band was seen immediately ahead of the 20 kDa band (FIG. 14).

ALKO4124 gave an almost identical pattern as ALKO4237, indicating that this and other fungi probably contain cellulases very similar to the 20K-cellulase of the present invention.

Amino acid sequences of tryptic peptides derived from 20K-cellulases are shown in FIG. 17. Sequence #429 corresponds to SEQ ID NO: 1; sequence #430 corresponds to SEQ ID NO: 2; sequence #431 corresponds to SEQ ID NO: 3; sequence #432 corresponds to SEQ ID NO: 4; sequence #433 corresponds to SEQ ID NO: 5; sequence #439 corresponds to SEQ ID NO: 6; fr 9 corresponds to SEQ ID NO: 7; fr 14 corresponds to SEQ ID NO: 8; fr 16 corresponds to SEQ ID NO: 9; fr 17 corresponds to SEQ ID NO: 10; ft 28 corresponds to SEQ ID NO: 11 and ft 30 corresponds to SEQ ID NO: 12.

Purified 20K-cellulase performed well in biostoning at neutral pH without the addition of other enzyme activities as shown in Table VII.

TABLE VII

Biostoning by Purified 20K-cellulase

| Addition | Dosage | $L_{right}$ | $b_{right}$ | $L_{reverse}$ | $b_{reverse}$ |
|---|---|---|---|---|---|
| Buffer | 0.0 | 3.6 | 0.1 | 0.5 | 0.6 |
| 20K | 0.72 | 8.9 | 2.9 | −1.1 | 4.7 |
| 20K | 0.25 | 6.0 | 2.3 | −0.5 | 3.6 |
| 20K | 0.07 | 5.3 | 1.7 | −0.4 | 2.9 |
| Whole medium | 20 | 6.1 | 2.8 | −2.9 | 5.5 |

Conditions were as in the experiment shown in Table V. Dosage is shown as mg protein/g denim fabric. "Whole medium" indicates the unfractionated ALKO4237 concentrated growth medium.

Compared to the unfractionated medium, 20K-cellulase resulted in the same degree of lightening ($L_{right}$=6.0-6.1) at 1/80th the protein dosage. Further, there was less backstaining onto the reverse side face of the fabric ($L_{reverse}$=0.5 compared to −2.9 and $b_{reverse}$=3.6 compared to 5.5). Fabric treated with 20K-cellulase had an agreeable soft texture.

Although 20K-cellulase performed surprisingly well without other additions, even better fabric appearance and texture resulted when 20K was used together with the DEAE-Sepharose pools I, III or IV (Table VIII).

TABLE VIII

Synergy in Biostoning Between 20K-cellulase and Endoglucanase Pools Eluted from DEAE-Sepharose

| Addition | Dosage | $L_{right}$ | $b_{right}$ | $L_{reverse}$ | $b_{reverse}$ |
|---|---|---|---|---|---|
| Buffer | 0.0 | 3.8 | 0.2 | −0.7 | 1.5 |
| 20K | 0.18 | 5.8 | 2.3 | −2.2 | 5.5 |
| Pool I | 15 | 5.1 | 1.9 | −3.1 | 5.7 |
| Pool III | 47 | 5.2 | 1.6 | −0.1 | 2.6 |
| Pool IV | 14 | 5.6 | 0.9 | 0.4 | 1.8 |
| 20K + Pool I | 15.18 | 7.1 | 2.8 | 0.7 | 3.3 |
| 20K + Pool III | 47.18 | 7.6 | 3.1 | −1.7 | 5.3 |
| 20K + Pool IV | 14.18 | 8.6 | 2.6 | 0.8 | 3.2 |
| Whole medium | 20 | 5.7 | 2.4 | −4.1 | 5.9 |

Conditions were as in Table V.

The mixtures of 20K-cellulase with Pools I, III and IV caused more lightening (increased $L_{right}$) than either component alone. At least for the combination of 20K-cellulase with Pool IV, it is clear that this is because of synergy and not merely an additive effect. Further, the backstaining with all mixtures was actually less ($L_{reverse}$ more positive, $b_{reverse}$ less) than the backstaining observed with 20K-cellulase alone. The combination of 20K with Pool IV was particularly effective. Pool IV contains many proteins, one of which (a 50 kDa polypeptide) copurifies with endoglucanase activity during chromatography of Pool IV on Sephadex G100 and S-Sepharose. While good biostoning is achieved with 20K-cellulase alone, better results are possible with 20K-cellulase plus one or more proteins purified from Pool IV. Biostoning with mixtures of the 20K-cellulase and the 50K-cellulase and the 50K-cellulase B purified from Pool III/IV have already been presented (Table VI in Example 9).

Therefore, the present invention is not limited to the use of only the 20K-cellulase. Other proteins in the ALKO4237 medium are useful alone or in suitable combinations.

In the standard endoglucanase assay described by Bailey et al. (1981, loc. cit.), the enzyme amount is chosen that produces, in 10 min and pH 4.8 (0.05 M Na-citrate buffer), about 0.6 mM reducing equivalents from 1% hydroxyethylcellulose, resulting in a final absorbance change ($\Delta A_{540}$) of between 0.2 and 0.25. This far exceeds the range in which $\Delta A_{540}$ is proportional to the amount of 20K-cellulase.

Therefore, the procedure was modified as follows. Enough enzyme was used to produce about 0.2 mM reducing equivalents in 10 min in 0.05 M HEPES buffer (pH 7.0). To reach the threshold concentration of reducing equivalents above which color is formed in the DNS system, 0.12 mM glucose was freshly added to the stock DNS reagent. This method (called the "modified" method) was used when characterizing the endoglucanase activity of the 20K-cellulase and also the 50K-cellulase. With 1% hydroxyethylcellulose as substrate, the range in which $\Delta A_{540}$ is proportional to the amount of 20- and 50K-cellulase is relatively narrow, and so 2% carboxymethylcellulose was taken as an alternative substrate. With 2% carboxymethylcellulose, the range of linear correlation between $\Delta A_{540}$ and the amount of 20K- and 50K-cellulase was broader than with 1% hydroxyethylcellulose. The endoglucanase activity determined with 2% carboxymethylcellulose was about 8-10-fold for 20K-cellulase and about 50-fold for 50K-cellulase compared with that determined with 1% hydroxyethylcellulose.

No activity of 20K-cellulase was detectable for 4-methylumbelliferyl-β-D-lactoside, a characteristic substrate of cellobiohydrolases. The activity towards filter paper was also very low, but detectable.

The 20K-cellulase was relatively heat stable. It was incubated at 7 μg/ml and 100° C. in 25 mM Tris-HCl, 0.2 mM EDTA, for 30 or 60 min. and then assayed at pH 7.0 and 50° C. 52% and 35% respectively, of the endoglucanase activity remained at pH 7.2. 40% and 22%, respectively, remained at pH 8.8. (These pH values were measured at room temperature; the actual pH at 100° C. is somewhat lower.) At 80° C., pH 7.2, 70% of the activity remained for 60 min.

These results indicate that the enzyme is suitable for applications in which it may be (e.g., accidentally) exposed to elevated temperatures. As well as being resistant to irreversible inactivation at high temperatures, the enzyme exhibited an optimum temperature of 70° C. during 10 min. assays at pH 7.0 (FIG. 15). The decreased activity observed above 70° C. was mainly due to a reversible change in enzyme conformation: the enzyme recovered most of its activity when returned to 50° C.

Figure 16A:
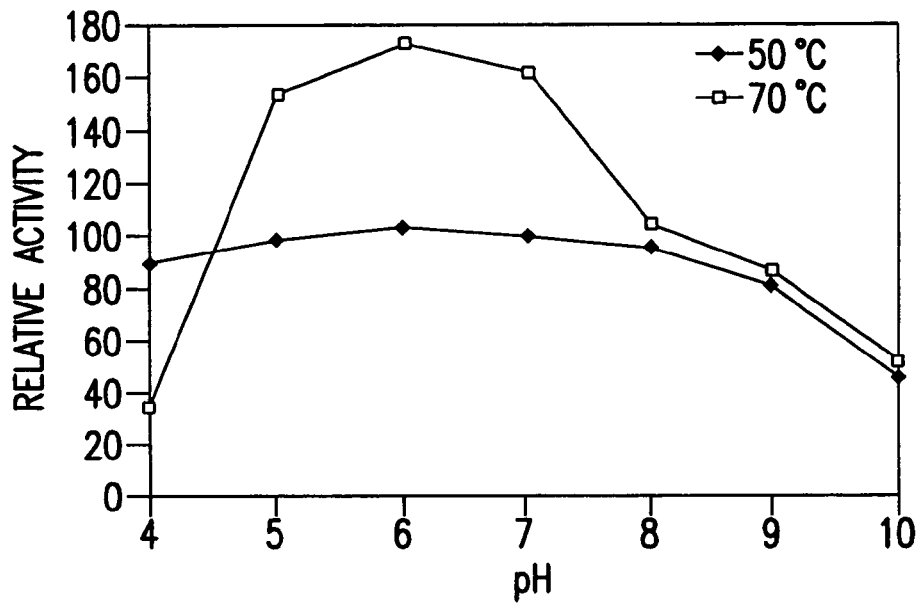
Figure 16B:
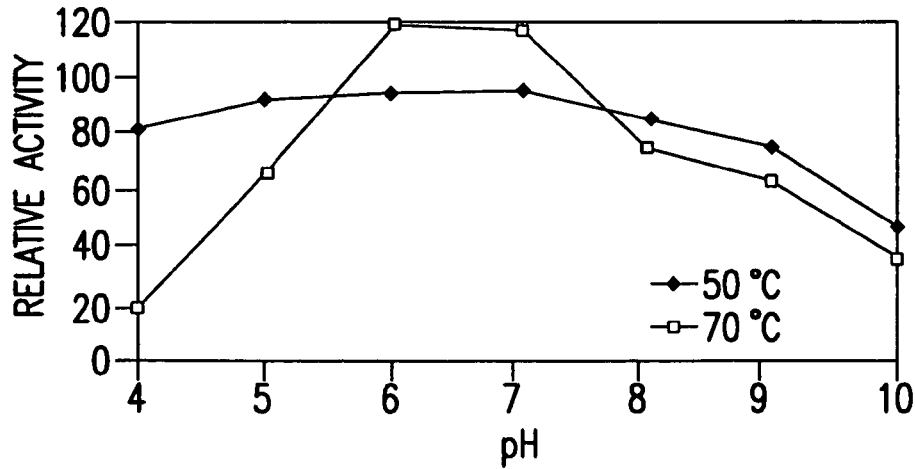

At 50° C., the 20K-cellulase exhibited 80% or more of its maximum activity throughout the pH range 4 to 9, and nearly 50% at pH 10. This was the case in both 10 min. (FIG. 16A) and 60 min. (FIG. 16B) assays. These figures also show the pH dependence of the enzyme at 70° C. With 10 min. assays, the enzyme was more active at 70° C. than it was at 50° C. over the range pH 4.5 to 8 and about equally active at pH 10 (FIG. 16A). With 60 min. assays (i.e., approaching commercial conditions), the enzyme was more active at 70° C. can it was at 50° C. between pH 5.5 and 7.5. However, it was only slightly less active at 70° C. than at 50° C. up to pH 10. In practice, this means that the enzyme can be used equally well over a wide range of pH and at temperatures up to at least 70° C.

Example 11

Properties of the 50K-Cellulase

Pure 50K-cellulase had both endoglucanase activity (against hydroxyethylcellulose) and cellobiohydrolase activity (against 4-methylumbelliferyl-β-D-lactoside, assayed essentially as described by van Tilbeurgh et al, in *Methods in Enzymology* [1988] vol. 160, pp 45-59). A sample of the pure enzyme with an $A_{280}$ of 1.8 contained 2030 ECU/ml and 300 PCU/ml at pH 7.0 and 50° C. (one PCU is the amount of activity that liberates 1 nmol of methylumbelliferone per second).

In Western analyses, 50K-cellulase was strongly recognized by antiserum (KH 1057) raised against endoglucanase I of *T. reesei*, but only weakly by antisera (KH 1050 and KH 1053, respectively) against cellobiohydrolases I and II of *T. reesei*. It was not recognized by the antiserum raised against 20K-cellulase (FIG. 14). When the growth medium of ALKO 4237 was probed in Western analyses with rabbit antiserum raised against 50K-cellulase itself, only one obvious band (which had a molecular mass between 33 and 47 kDa) was seen in addition to the very strong band at about 50 kDa.

The apparent molecular mass of 50K-cellulase by SDS-PAGE decreased by about 2 to 5 kDa when the protein was treated with endoglycosidase $H_f$, indicating that the enzyme contains carbohydrate removable by this endoglycosidase.

50K-cellulase was unusually resistant to tryptic digestion, indicating that it has an unusually stable structure. However, it was cleaved by treatment with cyanogenbromide, and the resulting fragments could then be digested with trypsin or with lysylendopeptidase C. Sequences of some of the peptides so obtained are shown in Table IX.

TABLE IX

Sequences of peptides isolated from the 50 K-cellulase (uncertain residues in lower case)

| | | |
|---|---|---|
| #507 | (SEQ ID NO: 13) | VYLLDETEHR |
| #509 | (SEQ ID NO: 14) | XXLNPGGAYYGT |
| #563 | (SEQ ID NO: 15) | MsEGAECEYDGVCDKDG |
| #565 | (SEQ ID NO: 16) | NPYRVXITDYYGNS |
| #603 | (SEQ ID NO: 17) | DPTGARSELNPGGAYYGTGYXDAQ |
| #605 | (SEQ ID NO: 18) | XXVPDYhQHGVda |
| #610 | (SEQ ID NO: 19) | NEMDIXEANSRA |
| #611 | (SEQ ID NO: 20) | LPXGMNSALYLSEMDPTGARSELNP |
| #612 | (SEQ ID NO: 21) | VEPSPEVTYSNLRXGEIXgXF |
| #619 | (SEQ ID NO: 22) | DGCGWNPYRVvITtDYYnN |

TABLE IX-continued

Sequences of peptides isolated from the
50 K-cellulase (uncertain residues in
lower case)

620 (SEQ ID NO: 23)    LPCGMXSALY

621 (SEQ ID NO: 24)    ADGCQPRTNYIVLDdLIHPXXQ

The 50K-cellulase is a stable enzyme that exhibits endoglucanase activity over a wide range of pH values and at high temperatures, so it is suitable for use in many industrial conditions. At pH 7.0 and with 60 min reaction times, it has an optimum temperature between 65 and 70° C., and even with this long reaction time still exhibits, at 75° C., 50% of the activity observed at 50° C. (FIG. 12).

With 60 min reaction times, the pH optimum was very broad at 50° C., with essentially constant activity between pH 4.4 and 7.0, and activities at pH 9 and 10 equal to 50% and 30%, respectively, of that at pH 7.0. At 70° C., there was a clear optimum at pH 6, and, between pH 5 and 7, the activity (with 60 min reaction times) was 3-fold or more greater than that at 50° C. However, at pH 4.4 and pH values above 8, the activity was greater at 50° C. than at 70° C. (in 60 min assays), suggesting that the stability of the enzyme decreases at 70° C. right side the pH range 5 to 7.5. The pH-dependence is illustrated in FIG. 13.

Example 12

Properties of 50K-Cellulase B

No detectable endoglucanase activity could be measured for the 50K-cellulase B (previously called 50K-protein B) with hydroxyethylcellulose or carboxymethylcellulose. At acidic pH, the 50K-cellulase B had a low cellobiohydrolase activity, which (measured with 4-methylumbelliferyl-β-D-lactoside) at pH 5 was less than 0.1% of that of the 50K cellulase. In addition, the 50K-cellulase B had a detectable activity towards filter paper at pH 4.8 and acid swollen, amorphic Solca Floc-cellulose at pH 5 and 7 used in enzyme activity determinations.

In Western analyses, 50K-cellulase B was strongly recognized by antiserum (KH1050) raised against cellobiohydrolase I of *T. reesei*, but only weakly by antisera against cellobiohydrolase II or endoglucanase I of *T. reesei* or against the 50K-cellulase. It was not recognized by antiserum raised against the 20K-cellulase (FIG. 14). Table X shows sequences of peptides isolated from 50K-cellulase B.

TABLE X

Sequences of peptides isolated from the
50 K-cellulase B (uncertain residues
in lower case)

534 (SEQ ID NO: 25)    vGNPDFYGK

535 (SEQ ID NO: 26)    FGPIGSTY

631 (SEQ ID NO: 27)    LSQYFIQDGeRK

TABLE X-continued

Sequences of peptides isolated from the
50 K-cellulase B (uncertain residues
in lower case)

632 (SEQ ID NO: 28)    FTVVSRFEENK

636 (SEQ ID NO: 29)    HEYGTNVGSRFYLMNGPDK

Example 13

Stability of Neutral Cellulases in Different Detergents

Stability of the neutral cellulase preparations were tested in three different detergent solutions. The detergent solutions were OMO® Total (or OMO® Neste, Lever UK), OMO® Color (Lever S.A.) and Colour Detergent Liquid (Unilever, The Netherlands). The tested cellulase preparations were ALKO4125, ALKO4179, ALKO4237 and ALKO4265 (Example 1) concentrated culture filtrates and purified 20K- and 50K-cellulases from the ALKO4237 strain (Example 9).

Cellulase preparations were incubated at 40° C. in 0.25% detergent solutions. The activity against hydroxyethylcellulose (ECU/ml, Example 1) was measured (pH 7, 50° C.) from samples taken after 5-30 minutes incubation.

The tested preparations were as follows:

Culture Filtrates:
ALKO4125: 780 ECU/ml (pH 7, 50° C.)
ALKO4179: 830 ECU/ml
ALKO4265: 760 ECU/ml
ALKO4237: 650 ECU/ml Purified Proteins:
20K-cellulase: 9423 ECU/ml
50K-cellulase: 10100 ECU/ml The results are shown in Tables XI-XIII.

ALKO4179, ALKO4265 and ALKO4237 cellulase preparations and 20K- and 50K-cellulases stay almost 100% stable for 30 minutes at 40° C. in all three tested detergents. ALKO4125 stays stable for 30 minutes at 40° C. in Colour Detergent Liquid and in OMO® Neste.

TABLE XI

Stability of different cellulases in 0.25% Colour Detergent Liquid
(pH 7.5-7.9).

| preparation | enzyme dosage % (ml) | pH* | % of activity left | | | | |
|---|---|---|---|---|---|---|---|
| | | | 0' | 5' | 10' | 20' | 30' |
| Culture filtrates: | | | | | | | |
| ALKO4125 | 6 | 7.3 | 100 | 97 | 98 | 98 | 99 |
| ALKO4179 | 6 | 7.1 | 100 | 99 | 100 | 100 | 10 |
| ALKO4265 | 6 | 7.2 | 100 | 100 | 100 | 100 | 100 |
| ALKO4237 | 6 | 7.1 | 100 | 100 | 82 | 95 | 100 |
| Purified proteins from ALKO4237: | | | | | | | |
| 20K-cellulase | 1 | 7.8 | 100 | 98 | 99 | 97 | 100 |
| 50K-cellulase | 1 | 7.6 | 100 | 100 | 100 | 100 | 100 |

*pH of the 0.25% detergent + enzyme solution after 30' incubation

TABLE XII

Stability of different cellulases in 0.25% OMO ®
Total (or OMO ® Neste pH 8.5).

| preparation | enzyme dosage % (ml) | pH* | 0' | 5' | 10' | 20' | 30' |
|---|---|---|---|---|---|---|---|
| Culture filtrates: | | | | | | | |
| ALKO4125 | 6 | 7.8 | 100 | 98 | 96 | 86 | 87 |
| ALKO4179 | 6 | 7.3 | 100 | 98 | 96 | 96 | 99 |
| ALKO4265 | 6 | 7.1 | 100 | 100 | 100 | 100 | 100 |
| ALKO4265 | 4 | 7.8 | 100 | 99 | 97 | 100 | 100 |
| ALKO4237 | 4 | 7.8 | 100 | 100 | 100 | 99 | 100 |
| ALKO4237 | 2 | 7.3 | 100 | 99 | 97 | 99 | 99 |
| Purified proteins from ALKO4237: | | | | | | | |
| 20K-cellulase | 1 | 8.2 | 100 | 100 | 99 | 93 | 100 |
| 50K-cellulase | 1 | 7.8 | 100 | 95 | 92 | 95 | 94 |

*pH of the 0.25% detergent + enzyme solution after 30' incubation

TABLE XIII

Stability of different cellulases in 0.25% OMO ® Color
(pH 9.6-10)

| preparation | enzyme dosage % (ml) | pH* | 0' | 5' | 10' | 20' | 30' |
|---|---|---|---|---|---|---|---|
| Culture filtrates: | | | | | | | |
| ALKO4125 | 6 | 9.6 | 100 | (15) | (15) | (13) | (14) |
| ALKO4179 | 6 | 8.3 | 100 | 97 | 100 | 97 | 99 |
| ALKO4265 | 6 | 9.1 | 100 | 100 | 100 | 100 | 100 |
| ALKO4265 | 4 | 8.5 | 100 | 93 | 95 | 99 | 98 |
| ALKO4237 | 4 | 8.5 | 100 | 98 | 96 | 96 | 99 |
| ALKO4237 | 2 | 9.1 | 100 | 93 | 95 | 99 | 98 |
| Purified proteins from ALKO4237: | | | | | | | |
| 20K-cellulase | 1 | 9.8 | 100 | 99 | 100 | 100 | 100 |
| 50K-cellulase | 1 | 8.9 | 100 | 100 | 100 | 100 | 100 |

*pH of the 0.25% detergent + enzyme solution after 30' incubation

Example 14

Function of Neutral Cellulases in Detergents in HEC Substrate

The function of different neutral cellulases in detergents was determined by using hydroxyethylcellulose (HEC) as a substrate. The tested cellulase preparations were ALKO4265 and ALKO4237 concentrated culture filtrates and purified 20K- and 50K-cellulases from ALKO4237 strain. HEC substrates were prepared by dissolving 1% HEC into 0.25% detergent solutions. By using these substrates the activity against HEC (ECU/ml) was measured at 40° C. from each cellulase preparations as described in Example 1. Detergents and cellulase preparations used in these experiments are described in Example 13.

pH of the substrates:

| HEC/buffer | pH 7 |
|---|---|
| HEC/Colour Detergent Liquid | pH 7.5 |
| HEC/OMO ® Total | pH 7.8 |
| HEC/OMO ® Color | pH 9.7 |

TABLE XIV

ECU of the cellulase preparations in different detergents
(compared as % from the ECU activity measured in pH 7 buffer)

| preparation | Activity % | | | |
|---|---|---|---|---|
| | ECU/ buffer | ECU/ col.det.liquid | ECU/ OMO ® Total | ECU/ OMO ® Color |
| culture filtrates: | | | | |
| ALKO4265 | 100 | 89 | 96 | 59 |
| ALKO4237 | 100 | 97 | 95 | 40 |
| purified proteins: | | | | |
| 20K-cellulase | 100 | 100 | 93 | 81 |
| 50K-cellulase | 100 | 92 | 79 | 46 |

ALKO4237 and ALKO4265 cellulase preparations and 20K- and 50K-cellulases function in all three tested detergents when using HEC as a substrate.

Example 15

Use of Neutral Cellulases in Detergents on Cotton Woven Fabrics

In this experiment is described the ability of the neutral cellulases to function as fabric-softening agent and to prevent fuzzing and thus to reduce pilling tendency from cotton fabric after repeated launderings in detergents. The tested cellulase preparations were ALKO4237 concentrated culture filtrate and the purified 20K- and 50K-cellulases from ALKO4237 strain (Examples 1 and 9).

The washing experiment was carried out with a Launder-Ometer LP-2 (Atlas, Ill., USA). About 10 g of prewashed (Example 3) unbleached cotton woven fabric swatch was loaded into 1.2 liter container that contained 150 ml of 0.25% detergent solution with or without cellulase. Cellulase dosages were based on protein amounts. Detergent solutions were OMO® Total (Lever, UK) and Colour Detergent Liquid (Unilever, The Netherlands). A quantity of steel balls were added into each container to increase the mechanical action. The Launder-Ometer was run at 42 rpm for 0.5 or 1 hour at 40° C. The material was washed 4 times with intermediate rinsing and drying.

Weight loss (see Example 0.6) was used to describe the amount of fuzz removed from the fabrics surface.

TABLE XV

Weight loss of the fabrics after the first washing time with neutral cellulases in detergents.

| sample no | preparation | enzyme dosage as protein/ g fabric | time h | weight loss % |
|---|---|---|---|---|
| | | In Colour Detergent Liquid: | | |
| 1 | — | — | 1 | 0.05 |
| 2 | ALKO4237 | 11 | 1 | 0.3 |
| 3 | ALKO4237 | 22 | 1 | 0.7 |
| 4 | 20K-cellulase | 2 | 1 | 0.1 |
| 5 | 20K-cellulase | 5 | 1 | 0.5 |
| 6 | 20K-cellulase | 8 | 1 | 1.0 |
| 7 | 50K-cellulase | 2 | 1 | 0.1 |
| 8 | 50K-cellulase | 5 | 1 | 0.2 |
| 9 | — | — | 0.5 | 0.2 |
| 10 | 20K-cellulase | 8 | 0.5 | 0.5 |
| | | In OMO ® Total: | | |
| 11 | — | — | 1 | 0.03 |
| 12 | 20K-cellulase | 8 | 1 | 1.1 |
| 13 | — | — | 0.5 | 0.1 |
| 14 | 20K-cellulase | 8 | 0.5 | 0.7 |

In the Table XV it is shown that after the first washing in Launder-Ometer weight loss of the fabrics were increased clearly more with cellulase treated fabrics than with the fabrics treated with the sole detergent. Also weight loss was increased as a function of cellulase dosage and further with 20K-cellulase weight loss was increased when washing time was raised from 0.5 hour to 1 hour. 20K-cellulase worked equally well in Colour Detergent Liquid and in OMO® Total. These results indicate that particularly the 20K-cellulase and ALKO4237 cellulase preparation function in detergents as fuzz removing agents after already one wash time.

After three further washing times with samples 1, 2, 4 and 7 (Table XV) the evaluation of the fabrics was performed by a panel consisting of three persons. Panelists were asked to evaluate the softness and visual appearance of the treated fabrics as follows.

The softness of the fabrics:

A. the fabric treated with cellulase is softer than the fabric treated without cellulase B. the fabric treated with cellulase is as soft as the fabric treated without cellulase C. The fabric treated with cellulase is harder than the fabric treated without cellulase The results are shown in Table XVI.

Visual appearance of the fabrics was evaluated by ranking the fabrics on a score from 1 to 5. Score of 5 gave no few or pills and the fabric texture became more apparent. Score of 1 gave many pills and fuzz. Total score for each fabric was calculated and divided by the number of the panelists. The average score of the visual appearance of each fabric is shown in Table XVI.

TABLE XVI

Softness and visual appearance of the fabrics after 4 repeated washing times with neutral cellulases in detergents.

| preparation | enzyme dosage as protein/ g fabric | time h | softness | visual appearance |
|---|---|---|---|---|
| | | In Colour Detergent Liquid: | | |
| — | — | 1 | | 1 |
| ALKO4237 | 11 | 1 | 100%: softer with cellulase | 3.2 |
| 20K-cellulase | 2 | 1 | 100%: softer with cellulase | 3.7 |
| 50K-cellulase | 2 | 1 | 100%: no difference | 1.7 |

After the 4 treatments the cellulase treated fabrics had clearly better visual appearance than the fabrics that were treated with sole detergent. Thus fabrics treated with these cellulases maintained good appearance and the fuzziness was prevented after repeated washings compared to the fabric treated without cellulases. Also after 4 wash times the ALKO4237 and 20K-cellulase treated fabrics were softer than the fabric treated with sole detergent.

Example 16

Use of Neutral Cellulases in Detergents on Cotton Fleecy Knit

In this experiment is described the ability of the neutral cellulases to function as fabric-softening agent and to prevent fuzzing and thus to reduce pilling tendency from coloured cotton fleecy knit after repeated launderings in detergents. The tested cellulase preparations were ALKO4237 concentrated culture filtrate and the purified 20K-cellulase from ALKO4237 strain (Examples 1 and 9).

Green cotton fleecy knit swatches were washed at Launder-Ometer in Colour Liquid Detergent or in OMO® Total for 1 h 3 or 10 times with or without cellulases as described in Example 15.

The evaluation of the knits was performed by a panel consisting of three persons. Panelists were asked to evaluate the softness and visual appearance (both right and reverse sides) of the treated knits as described in Example 15. Weight loss of the knits was determined as described in Example 15. The results are shown in Table XVII.

After the 3 washing times the 20K-cellulase treated knits had better visual appearance both on the right and reverse side than the knits treated with sole detergent. Knits treated 10 times with ALKO4237 cellulase preparation had clearly better visual appearance and brighter green colour than the knits treated only with detergent. The better visual appearance of the cellulase treated knits was detected already after 1 wash time (especially on the reverse side) and it was further developed during the additional washings. The cellulase treated knits were also softer than the knits treated with sole detergent.

TABLE XVII

Softness, weight loss and visual appearance of the fleecy knits after 3 or 10 repeated washing times with or without cellulases in detergents. Before washings pH of the 0.25% Colour Detergent Solution was 7.9 and 8.4 of the 0.25% OMO ® Total solution.

| preparation | enzyme dosage as protein/g fabric | washing times | pH after washings | weight loss % | softness | visual appearance right | reverse side |
|---|---|---|---|---|---|---|---|
| Colour Detergent Liquid | | | | | | | |
| — | — | 3 | 7.9 | 0.46 | | 1 | 1 |
| 20K* | 5 | 3 | 7.4 | 0.88 | 33%: softer with cellulase | 1.5 | 2.7 |
| — | — | 10 | 8.0 | 1.46 | | 1 | 1 |
| A4237 | 20 | 10 | 7.9 | 2.80 | 100%: softer with cellulase | 2.5 | 2.8 |
| OMO ® Total | | | | | | | |
| — | — | 10 | 8.3 | 0.57 | | 1 | 1 |
| A4237 | 20 | 10 | 8.2 | 1.57 | 100%: softer with cellulase | 2.3 | 2.8 |

*= 20K-cellulase

Example 17

Use of Neutral Cellulases in Detergents on Aged Cotton Fleecy Knit

In this experiment is described the ability of the neutral cellulases to function as fabric-renewal and -softening agent.

Green cotton fleecy knit was washed 10 times, with intermediate drying, in Cylinda washing machine with programme 3 at 60° C., 10 ml of OMO® Color (Lever, UK). This was to simulate the washings of the knit in practice.

After 10 treatments this aged knit had unattractive and faded appearance with a lot of fuzz at the surface.

After these 10 repeated washes the fleecy knit was used for the washing experiments with or without cellulase. Knit swatches were washed at Launder-Ometer in Colour Liquid Detergent for 1 h 1 to 3 times as described in example 15 with intermediate rinsing and drying. The cellulase preparations used were ALKO4237 concentrated culture filtrate and purified 20K- and 50K-cellulases from ALKO4237 (Example 9).

The evaluation of the knits was performed by a panel consisting of three persons. Panelists were asked to evaluate the softness and visual appearance (both right and reverse sides) of the treated knits as described in Example 15. Weight loss of the knits was determined as described in Example 15. The results are shown in Table XVIII.

After one wash time ALKO4237 and 20K-cellulase treated knits had slightly better visual appearance than the knit treated with sole detergent. The good visual appearance and more attractive look was further developed to the 20K-cellulase treated knits after 2 and 3 wash times. Visual appearance was also improved after two wash times on the knits treated with 50K-cellulase compared to the knit treated with sole detergent. As general, the knits treated with cellulases had clearly improved and attractive look while the knits treated without cellulase had still unattractive and faded appearance.

TABLE XVIII

Softness, weight loss and visual appearance of the aged fleecy knits after 1 to 3 repeated washing times with or without cellulases in detergents. Before washings pH of the 0.25% Colour Detergent Solution was 7.9.

| preparation | enzyme dosage as mg protein/ g fabric | washing times | pH after washings | weight loss % | softness | visual appearance right side | reverse |
|---|---|---|---|---|---|---|---|
| — | — | 1 | ND | 0 | | 1 | 1 |
| ALKO4237 | 20 | 1 | ND | 0.61 | 100%: no difference | 1 | 1.5 |
| 20K* | 5 | 1 | ND | 0 | 100%. no difference | 1.5 | 1.5 |
| — | — | 2 | 7.9 | 0.10 | | 1 | 1 |
| 20K* | 5 | 2 | 7.7 | 0.46 | 100%: softer with cellulase | 2.5 | 2.2 |
| 50K* | 5 | 2 | 7.7 | 0.26 | 100%: no difference | 1 | 1.2 |
| 50K* | 15 | 2 | 7.3 | 0.49 | 100%: no difference | 1 | 1.3 |
| — | — | 3 | ND | 0.31 | | 1 | 1 |
| 20K* | 5 | 3 | ND | 0.88 | 100%: softer with cellulase | 3.0 | 2.2 |

ND = not determined
* = 20K- or 50K-cellulase

Example 18

Isolation of the ALKO4237 Chromosomal DNA and Construction of the Genomic Library

*Melanocarpus albomyces* ALKO4237 was grown in shake flask cultures in potato dextrose (PD; Difco, USA)-medium at 42° C., 250 rpm for 3 days. The chromosomal DNA was isolated according to Raeder and Broda, *Lett. Appl. Microbiol.* 1:17-20 (1985). Briefly, the mycelium was washed with 20 mM EDTA and lysed in extraction buffer (200 mM Tris-HCl (pH 8.5), 250 mM NaCl, 25 mM EDTA, 0.5% SDS). The DNA was extracted with phenol and a mixture of chloroform:isoamyl alcohol (24:1 v/v). RNA was digested with RNase.

The chromosomal DNA was partially digested with Sau3A (Boehringer Mannheim, Germany) and treated with calf intestine alkaline phosphatase. DNA ranging from 5-15 kb was isolated from an agarose gel using beta-agarase (Boehringer Mannheim, Germany) and used to construct the genomic ALKO4237 library.

The predigested Lambda DASH®II BamHI Vector Kit (Stratagene, USA) was used to construct the library and the instructions of the manufacturer were followed in all the subsequent steps. Briefly, about 200 ng of the size-fractionated DNA was ligated into 1 μg of DASH®II prepared arms, and packaged using Gigapack II packaging extract (Stratagene, USA). The titer of the library was determined by infecting *E. coli* XL1-Blue MRA (P2)-cells with serial dilutions of the packaged phage and plating on NZY plates. The library was stored at 4° C. in SM-buffer, with 4% (v/v) chloroform. It was used for screening without amplification.

Example 19

Amplification, Cloning and Sequencing of the 20K-Cellulase DNA with Degenerate Primers To amplify the 20K-cellulase gene by polymerase chain reaction (PCR), a pair of degenerate primers based on the peptide sequences (FIG. 17) (SEQ ID NOS: 1-12) was synthesized. Primer 1 (429-32) (SEQ ID NO: 38) was derived from the amino acids #8-14 of the N-terminal peptide #429 (FIG. 17) (SEQ ID NO: 1), and primer 2 (fr28-16) (SEQ ID NO: 39) was designed as the antisense strand for the amino acids #2-8 of the peptide fr28 (FIG. 17) (SEQ ID NO: 11). Additional EcoR1 restriction sites were added at the 5'-termini to facilitate the cloning of the amplified fragment.

Dynazyme DNA polymerase (Finnzymes Ltd, Finland) was used according to the supplier's instructions.

| | | |
|---|---|---|
| Template DNA | (0.7 μg/μl) | 1.4 μl |
| Primer 1 | (0.5 μg/μl) | 1 μl |
| Primer 2 | (0.5 μg/μl) | 1 μl |
| dNTPs | (2 mM) | 5 μl |
| 10xPCR buffer | | 10 μl |
| dH2O | | 82 μl |
| Dynazyme | (2 U/μl) | 1 μl |
| Total | | 101.4 μl |

The PCR reaction was performed under the following conditions:

| | | |
|---|---|---|
| Step 1 | 95° C. | 5 min |
| Step 2 | 95° C. | 1 min |
| Step 3 | 56° C. | 1 min |
| Step 4 | 72° C. | 1 min |
| Step 5 | go to "step 2" | 29 more times |
| Step 6 | 72° C. | 8 min |
| Step 7 | 4° C. | hold |

Ten μl of reaction mixture was analyzed by agarose gel electrophoresis, and a single band corresponding to about 600 bp in length was detected. The remaining of the PCR product was digested with EcoR1 restriction endoglucanase, and run by agarose electrophoresis. The agarose section containing the DNA fragment was excised, and purified by the Magic PCR Preps (Promega, USA) method according to suppliers instructions. The isolated fragment was ligated with pBluescript II SK+ (Stratagene, USA) plasmid which was cut similarly with EcoR1. Competent *Escherichia coli* XL-Blue cells (Stratagene, USA) were transformed with the ligation mixture. Plasmid DNA from a few of the resulting colonies was isolated by the Magic Minipreps (Promega, USA) method according to supplier's instructions. The plasmid DNA was analyzed by agarose electrophoresis, and one clone with expected characteristics was designated pALK549.

The *Melanocarpus* DNA from pALK549 was sequenced by using ABI (Applied Biosystems, USA) kits based on fluorescent-labeled T3 and T7 primers, or sequence-specific primers with fluorescent-labeled dideoxynucleotides by the Taq dye primer cycle sequencing protocol in accordance with the supplier's instructions. Because of high GC content

```
Primer 1 (429-32) (SEQ ID NO: 38)
       EcoRI
5'- ATA GAATTC TA(C/T) TGG GA(C/T) TG(C/T) TG(C/T) AA(A/G) CC
               Y       W   D        C        C        K       P Primer 2(fr28-16) (SEQ ID NO: 39)
       EcoRI
5'- ATA GAATTC TT (A/G)TC (A/C/G/T)GC (A/G)TT (C/T)TG (A/G)AA
               N    D         A           N       Q       F
CCA
W
```

In the PCR reaction, 1 μg of the purified ALKO4237 genomic DNA (Example 18) was used as the template.

of the *Melanocarpus* DNA, the sequencing reactions were performed at annealing temperature of 58° C., with 5% (v/v)

DMSO. Sequencing reactions were analyzed on ABI 373A sequencer (Applied Biosystems, USA), and the sequences obtained were characterized by using the Genetics Computer Group Sequence Analysis Software Package, version 7.2.

The insert (594 bp) in pALK549 was found to encode the majority of the 20K-cellulase derived peptide (FIG. 17) (SEQ ID NOS: 1-12). The PCR amplified DNA (in addition to the primers) corresponds to the nucleotides 175-716 in FIGS. 19 (A and B) (SEQ ID NO:30).

Chromosomal DNA from *Myriococcum* sp. ALKO4124 was isolated as described in Example 18. A PCR reaction with the primers 429-32 and fr28-16 and ALKO4124 chromosomal DNA as the template produced a fragment of same size as from ALKO4237 DNA. This fragment was partly sequenced, and was almost identical to the ALKO4237 sequence. It is concluded that *Myriococcum* sp. ALKO4124 has a protein, which is almost identical to the 20K-cellulase of *Melanocarpus albomyces* ALKO4237. This result is also in agreement with the observation that the ALKO4237 20K-cellulase specific antibodies also recognize a 20K protein band from ALKO4124 growth medium in Western analysis (FIG. 14). Enzymes from both strains gave similar good results in biostoning experiments (Examples 3 and 4).

Example 20

Cloning and Sequencing the *Melanocarpus albomyces* ALKO4237 20K-Cellulase Gene

*E. coli* XL1-Blue MRA (P2)-cells (Stratagene, USA) were grown in LB+0.2% maltose+10 mM $MgSO_4$, and diluted to $OD_{600}$=0.5. The cells were infected with the *Melanocarpus albomyces* ALKO4237 genomic library (Example 18) for 15 min at 37° C., and plated with NZY top agar on the NZY plates. Plates were incubated at 37° C. overnight. The plaques were transferred onto a nylon filter (Hybond, Amersham, UK) according to Stratagene's instructions.

The purified PCR fragment (Example 19) was labeled with digoxigenin according to Boehringer, DIG DNA Labeling and Detection Nonradioactive, Application Manual. Hybridization was performed at 68° C. The positive clones were picked in SM buffer/chloroform, and purified with a second round of screening.

Under these conditions 4 positive clones were found. The large scale bacteriophage lambda DNA isolation from the clones was done according to Sambrook et al., in *Molecular Cloning: A Laboratory Manual*, 2nd edition, Cold Spring Harbor Laboratory Press, Cold Spring Harbor, N.Y., 1989. The phage DNAs were analyzed by digestion of the DNA with several restriction enzymes, and the digested DNA was hybridized with the PCR-probe. Three hybridizing fragments were isolated: about 2.6 kb EcoR1-XhoI fragment, about 4.9 kb XhoI fragment and about 3 kb SacI fragment. These were inserted into similarly cut pBluescript II SK+ vector (Stratagene, USA), creating plasmids pALK1221, pALK1222 and pALK1223, respectively (FIG. 18).

The *Melanocarpus albomyces* DNA in pALK1221 was sequenced as described in Example 19. The DNA sequence encoding the *Melanocarpus albomyces* 20K-cellulase is shown in FIGS. 19 (A and B) (SEQ ID NO: 30). The sequence is 936 bp in length, and has an open reading frame (ORF) coding for 235 amino acids; the gene has two introns. The putative signal peptide processing site is after alanine-21, and the N-terminus of the mature protein begins at alanine-22, as suggested by the peptide sequencing results (FIG. 17, peptide #429) (SEQ ID NO: 1). The ORF predicts a protein with a molecular weight of 25.0 kDa for the full-length preprotein, and 22.9 kDa for the mature protein. This is in good agreement with the results obtained from the protein purification work (Example 10). These results also verify that the about 35 kDa protein detected previously with the 20K-cellulase antiserum (Example 10) is a different gene product than the 20K-cellulase.

The 20K-cellulase of *Melanocarpus albomyces* appears to belong to family K of cellulases and family 45 of glycosyl hydrolases (Henrissat & Bairoch, *Biochem. J.* 293:781-788 (1993)). The 20K-cellulase shows homology (about 76% identify in 235 amino acid overlap) towards the *Humicola insolens* endoglucanase V (embl:a23635), but the 20K-cellulase has the surprising feature that it does not harbor the cellulose binding domain (CBD) and its linker, which are characteristic of the *Humicola insolens* endoglucanase V and other related endoglucanases (Schülein et al., 1993, In: Suominen & Reinikainen (eds), Foundation for Biotechnical and Industrial Fermentation Research, Helsinki, vol. 8, 109.; Saloheimo et al., 1994, *Mol. Microbiol.* 13, 219). This feature of the 20K-cellulase may account for the excellent performance of the enzyme in biostoning experiments (Example 10).

Example 21

Amplification, Cloning and Sequencing of 50 K-Cellulase DNA with Degenerate Primers The peptides derived from the 50K-cellulase (Table IX) shared some homology towards *Humicola grisea* endonuclease I (DDBJ:D63516). To amplify the 50 K-cellulase gene by polymerase chain reaction (PCR) a pair of degenerate primers based on the peptide sequences (Table IX) (SEQ ID NOS: 13-24) was synthesized. Primer 1 (507-128) (SEQ ID NO: 40) was derived from the amino acids #5-10 of the peptide #507 (Table IX) (SEQ ID NO: 13, and primer 2 (509-rev) (SEQ ID NO: 41) was designed as the antisense strand for the amino acids #4-9 of the peptide 509 (Table IX) (SEQ ID NO: 14). The order of the two peptides in the protein—and the corresponding sense-antisense nature of the primers—was deduced from comparison with the *Humicola grisea* endonuclease I.

```
Primer 1 (507-128) (SEQ ID NO:40)
5'- GA(C/T) GA(A/G) AC(A/C/G/T) GA(A/G) CA(C/T) (A/C)G
     D       E       T         E       H       R
```

-continued

Primer 2 (509-rev) (SEQ ID NO: 41)
5'-TA (A/C/G/T)GC (A/C/G/T)CC (A/C/G/T)CC (A/C/G/T)GG (A/G)TT
     Y        A         G         P         N In the PCR reaction, 1.5 µg of the purified ALKO4237 genomic DNA (Example 18) was used as the template. Dynazyme DNA polymerase (Finnzymes Ltd, Finland) was used according to the supplier's instructions.

| | | |
|---|---|---|
| Template DNA | (0.3 µg/µl) | 5 µl |
| Primer 1 | (0.5 µg/µl) | 1 µl |
| Primer 2 | (0.5 µg/µl) | 1 µl |
| dNTPs | (2 mM) | 5 µl |
| 10xPCR buffer | | 10 µl |
| dH2O | | 79 µl |
| Dynazyme | (2 U/µl) | 1 µl |
| Total | | 102 µl |

The PCR reaction was performed under the following conditions:

| | | |
|---|---|---|
| Step 1 | 95° C. | 5 min |
| Step 2 | 95° C. | 1 min |
| Step 3 | 56° C. | 1 min |
| Step 4 | 72° C. | 1 min |
| Step 5 | go to "step 2" | 29 more times |
| Step 6 | 72° C. | 8 min |
| Step 7 | 4° C. | hold |

Ten µl of reaction mixture was analyzed by agarose gel electrophoresis, and a single band corresponding to about 160 bp in length was detected. The remaining of the PCR product was loaded on a agarose gel electrophoresed, and the agarose section containing the DNA fragment was excised, and purified by the Magic PCR Preps (Promega, USA) method according to the supplier's instructions.

The isolated fragment was ligated with pBluescript II SK+ (Stratagene, USA) plasmid which had been digested with EcoRV endonuclease, and ddT-tailed as described in Holton and Graham (1990) Nucl. Acids Res. 19, 1156. Competent Escherichia coli XL-Blue cells (Stratagene, USA) were transformed with the ligation mixture. Plasmid DNA from a few of the resulting colonies was isolated by the Magic Minipreps (Promega, USA) method according to the supplier's instructions. The plasmid DNA was analyzed by agarose electrophoresis, and one clone with expected characteristics was designated pALK1064.

The insert (161 bp) in pALK1064 was sequenced as described in Example 19, and was found to contain an ORF, which predicted a peptide homologous to *Humicola grisea* endoglucanase I (DDBJ:D63516). The ORF also encoded the peptide #612 (Table IX) (SEQ ID NO: 21) from the purified 50K-cellulase. The PCR amplified DNA (in addition to the primers) corresponds to the nucleotides 404-530 in FIG. 21 (SEQ ID NO: 32).

PCR with the primers 507 and 590-rev with ALKO4124 chromosomal DNA as template (Example 19) produced a fragment of same size as from ALKO4237 DNA. This suggests that *Myriococcum* sp. ALKO4124 has a protein very similar to the 50K-cellulase of *Melanocarpus albomyces* ALKO4237. This is also supported by the fact that enzymes from both strains gave similar good results in biostoning experiments.

Example 22

Cloning and Sequencing the *Melanocarpus albomyces* ALKO4237 50K-Cellulase Gene

The genomic bank of *Melanocarpus albomyces* ALKO4237 was prepared for hybridization as described in Example 20. The purified PCR fragment carrying part of the 50K-cellulase gene (Example 21) was labeled with digoxigenin according to Boehringer, DIG DNA Labeling and Detection Nonradioactive, Application Manual. Hybridization was performed at 68° C. The positive clones were picked in SM buffer/chloroform, and purified with a second round of screening.

Under these conditions 10 positive clones were found. The large scale bacteriophage lambda DNA isolation from the clones was done according to Sambrook et al., 1989. The phage DNAs were analyzed by digestion of the DNA with several restriction enzymes, and the digested DNA was hybridized with the 50K-cellulase-specific PCR-probe. Four hybridizing fragments were isolated: about 2.8 kb SacI-XhoI fragment, about 5 kb SacI fragment, about 3.2 kb XhoI fragment, and about 2 kb EcoR1 fragment. These were inserted into similarly cut pBluescript II SK+ vector (Stratagene, USA), creating plasmids pALK1234, pALK1233, pALK1226 and pALK1227, respectively (FIG. 20).

The *Melanocarpus albomyces* ALKO4237 DNA was sequenced from the 50 K-cellulase specific plasmids mentioned above. The sequencing protocol has been described in Example 19.

The DNA encoding the *Melanocarpus albomyces* 50K-cellulase is shown in FIGS. 21 (A, B and C) (SEQ ID NO: 32). The sequence reveals an ORF of about 1363 bp in length, interrupted by one intron. The ORF codes for 428 amino acids. The predicted protein has a molecular weight of 46.8 kDa and after signal peptide cleavage of 44.8 kDa. All the peptides in Table IX (SEQ ID NOS: 13-24) are found in the predicted protein sequence (FIG. 21) (SEQ ID NO: 33.), although some amino acids identified with uncertainty during the peptide sequencing proved to be incorrect. The protein shows homology to *Humicola grisea* endoglucanase I (DDBJ:D63516).

Example 23

Amplification, Cloning and Sequencing of 50K-Cellulase B DNA with Degenerate Primers The peptides derived from the 50K-cellulase B (Table X) (SEQ ID NOS: 25-29) shared some homology towards *Humicola grisea* cellobiohydrolase I (DDBJ:D63515). To amplify the 50K-cellulase B gene by polymerase chain reaction (PCR) a pair of degenerate primers based on the peptide sequences (Table X) (SEQ ID NOS: 25-29) was synthesized. Primer 1 (636) (SEQ ID NO: 42) was derived from the amino acids #1-5 of the peptide #636 (Table X) (SEQ ID NO: 29) (the first amino acids was guessed to be lysine, because the peptide was isolated after digestion with a protease cleaving after lysines), and primer 2 (534-rev) (SEQ ID NO: 43) was designed as the antisense strand for the amino acids #3-8 of the peptide #534 (Table X) (SEQ ID NO: 25). The order of the two peptides in the protein—and the corresponding sense-antisense nature of the primers— was deduced from comparison with the *Humicola grisea* cellobiohydrolase I.

```
Primer 1 (636) (SEQ ID NO: 42)
5'- AA(A/G) CA(C/T) GA(A/G) TA(C/T) GG(A/C/G/T) AC
     K       H       E       Y       G          T Primer 2 (534-rev) (SEQ ID NO: 43)
5' -CC (A/G)TA (A/G)AA (A/G)TC (A/C/G/T) GG (A/G)TT
       G       Y       F       D         P        N
```

In the PCR reaction, 1.5 µg of the purified ALKO4237 genomic DNA (Example 18) was used as the template. Dynazyme DNA polymerase (Finnzymes Ltd, Finland) was used according to the supplier's instructions.

| Template DNA | (0.3 µg/µl) | 5 µl |
|---|---|---|
| Primer 1 | (0.3 µg/µl) | 1.7 µl |
| Primer 2 | (0.3 µg/µl) | 1.7 µl |
| dNTPs | (2 mM) | 5 µl |
| 10xPCR buffer | | 10 µl |
| dH2O | | 80 µl |
| Dynazyme | (2 U/µl) | 1 µl |
| Total | | 104.4 µl |

The PCR reaction was performed under the following conditions:

| Step 1 | 95° C. | 5 min |
|---|---|---|
| Step 2 | 95° C. | 1 min |
| Step 3 | 48° C. | 1 min |
| Step 4 | 72° C. | 2 min |
| Step 5 | go to "step 2" | 34 more times |
| Step 6 | 72° C. | 8 min |
| Step 7 | 4° C. | hold |

Twenty µl of reaction mixture was analyzed by agarose gel electrophoresis, and a few bands were detected. One of the bands had an apparent size of 700 bp, which size was in agreement with size one would expect, when comparing with *Humicola grisea* cellobiohydrolase gene, particularly, if the fragment contained one or more introns. The PCR products were purified by the Magic PCR Preps (Promega, USA) method according to the supplier's instructions.

The isolated fragments was ligated with pBluescript II SK+ (Stratagene, USA) plasmid which had been digested with EcoRV endonuclease, and ddT-tailed as described in Holton and Graham, *Nucl. Acids Res.* 19:1156 (1990). Competent *Escherichia coli* XL-Blue cells (Stratagene, USA) were transformed with the ligation mixture. Plasmid DNA from a few of the resulting colonies was isolated by the Magic Minipreps (Promega, USA) method according to the supplier's instructions. The plasmid DNA was analyzed by agarose electrophoresis, and one clone with about 700 bp insert was designated pALK1224.

The insert in pALK1224 was sequenced as described in Example 19, and was found to contain an ORF encoding the whole peptide #636 (SEQ ID NO: 29) from 50K-cellulase B (Table X). The ORF predicted a peptide homologous to *Humicola grisea* cellobiohydrolase I (DDBJ:D63515). The PCR amplified DNA (in addition to the primers) corresponds to the nucleotides 371-1023 in FIGS. 23 (A, B and C) (SEQ ID NO: 34).

Example 24

Cloning and Sequencing the *Melanocarpus albomyces* ALKO4237 50K-Cellulase B Gene The genomic bank of *Melanocarpus albomyces* ALKO4237 was prepared for hybridization as described in Example 20. The insert in pALK1224 was removed by digesting the plasmid with restriction endoglucanases EcoRI and HindIII. The digested plasmid DNA was run by agarose electrophoresis. The agarose section containing the about 700 bp DNA fragment was excised, and purified by the Magic PCR Preps (Promega, USA) method according to the supplier's instructions.

The purified PCR fragment from pALK1224 carrying part of the 50K-cellulase B gene (Example 23) was labeled with digoxigenin according to Boehringer, DIG DNA Labeling and Detection Nonradioactive, Application Manual. Hybridization was performed at 68° C. The positive clones were picked in SM buffer/chloroform, and purified with a second round of screening.

Under these conditions 3 positive clones were found. The large scale bacteriophage lambda DNA isolation from the clones was done according to Sambrook et al., in *Molecular Cloning: A Laboratory Manual*, 2nd edition, Cold Spring Harbor Laboratory Press, Cold Spring Harbor, N.Y., 1989. The phage DNAs were analyzed by digestion of the DNA with several restriction enzymes, and the digested DNA was hybridized with the 50K-cellulase B specific PCR probe. A hybridizing 3.5 kb NotI fragment was isolated, and inserted into similarly cut pBluescript II SK+ vector (Stratagene, USA), creating plasmid pALK1229 (FIG. 22).

The extreme 5'-end of the gene was found by hybridizing the phage DNAs with 0.2 kb NotI-PstI-fragment from pALK1229. A hybridizing 2.4 kb PstI-fragment was isolated and inserted into similarly cut pBluescript II SK+ vector (Stratagene, USA), creating plasmid pALK1236 (FIG. 22).

Part of the inserts in pALK1229 and pALK1236 were sequenced as described in Example 19. The DNA encoding the *Melanocarpus albomyces* 50K-cellulase B is shown in (FIGS. 23A, B and C) (SEQ ID NO: 34). The sequence reveals an ORF of 1734 bp in length interrupted by five introns. The ORF codes for 452 amino acids. The predicted protein has a molecular weight of 49.9 kDa and after signal peptide cleavage of 47.6 kDa. All the peptides in Table X (SEQ ID NOS: 25-29) are found in the predicted protein sequence (FIGS. 23A, B and C) (SEQ ID NO: 35), although some amino acids identified with uncertainty during the peptide sequencing proved to be incorrect. The predicted protein shows homology to *Humicola grisea* cellobiohydrolase I (DDBJ:D63515) and other cellobiohydrolases. However, 50K-cellulase B has the surprising feature that it does not harbor the cellulose binding domain (CBD) and its linker, which is characteristic to *Humicola* grisea cellobiohydrolase I and many other cellobiohydrolases.

Example 25

Screening the *Melanocarpus albomyces* ALKO4237 Genomic Library with *Trichoderma reesei* Cellulases Genes The genomic bank of *Melanocarpus albomyces* ALKO4237 was prepared for hybridization as described in Example 20.

A DNA fragment carrying *Trichoderma reesei* cbh1 specific DNA was isolated by cutting plasmid pTTc01 (FIG. 24) with restriction endonuclease HincII, and isolating the about 1.6 kb fragment from agarose gel after electrophoresis. A DNA fragment carrying *Trichoderma reesei* egl2 specific DNA was isolated by cutting plasmid pMS2 (FIG. 25) with restriction endonucleases BamHI and EcoRI, and isolating the about 1.5 kb fragment from agarose gel after electrophoresis. The cloning of the cbh1 gene is described in Teeri et al., *Bio/Technology* 1:696-699 (1983) and the DNA sequence is described in Shoemaker et al., *Bio/Technology* 1: 691-696 (1983). The egl2 (originally called "egl3") gene is described in Salohemio et al., *Gene* 63:11-21 (1988).

The fragments were labeled with digoxigenin according to Boehringer, DIG DNA Labeling and Detection Nonradioactive, Application Manual. Hybridization was performed at 68° C. with the cbh1 probe and at 60° C. with the egl2 probe. The positive clones were picked in SM buffer/chloroform, and purified with a second round of screening.

Under these conditions 13 cbh1 positive and 6 egl2 positive clones were found. One clone hybridized to both probes. The lambda DNA was isolated from the clones as described above. The phage DNAs were analyzed by digestion of the DNA with several restriction enzymes, and the digested DNA was hybridized with the cbh1 and egl2 probes. The clones were also hybridized with the 20K-cellulase-specific PCR fragment (Example 19). One clone (lambda-16) was clearly positive, and two other clones (lambda-8/1 and lambda-5/2) were weakly positive; all these clones were originally picked with the cbh1 probe.

An about 4 kb EcoRI fragment from lambda-16, which hybridized to both the *Trichoderma reesei* cbh1 probe and to the 20K-cellulase specific PCR fragment, was isolated from agarose gel after electrophoresis, and inserted into similarly cut pBluescript 11 SK+. The resulting plasmid was named pALK1230 (FIG. 26).

Part of the insert in pALK1230 was sequenced as described in Example 19. The DNA appears not to encode the 20K-cellulase, but codes for a protein homologous to several cellulases, particularly at the cellulose binding domain (CBD) area. Thus the gene product very likely has high affinity towards cellulosic material, and therefor this gene product was designated as protein-with-CBC. The sequence is shown in FIG. 27 (SEQ ID NO: 36).

PCR reactions with the primers 636 (SEQ ID NO: 42) and 534-rev (SEQ ID NO: 43) (Example 23) were performed with the DNA from the 19 lambda clones as templates. One lambda clone, lambda-3, gave a band about 700 bp in size, similar to that in Example 23 when ALKO04237 chromosomal DNA was used as a template. This clone had originally been picked by the *Trichoderma* cbh1 probe. The lambda DNA was digested with several restriction endonucleases, and hybridized with the 50K-cellulase B specific probe. The clone showed similar restriction enzyme pattern as the 3 clones in Example 24. It is concluded that lambda-3 also carries the 50K-cellulase B gene.

Example 26

Fusion Proteins

A recombinant vector encoding the 20K-cellulase, 50K-cellulase or the 50K-cellulase B is prepared by fusing the cellulase encoding sequence with the sequence of *Trichoderma reesei* cellulase or hemicellulase or at least one functional domain of said cellulase or hemicellulase, as described in U.S. Pat. No. 5,298,405, WO 93/24621 and in Genbank submission L25310, incorporated herein by reference. Especially, the enzyme is selected from the group consisting of CBHI, CBHII, EGI, EGII, XYLI, XYLII and MANI, or a domain thereof, such as the secretion signal or the core sequence.

Fusion proteins can be constructed that contain an N-terminal mannanase or cellobiohydrolase or endoglucanase core domain or the core and the hinge domains from the same, fused to one of the *Melanocarpus* cellulase sequences. The result is a protein that contains an N-terminal mannanase or cellobiohydrolase or endoglucanase core or core and hinge regions, and a C-terminal *Melanocarpus* cellulase. The fusion protein contains both the *Trichoderma* mannanase or cellobiohydrolase or endoglucanase and the *Melanocarpus* cellulase activities of the various domains as provided in the fusion construct. Alternatively, mutations that modify the activities of the *Trichoderma* mannanase or cellobiohydrolase or endoglucanase, or the *Melanocarpus* cellulase activities, may be included in the constructions. In this case, the fusion proteins contain both the modified *Trichoderma* enzyme activity and the *Melanocarpus* cellulase activity of the various domains as provided in the fusion construct.

Fusion proteins can also be constructed such that the mannanase or cellobiohydrolase or endoglucanase tail or a desired fragment thereof, is placed before one of the *Melanocarpus* cellulase sequences, especially so as to allow use of a nonspecific protease site in the tail as protease site for the recovery of the *Melanocarpus* cellulase part from the expressed fusion protein. Alternatively, fusion proteins can be constructed that provide for a protease site in a synthetic linker that is placed before one of the *Melanocarpus* cellulases, with or without the tail sequences.

Example 27

Hosts

The recombinant construct encoding the desired fusion proteins or *Melanocarpus* proteins are prepared as above, and transformed into a filamentous fungus such as *Aspergillus* spp., preferably *Trichoderma* spp.

Example 28

*Trichoderma* Background for 20K-Cellulase Production

In this example is described stone-washing experiments to determine the most suitable background of *Trichoderma* cellulases for 20K-cellulase production. The purpose of these experiments was to determine which *Trichoderma* cellulases would cause backstaining in stone-washing at neutral conditions.

*Trichoderma reesei* strain ALKO3620 (endoglucanase 2 gene is deleted) was chosen as host for these experiments. In previous studies *Trichoderma* EGII (endoglucanase II) enzyme has been shown to cause detrimental effects to cotton fibre structures and thus to weaken the strength properties of cotton-containing fabrics (In: Miettinen-Oinonen et al.: Effects of cellulases on cotton fiber and fabrics. In: *Proceedings of the TIWC96 Conference*, 1996, Vol. 1 (2), pp. 197.).

Stone-washing experiments were performed at pH 6.5 and 7 as described in Example 3 except that no Berol was used.

The tested *Trichoderma* cellulase preparations were:
ALKO3133 (egl2 and cbh2 deleted)
ALKO3269 (egl2 and egl1 deleted)
ALKO3268 (egl2 and cbh1 deleted)

The dosage of *Trichoderma* preparations was about 2.5 mg (=low dosage, L) or about 5 mg (=high dosage, H) of total protein per g of fabric. 0.4 mg of purified 20K-cellulase per g of fabric was used when needed.

Results of color measurements of treated denim fabrics are shown in Table XIX.

The stone-washing results show that ALKO3269 (egl2 and egl1 deleted) background causes less backstaining at neutral conditions than ALKO3268 (egl2 and cbh1 deleted) or ALKO3133 (egl2 and cbh2 deleted) background. Thus the preferred host for 20K-cellulase production for biostoning is an ALKO3269-like strain. Although with higher 20K-cellulase concentrations the *Trichoderma* background has probably only very minor importance. An ALKO3269-like background is probably as good for 50K-cellulase and 50K-cellulase B production for biostoning as it is for 20K-cellulase production.

TABLE XIX

Color measurements of denim fabrics treated with different *Trichoderma* cellulase preparations with (+) or without (−) 20K-cellulase.

| preparation/dosage | 20K +/− | pH | Right side | | | Reverse side | | |
|---|---|---|---|---|---|---|---|---|
| | | | L | b | deltaE | L | b | deltaE |
| — | − | 6.5 | 2.2 | 1.1 | 3.1 | 0.7 | 0.1 | 1.4 |
| ALKO3620/L | − | 6.5 | 2.2 | 2.6 | 3.0 | −0.7 | 2.6 | 2.9 |
| ALKO3620/L | + | 6.5 | 5.5 | 4.0 | 7.7 | −1.3 | 5.0 | 5.5 |
| ALKO3133/L | − | 6.5 | 1.9 | 2.2 | 3.7 | 0.2 | 1.6 | 2.3 |
| ALKO3133/H | − | 6.5 | 4.2 | 1.9 | 4.5 | −1.5 | 3.3 | 4.8 |
| ALKO3133/L | + | 6.5 | 5.7 | 4.3 | 7.8 | 0.3 | 4.5 | 5.0 |
| ALKO3133/H | + | 6.5 | 8.5 | 4.0 | 9.4 | −1.4 | 5.9 | 7.8 |
| ALKO3269/L | − | 6.5 | 2.9 | 1.9 | 4.4 | 0.8 | 0.8 | 1.6 |
| ALKO3269/H | − | 6.5 | 4.3 | 1.5 | 4.5 | 0.6 | 1.3 | 2.6 |
| ALKO3269/L | + | 6.5 | 6.6 | 4.2 | 8.7 | 1.1 | 4.0 | 4.3 |
| ALKO3269/H | + | 6.5 | 7.9 | 3.9 | 8.5 | 0.7 | 3.7 | 5.1 |
| ALKO3268/L | − | 6.5 | 2.9 | 1.7 | 3.7 | 0.1 | 1.8 | 3.0 |
| ALKO3268/H | − | 6.5 | 4.2 | 2.0 | 4.3 | −0.7 | 3.4 | 5.0 |
| ALKO3268/L | + | 6.5 | 5.9 | 3.2 | 7.7 | −1.2 | 4.5 | 6.0 |
| ALKO3268/H | + | 6.5 | 7.1 | 3.7 | 7.7 | −2.0 | 5.8 | 7.3 |
| — | − | 7.0 | 2.9 | 0.8 | 2.6 | 0.7 | 0.5 | 1.5 |
| ALKO3620/L | − | 7.0 | 3.3 | 1.2 | 1.9 | 1.7 | 0.3 | 1.1 |
| ALKO3620/L | + | 7.0 | 6.7 | 3.4 | 5.6 | 1.1 | 3.2 | 2.9 |
| ALKO3133/L | − | 7.0 | 3.2 | 1.0 | 1.4 | 0.6 | 0.6 | 0.9 |
| ALKO3133/L | + | 7.0 | 5.9 | 3.7 | 5.5 | 0.1 | 4.3 | 3.1 |
| ALKO3269/L | − | 7.0 | 3.6 | 1.2 | 2.2 | 1.3 | −0.3 | 1.3 |
| ALKO3269/L | + | 7.0 | 6.4 | 3.4 | 5.9 | 1.2 | 3.2 | 2.8 |
| ALKO3268/L | − | 7.0 | 2.9 | 1.4 | 3.9 | 0.5 | 0.4 | 2.5 |
| ALKO3268/L | + | 7.0 | 8.4 | 3.1 | 9.6 | 1.1 | 3.5 | 4.6 |

Example 29

Production of *Melanocarpus albomyces* ALKO4237 20K-Cellulase in *T. reesei*

The *Trichoderma reesei* strains were constructed for *Melanocarpus albomyces* ALKO4237 20K-cellulase production. Strains produce *Melanocarpus* 20K-cellulase and are unable to produce *T. reesei*'s endoglucanase II and cellobiohydrolase I or endoglucanase I. Such preparations deficient in *Trichoderma* cellulolytic activity, and the making of same by recombinant DNA methods, are described in U.S. Pat. No. 5,298,405 or Suominen et al. (1993) High frequency one-step gene replacement in *Trichoderma reesei*. II. Effects of deletions of individual cellulase genes. *Mol. Gen. Genet*. 241: 523., incorporated herein by reference.

In construction of the *Melanocarpus albomyces* 20K-cellulase producing strains, the parental *Trichoderma reesei* strain ALKO3620 was transformed with the expression cassettes from the plasmid pALK1231 or pALK1235 (FIGS. 28 and 29). In the cassettes 20K-cellulase is expressed from the strong cbh1 promoter. The integration of the expression cassettes resulted in the replacements of the parental cbh1 (pALK1231) or the egl1 (pALK1235) genes.

In the host strain ALKO3620 the egl2 gene has been replaced by the 3.3 kb XbaI-BglII fragment of the ble gene from *Streptoalloteichus hindustanus* (Mattern et al. (1988) A vector of *Aspergillus* transformation conferring phleomycin resistance. *Fungal Genet. Newslett*. 35: 25.; Drocourt et al. (1990) Cassettes of the *Streptoalloteichus hindustanus* ble gene for transformation of lower and higher eukaryotes to phleomycin resistance. *Nucl. Acids Res*. 18: 4009.) using the recombinant DNA methods described in U.S. Pat. No. 5,298,405, incorporated herein by reference.

The plasmids pALK1231 and pALK1235 that were used in the construction of the *Melanocarpus* cellulase producing strains are identical to each other with respect to cbh1 promoter, 20K-cellulase gene and cbh1 terminator which are described below:

*T. reesei* cbh1 (cellobiohydrolase 1) promoter: The promoter is from *Trichoderma reesei* VTT-D-80133 (Teeri et al. (1983) The molecular cloning of the major cellulase gene from *Trichoderma reesei*. *Bio/Technology* 1: 696.). The 2.2 kb EcoR1-SacII fragment (Karhunen et al. (1993) High frequency one-step gene replacement in *Trichoderma reesei*. I. Endoglucanase I overproduction. *Mol. Gen. Genet.* 241: 515) was used in the construct. The sequence of the promoter area preceding the ATG was published by Shoemaker et al. (1983) Molecular cloning of exo-cellobiohydrolase from *Trichoderma reesei* strain L27. *Bio/Technology* 1.691.). The last 15 nucleotides of the *T. reesei* L27 cbh1 promoter (the SacII site is underlined) are CCGCGGACTGGCATC (SEQ ID NO: 44) (Shoemaker et al. 1983). The cbh1 promoter from the *T. reesei* strain VTT-D-80133 has been sequenced at Alko Research Laboratories, and one nucleotide difference in the DNA sequence has been noticed within the above mentioned region. In the *T. reesei* strain VTT-D-80133 the sequence preceding the ATG is CCGCGGACTG/C/GCATC (SEQ ID NO: 45) (the SacII site is underlined, the additional cytosine in the DNA sequence is between the slashes).

The nucleotides missing from the promoter (10 bps after the SacII to the ATG) were added and the exact promoter fusion to the first ATG of the *Melanocarpus* 20K-cellulase (see below) was done by using the PCR (polymerase chain reaction) method. The fusion and the PCR fragment were sequenced to ensure that no errors had occurred in the reaction. In pALK1231 the promoter area is also functioning as a homologous DNA (together with the cbh1 3'-fragment; see below) to target the integration of the transforming DNA into the cbh1 locus.

*Melanocarpus albomyces* 20K-cellulase gene: The nucleotide sequence and deduced amino acid sequence of the 20K-cellulase gene encoding a 20 kDa cellulase is presented in Example 20 (FIG. 19) (SEQ ID NOS: 30-31). A 0.9 kb fragment beginning from ATG-codon was used in both plasmids.

*T. reesei* cbh1 terminator: The 739 bp AvaII fragment (Karhunen et al. (1993) High frequency one-step gene replacement in *Trichoderma reesei*. I. Endoglucanase I overproduction. *Mol. Gen. Genet.* 241: 515.) starting 113 bp before the STOP codon of the cbh1 gene was added after the 20K-cellulase gene to ensure termination of transcription.

In addition the material described above the plasmid pALK1231 contains:

amdS gene: The gene has been isolated from *Aspergillus nidulans* VH1-TRSX6 and it is coding for acetamidase (Hynes et al. (1983) Isolation of genomic clones containing the amdS gene of *Aspergillus nidulans* and their use in the analysis of the structural and regulatory mutations. *Mol. Cell. Biol.* 3: 1430.). Acetamidase enables the strain to grow by using acetamide as the only nitrogen source and this characteristics has been used for selecting the transformants. The 3.1 kb fragment (SpeI-XbaI) from the plasmid p3SR2 (Kelly J. and Hynes M. (1985) Transformation of *Aspergillus niger* by the amdS gene of *Aspergillus nidulans*. *EMBO J.* 4: 475.) is used in the plasmids. The fragment contains 1007 bps of the promoter area, 1897 bps of the coding region (introns included) and the 183 bps terminator area of the amdS gene.

cbh1 3'-fragment: The fragment was isolated from *T. reesei* ALKO2466 by using plasmid rescue (1.7 kb, BamHI-EcoRI, starting 1.4 kb after the gene's STOP, Suominen et al. (1993) High frequency one-step gene replacement in *Trichoderma reesei*. II. Effects of deletions of individual cellulase genes. *Mol. Gen. Genet.* 241: 523.). Strain ALKO2466 derives from the strain ALKO233 (Harkki et al. (1991) Genetic engineering of *Trichoderma* to produce strains with novel cellulase profiles. *Enzyme Microb. Technol.* 13: 227.). 3'-fragment is used together with the promoter area to target the 20K-cellulase gene to the cbh1 locus by homologous recombination.

The plasmid pALK1235 contains:

hph gene: The gene encoding HmB phosphotransferase is originally isolated from *E. coli* K-12 JM109 (Yanish-Perron et al. (1985) Improved M13 phage cloning vectors and host strains: nucleotide sequences of the M13 mp18 and pUC19 vectors. *Gene* 33: 103.) and it confers resistance to hygromycin B (HmB). Resistance to hygromycin (inactivated by phosphorylation by HmB phosphotransferase) was used for selecting the transformants. The hph gene together with the pki promoter and cbh2 terminator (see below) is isolated from plasmid pRLM$_{ex}$30 (Mach et al. (1994) Transformation of *Trichoderma reesei* based on hygromycin B resistance using homologous expression signals. *Curr. Genet.* 25: 567.) as a 2.2 kb NotI-PvuII fragment.

pki promoter: The about 0.75 kb pki (pyruvate kinase) promoter for expressing hph has been synthesized by PCR using *T. reesei* QM 9414 DNA as a template (Schindler et a. (1993) Characterization of the pyruvate kinase-encoding gene (pki1) of *Trichoderma reesei*. *Gene* 130: 271.).

cbh2 terminator: The cbh2 terminator sequence starts immediately after the STOP codon of the cbh2 gene (to the PvuII site 0.5 kb from the STOP codon; Mach et al. (1994) Transformation of *Trichoderma reesei* based on hygromycin B resistance using homologous expression signals. *Curr. Genet.* 25: 567.) and originates from plasmid pRLM$_{ex}$30.

egl1 5'-fragment: The 1.8 kb egl1 5'-fragment (ScaI-StuI) has been isolated from *T. reesei* QM 6a (Mandels and Reese (1957) Induction of cellulase in *Trichoderma viridae* as influenced by carbon sources and metals. *J. Bacteriol.* 73: 269.). This fragment is situated about 1.35 kb upstream from the egl1 coding region and it was used to target the integration of the the transforming DNA into the egl1 locus.

egl1 3'-fragment: The 1.6 kb egl1 3'-fragment (ScaI-XhoI) was, like the 5'-fragment, isolated from *T. reesei* QM 6a. The fragment is situated 0.3 kb downstream from the end of the egl1 gene and it was used for targeting of the transforming DNA into the egl1 locus.

The standard DNA methods described by Sambrook et al. (1989) In: *Molecular cloning: a laboratory manual*, 2nd ed. Cold Spring Harbor Laboratory Press, Cold Spring Harbor, N.Y. were used in construction of the vectors. Me restriction enzymes, T4 DNA ligase, Kenow fragment of the DNA polymerase I, T4 DNA polymerase, polynucleotide kinase and Taq polymerase were from Boehringer Mannheim, Germany) and New England Biolabs (USA). Each enzyme was used according to the supplier's instructions. Plasmid DNA was isolated by using Qiagen columns (Qiagen GmbH, Germany) or Promega Magic Miniprep (Promega, USA) according to the manufacturer's protocols. The oligonucleotides used in the PCR-reactions and in sequencing reactions were synthetized by a ABI (Applied Biosystems, USA) 381A DNA Synthetizer. DNA sequencing was done as described in Example 19.

DNA fragments for cloning or transformations were isolated from low-melting-point agarose gels (FMC Bioproducts, USA) by β-agarase I treatment (New England Biolabs, USA) or by using the QIAEX Gel Extraction Kit (Qiagen GmbH, Germany) according to the supplier's instructions.

*T. reesei* ALKO3620 was transformed as described by Penttilä et al. (1987) A versatile transformation system for the cellulolytic filamentous fungus *Trichoderma reesei*. Gene 61: 155.) with the modifications described in Karhunen et al. (1993) High frequency one-step gene replacement in *Trichoderma reesei*. I. Endoglucanase I overproduction. *Mol. Gen. Genet.* 241: 515.). *T. reesei* transformants were transferred on a selective medium and purified through conidia. Transformants were stabilized by growing them on selective slants for two generations prior to sporulating on potato dextrose agar.

Example 30

Characteristics of the *Melanocarpus albomyces* ALKO4237 20K-Cellulase Producing Transformants The purified transformants were grown in shake flasks in a medium containing 4% whey, 1.5% complex nitrogen source derived from grain, 5% $KH_2PO_4$ and 0.5% $(NH_4)_2SO_4$. Cultures were grown at 30° C. and 250 rpm for 7 days.

The culture supernatants were blotted directly onto nitrocellulose filters by a dot-blot apparatus. CBHI was detected by immunostaining using a CBHI specific monoclonal antibody C1-258 and EGI by spesific monoclonal antibody EI-2 (Aho et al. (1991) Monoclonal antibodies against core and cellulose-binding domains of *Trichoderma reesei* cellobiohydrolases I and II and endoglucanase I. *Eur. J. Biochem.* 200: 643.) and the ProtoBlot Western blot AP system (Promega. USA) according to the recommondations of the manufacturer.

The *T. reesei* strains ALKO3620/pALK1231/14, ALKO3620/pALK1231/16, ALKO3620/pALK1231/20 and ALKO3620/pALK1231/59 do not contain the cbh1 gene. The cbh1 gene is replaced by the amdS marker gene and the 20K-cellulase construct in pALK1231 expression cassette. The cbh1 gene replacement was verified in Southern hybridisations. The *T. reesei* strains ALKO3620/pALK1235/40 and ALKO3620/pALK1235/49 do not contain the egl1 gene. The egl1 gene is replaced by the hph marker gene and the 20K-cellulase construct in pALK1235 expression cassettes. The egl1 gene replacement was verified in Southern hybridisations. The host strain ALKO3620 used in the transformations is deficient of the egl2 gene (replaced by ble gene from *Streptoalloteichus hindustanus* (Mattern et al., 1988, Drocourt et al., 1990). Thus the strains do not produce *Trichoderma*'s cellulase components EGII and CBHI or EGI.

Samples from the culture supernatants were run on polyacrylamide slab gels containing 0.1% SDS on Bio-Rad Mini Protean II electrophoresis system (USA). The polyclonal antibody prepared against the purified 20K-cellulase was used to detect the produced protein in Western blots. In the detection, Promega's ProtoBlot® AP System was used. The Western result is shown in FIG. 30. The transformants ALKO3620/pALK1235/49, ALKO3620/pALK1235/40, ALKO3620/pALK1231/14 and ALKO3620/pALK1231/16 (lanes 1, 2, 4 and 5) produce a protein which reacts with the polyclonal 20K-cellulase antiserum. The size of the protein produced by transformants is same as the size of purified 20K-cellulase (lane 6). ALKO3620 (lane 3) does not produce corresponding protein.

The endoglucanase activities of the transformants were determined as described in Example 10. When 2% carboxymethylcellulose (CMC) was used as a substrate reaction temperature was lifted up to 70° C. and thus the endoglucanase activity of ALKO3620 was heat inactivated. When using 1% hydroxyethylcellulose as a substrate heat inactivation was performed before enzymatic activity measurements. Samples from growth medium were diluted to 0.05 M HEPES, pH 7.0-buffer and incubated 20 min in 70° C. Heat inactivation of endoglucanase I (the major endoglucanase left in ALKO3620) was almost complete. The activity of egl1-negative transformants dropped about 30% in heat inactivation which indicates the minor heat inactivation of 20K-cellulase. The endoglucanase activities are presented in Table XX. When HEC was the substrate, the 20K-cellulase activity was extrapolated to the activity before the heat treatment by dividing the activity obtained after the heat treatment with 0.7.

TABLE XX

The endoglucanase activities of *T. reesei* transformants producing *Melanocarpus albomyces* 20K-cellulase.

| Substrate | CMC 70° C., pH 7.0 | 20K-cellulase activity (artificial units/ml) HEC 50° C., pH 7.0 |
|---|---|---|
| ALKO4237 | —* | 100** |
| ALKO3620 | 50*** | 38*** |
| ALKO3620/pALK1231/14 | 2400 | 350 |
| ALKO3620/pALK1231/16 | 2600 | 350 |
| ALKO3620/pALK1231/20 | 6500 | 750 |
| ALKO3620/pALK1231/59 | 6800 | 750 |
| ALKO3620/pALK1235/40 | 2400 | 325 |
| ALKO3620/pALK1235/49 | 2100 | 350 |

*not measured
**not heat inactivated, contains also 50K-cellulase, 50K-cellulase B and other cellulase activities.
***activity due to *Trichoderma* cellulases The endoglucanase activities of the *T. reesei* host strain ALKO3620 are almost totally heat inactivated at 70° C. *Melanocarpus albomyces* 20K-cellulase producing transformants produce substantial amounts of relative heat stable 20K-cellulase. The endoglucanase production level of transformants is several times higher than that of 20K-cellulase parental strain ALKO4237.

Example 31

Production of *Melanocarpus albomyces* ALKO4237 50K-Cellulase in *T. reesei*

The *Trichoderma reesei* strains were constructed for *Melanocarpus albomyces* ALKO4237 50K-cellulase production. Strains produce *Melanocarpus* 50K-cellulase and are unable to produce *T. reesei*'s endoglucanase II and cellobiohydrolase I or endoglucanase I. In construction of the *Melanocarpus albomyces* 50K-cellulase producing strains, the parental *Trichoderma reesei* strain ALKO3620 was transformed with the expression cassettes from the plasmid pALK1238 or pALK1240 (FIGS. 31 and 32). In the cassettes 50K-cellulase is expressed from the strong cbh1 promoter. The integration of the expression cassettes results in the replacements of the parental cbh1(pALK1238) or the egl1 (pALK1240) genes. Cloning and transformation were done as described in Example 29, except that 20K-cellulase gene was replaced by 50K-cellulase gene (1.7 kb fragment beginning from ATG-codon) described in Example 22. The *Melanocarpus albomyces* 50K-cellulase producing transformants are then characterized similar to example 30 with modifications obvious to a person skilled in the art. The *Melanocarpus albomyces* 50K-cellulase B and protein-with-CBD producing transformants can be created similar to Examples 29 and 30 with modifications obvious to a person skilled in the art.

Having now fully described the invention, it will be understood by those with skill in the art that the invention may be performed within a wide and equivalent range of conditions, parameters and the like, without affecting the spirit or scope of the invention or any embodiment thereof. All references cited herein are fully incorporated herein by reference.

| Applicant's or agent's file reference number | International application No. |
|---|---|

118

INDICATIONS RELATING TO A DEPOSITED MICROORGANISM (PCT Rule 13*bis*)

A. The indications made below relate to the microorganism referred to in the description
on page ____9____ , line ____2-4____

B. IDENTIFICATION OF DEPOSIT    Further deposits are identified on an additional sheet [X]

Name of depositary institution

Centraalbureau voor Schimmelcultures

Address of depositary institution *(including postal code and country)*

Oosterstraat 1
P.O. Box 273
3740 AG BAARN
The Netherlands

| Date of deposit | Accession Number |
|---|---|
| 12 October 1995 | CBS 689.95 |

C. ADDITIONAL INDICATIONS *(leave blank if not applicable)*    This information is continued on an additional sheet [X]

EP    The microorganism shall be made available as provided in Rule 28(3) and 28(4) of the implementing regulations of EPC.

FI    The microorganism shall be made available as provided in Finnish Patent Law 22 § 7.

Enclosed recognition of receipt and viability statement

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g. "Accession Number of Deposit")*

---

For receiving Office use only

[ ] This sheet was received with the international application

Authorized officer

---

For International Bureau use only

[ ] This sheet was received by the International Bureau on

Authorized officer

Form PCT/RO/134 (July 1992)

BP/A/II/12
page 14

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| Primalco Ltd, Biotec<br>Valta-akseli<br>05200 Rajamaki<br>Finland | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |
|---|---|
| name and address of depositor | |

I. IDENTIFICATION OF THE MICROORGANISM

| Identification reference given by the DEPOSITOR:<br>ALKO4179 | Accession number given by the INTERNATIONAL DEPOSITARY AUTHORITY:<br>CBS 689.95 |
|---|---|

II. SCIENTIFIC DESCRIPTION AND/OR PROPOSED TAXONOMIC DESIGNATION

The microorganism identified under I above was accompanied by:

[X] a scientific description

[ ] a proposed taxonomic designation (mark with a cross where applicable)

III. RECEIPT AND ACCEPTANCE

This International Depositary accepts the microorganism identified under I above, which was received by it on Thursday, 12 October 1995 (date of the original deposit)[1]

IV. RECEIPT OF REQUEST FOR CONVERSION

The microorganism identified under I above was received by this International Depositary Authority on not applicable (date of the original deposit) and a request to convert the original deposit to a deposit under the Budapest Treaty was received by it on not applicable (date of receipt of request for conversion)

V. INTERNATIONAL DEPOSITARY AUTHORITY

| Name: Centraalbureau voor Schimmelcultures | Signature(s) of person(s) having the power to represent the International Depositary Authority or of authorized official(s): |
|---|---|
| Address: Oosterstraat 1<br>P.O. Box 273<br>3740 AG BAARN<br>The Netherlands | drs F.M. van Asma<br>dr M.C. Agterberg<br>Date: Monday, 30 October 1995 |

[1] Where Rule 6.4(d) applies, such date is the date on which the status of international depositary authority was acquired.

Form BP/4 (sole page)　　　　　CBS/9107

120

BP/A/11/12
page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| Primalco Ltd, Biotec<br>Valta-akseli<br>05200 Rajamaki<br>Finland<br><br>name and address of the party to whom the viability statement is issued | VIABILITY STATEMENT<br>issued pursuant to Rule 10.2 by the<br>INTERNATIONAL DEPOSITARY AUTHORITY<br>identified on the following page |
|---|---|

| I. DEPOSITOR | II. IDENTIFICATION OF THE MICROORGANISM |
|---|---|
| Name: Primalco Ltd, Biotec<br><br>Address: Valta-akseli<br>05200 Rajamaki<br>Finland | Accession number given by the<br>INTERNATIONAL DEPOSITARY AUTHORITY:<br><br>CBS 689.95<br><br>Date of the deposit or of the transfer:[1]<br><br>Thursday, 12 October 1995 |

| III. VIABILITY STATEMENT |
|---|
| The viability of the microorganism identified under II above was tested on Thursday, 19 October 1995 [2]. On that date, the said microorganism was<br><br>[X] [3] viable<br><br>[ ] [3] no longer viable |

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

121

BP/A/II/12
page 25

| IV. CONDITIONS UNDER WHICH THE VIABILITY HAS BEEN PERFORMED [4] |  |
|---|---|
|  |  |
| V. INTERNATIONAL DEPOSITARY AUTHORITY | |
| Name: Centraalbureau voor Schimmelcultures | Signature(s) of person(s) having the power to represent the International Depositary Authority or of authorized official(s): |
| Address: Oosterstraat 1<br>P.O. Box 273<br>3740 AG BAARN<br>The Netherlands | M C Agter     drs F.M. van Asma<br>               dr M.C. Agterberg<br>Date: Monday, 30 October 1995 |

[4] Fill in if the information has been requested and if the results of the test were negative.

Form BP/9 (second and last page)

| Applicant's or agent's file reference number | 122 | International application No. |
|---|---|---|

INDICATIONS RELATING TO A DEPOSITED MICROORGANISM (PCT Rule 13bis)

A. The indications made below relate to the microorganism referred to in the description
on page  9  line  5-7

B. IDENTIFICATION OF DEPOSIT
Further deposits are identified on an additional sheet [X]

Name of depositary institution

Centraalbureau voor Schimmelcultures

Address of depositary institution (including postal code and country)

Oosterstraat 1
P.O. Box 273
3740 AG BAARN
The Netherlands

| Date of deposit | Accession Number |
|---|---|
| 12 October 1995 | CBS 687.95 |

C. ADDITIONAL INDICATIONS (leave blank if not applicable)
This information is continued on an additional sheet [X]

EP   The microorganism shall be made available as provided in Rule 28(3) and 28(4) of the implementing regulations of EPC.

FI   The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| ☐ This sheet was received with the international application | ☐ This sheet was received by the International Bureau on |
| Authorized officer | Authorized officer |

Form PCT:RO/134 (July 1992)

123

BP/A/II/12
page 14

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| Primalco Ltd, Biotec<br>Valta-akseli<br>05200 Rajamaki<br>Finland<br><br>name and address of depositor | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |
|---|---|

I. IDENTIFICATION OF THE MICROORGANISM

| Identification reference given by the DEPOSITOR:<br><br>ALKO4124 | Accession number given by the INTERNATIONAL DEPOSITARY AUTHORITY:<br><br>CBS 687.95 |
|---|---|

II. SCIENTIFIC DESCRIPTION AND/OR PROPOSED TAXONOMIC DESIGNATION

The microorganism identified under I above was accompanied by:

[X] a scientific description

[ ] a proposed taxonomic designation (mark with a cross where applicable)

III. RECEIPT AND ACCEPTANCE

This International Depositary accepts the microorganism identified under I above, which was received by it on Thursday, 12 October 1995          (date of the original deposit)[1]

IV. RECEIPT OF REQUEST FOR CONVERSION

The microorganism identified under I above was received by this International Depositary Authority on not applicable          (date of the original deposit) and a request to convert the original deposit to a deposit under the Budapest Treaty was received by it on not applicable          (date of receipt of request for conversion)

V. INTERNATIONAL DEPOSITARY AUTHORITY

| Name: Centraalbureau voor Schimmelcultures<br><br>Address: Oosterstraat 1<br>P.O. Box 273<br>3740 AG BAARN<br>The Netherlands | Signature(s) of person(s) having the power to represent the International Depositary Authority or of authorized official(s):<br><br>drs F.M. van Asma<br>dr M.C. Agterberg<br><br>Date: Monday, 30 October 1995 |
|---|---|

[1] Where Rule 6.4(d) applies, such date is the date on which the status of international depositary authority was acquired.

Form BP/4   (sole page)

124

BP/A/II/12
page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| Primalco Ltd, Biotec<br>Valta-akseli<br>05200 Rajamaki<br>Finland<br><br>name and address of the party to whom the<br>viability statement is issued | VIABILITY STATEMENT<br>issued pursuant to Rule 10.2 by the<br>INTERNATIONAL DEPOSITARY AUTHORITY<br>identified on the following page |
|---|---|

| I. DEPOSITOR | II. IDENTIFICATION OF THE MICROORGANISM |
|---|---|
| Name: Primalco Ltd, Biotec<br><br>Address: Valta-akseli<br>05200 Rajamaki<br>Finland | Accession number given by the<br>INTERNATIONAL DEPOSITARY AUTHORITY:<br><br>CBS 687.95<br><br>Date of the deposit or of the transfer:[1]<br><br>Thursday, 12 October 1995 |

| III. VIABILITY STATEMENT |
|---|
| The viability of the microorganism identified under II above was tested on Thursday, 19 October 1995  [2]. On that date, the said microorganism was<br><br>[X][3] viable<br><br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9   (first page)

BP/A/II/10
page 25

| IV. CONDITIONS UNDER WHICH THE VIABILITY HAS BEEN PERFORMED [4] |  |
|---|---|
|  |  |
| V. INTERNATIONAL DEPOSITARY AUTHORITY |  |
| Name: Centraalbureau voor Schimmelcultures | Signature(s) of person(s) having the power to represent the International Depository Authority or of authorized official(s): |
| Address: Oosterstraat 1<br>P.O. Box 273<br>3740 AG BAARN<br>The Netherlands | drs F.M. van Asma<br>dr M.C. Agterberg<br>Date: Monday, 30 October 1995 |

[4] Fill in if the information has been requested and if the results of the test were negative.

Form BP/9 (second and last page)

| Applicant's or agent's file reference number | 126 | International application No. |
|---|---|---|

INDICATIONS RELATING TO A DEPOSITED MICROORGANISM (PCT Rule 13bis)

A. The indications made below relate to the microorganism referred to in the description on page _____9_____ , line _____8-11_____

B. IDENTIFICATION OF DEPOSIT           Further deposits are identified on an additional sheet [X]

Name of depositary institution

Centraalbureau voor Schimmelcultures

Address of depositary institution (including postal code and country)

Oosterstraat 1
P.O. Box 273
3740 AG BAARN
The Netherlands

Date of deposit: 11 October 1995

Accession Number: CBS 685.95

C. ADDITIONAL INDICATIONS (leave blank if not applicable)    This information is continued on an additional sheet [X]

EP    The microorganism shall be made available as provided in Rule 28(3) and 28(4) of the implementing regulations of EPC.

FI    The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g. "Accession Number of Deposit")

For receiving Office use only

☐ This sheet was received with the international application

Authorized officer

For International Bureau use only

☐ This sheet was received by the International Bureau on

Authorized officer

Form PCT/RO/134 (July 1992)

BP/A/II/12
page 14

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| |
|---|
| Primalco Ltd, Biotec<br>Valta-akseli<br>05200 Rajamaki<br>Finland<br><br>name and address of depositor |

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR:<br><br>ALKO4237 | Accession number given by the INTERNATIONAL DEPOSITARY AUTHORITY:<br><br>CBS 685.95 |

| II. SCIENTIFIC DESCRIPTION AND/OR PROPOSED TAXONOMIC DESIGNATION |
|---|
| The microorganism identified under I above was accompanied by:<br>[X] a scientific description<br>[ ] a proposed taxonomic designation<br>(mark with a cross where applicable) |

| III. RECEIPT AND ACCEPTANCE |
|---|
| This International Depositary accepts the microorganism identified under I above, which was received by it on Wednesday, 11 October 1995 (date of the original deposit)[1] |

| IV. RECEIPT OF REQUEST FOR CONVERSION |
|---|
| The microorganism identified under I above was received by this International Depositary Authority on not applicable (date of the original deposit) and a request to convert the original deposit to a deposit under the Budapest Treaty was received by it on not applicable (date of receipt of request for conversion) |

| V. INTERNATIONAL DEPOSITARY AUTHORITY | |
|---|---|
| Name: Centraalbureau voor Schimmelcultures<br><br>Address: Oosterstraat 1<br>P.O. Box 273<br>3740 AG BAARN<br>The Netherlands | Signature(s) of person(s) having the power to represent the International Depositary Authority or of authorized official(s):<br><br>drs F.M. van Asma<br>dr M.C. Agterberg<br><br>Date: Monday, 30 October 1995 |

[1] Where Rule 6.4(d) applies, such date is the date on which the status of international depositary authority was acquired.

Form BP/4 (sole page)         CBS/9107

BP/A/II/12
page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| | |
|---|---|
| Primalco Ltd, Biotec<br>Valta-akseli<br>05200 Rajamaki<br>Finland<br><br>name and address of the party to whom the viability statement is issued | VIABILITY STATEMENT<br>issued pursuant to Rule 10.2 by the<br>INTERNATIONAL DEPOSITARY AUTHORITY<br>identified on the following page |

| I. DEPOSITOR | II. IDENTIFICATION OF THE MICROORGANISM |
|---|---|
| Name: Primalco Ltd, Biotec<br><br>Address: Valta-akseli<br>05200 Rajamaki<br>Finland | Accession number given by the<br>INTERNATIONAL DEPOSITARY AUTHORITY:<br><br>CBS 685.95<br><br>Date of the deposit or of the transfer:[1]<br><br>Wednesday, 11 October 1995 |

| III. VIABILITY STATEMENT |
|---|
| The viability of the microorganism identified under II above was tested on Tuesday, 24 October 1995 [2]. On that date, the said microorganism was<br><br>[X][3] viable<br><br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

129

BP/A/II/12
page 25

| IV. CONDITIONS UNDER WHICH THE VIABILITY HAS BEEN PERFORMED [4] |  |
|---|---|
|  |  |
| V. INTERNATIONAL DEPOSITARY AUTHORITY |  |
| Name: Centraalbureau voor Schimmelcultures | Signature(s) of person(s) having the power to represent the International Depositary Authority or of authorized official(s): |
| Address: Oosterstraat 1<br>P.O. Box 273<br>3740 AG BAARN<br>The Netherlands | drs F.M. van Asma<br>dr M.C. Agterberg<br>Date: Monday, 30 October 1995 |

[4] Fill in if the information has been requested and if the results of the test were negative.

Form BP/9 (second and last page)

| Applicant's or agent's file reference number | International application No. |

INDICATIONS RELATING TO A DEPOSITED MICROORGANISM (PCT Rule 13bis)

A. The indications made below relate to the microorganism referred to in the description
on page __9__, line __12-14__

B. IDENTIFICATION OF DEPOSIT
Further deposits are identified on an additional sheet [X]

Name of depositary institution

Centraalbureau voor Schimmelcultures

Address of depositary institution (including postal code and country)

Oosterstraat 1
P.O. Box 273
3740 AG BAARN
The Netherlands

| Date of deposit | Accession Number |
|---|---|
| 12 October 1995 | CBS 688.95 |

C. ADDITIONAL INDICATIONS (leave blank if not applicable)
This information is continued on an additional sheet [X]

EP   The microorganism shall be made available as provided in Rule 28(3) and 28(4) of the implementing regulations of EPC.

FI   The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

---

For receiving Office use only
[ ] This sheet was received with the international application Authorized officer For International Bureau use only
[ ] This sheet was received by the International Bureau on Authorized officer Form PCT/RO/134 (July 1992)

BP/A/II/12
page 14

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| | |
|---|---|
| Primalco Ltd, Biotec<br>Valta-akseli<br>05200 Rajamaki<br>Finland<br><br>*name and address of depositor* | RECEIPT IN THE CASE OF AN ORIGINAL DEPOSIT issued pursuant to Rule 7.1 by the INTERNATIONAL DEPOSITARY AUTHORITY identified at the bottom of this page |

| I. IDENTIFICATION OF THE MICROORGANISM | |
|---|---|
| Identification reference given by the DEPOSITOR:<br><br>ALKO4125 | Accession number given by the INTERNATIONAL DEPOSITARY AUTHORITY:<br><br>CBS 688.95 |

| II. SCIENTIFIC DESCRIPTION AND/OR PROPOSED TAXONOMIC DESIGNATION |
|---|
| The microorganism identified under I above was accompanied by:<br>[X] a scientific description<br>[ ] a proposed taxonomic designation<br>*(mark with a cross where applicable)* |
| III. RECEIPT AND ACCEPTANCE |
| This International Depositary accepts the microorganism identified under I above, which was received by it on Thursday, 12 October 1995  *(date of the original deposit)*[1] |
| IV. RECEIPT OF REQUEST FOR CONVERSION |
| The microorganism identified under I above was received by this International Depositary Authority on not applicable  *(date of the original deposit)* and a request to convert the original deposit to a deposit under the Budapest Treaty was received by it on not applicable  *(date of receipt of request for conversion)* |

| V. INTERNATIONAL DEPOSITARY AUTHORITY | |
|---|---|
| Name: Centraalbureau voor Schimmelcultures<br><br>Address: Oosterstraat 1<br>P.O. Box 273<br>3740 AG BAARN<br>The Netherlands | Signature(s) of person(s) having the power to represent the International Depositary Authority or of authorized official(s):<br><br>drs F.M. van Asma<br>dr M.C. Agterberg<br>Date: Monday, 30 October 1995 |

[1] Where Rule 6.4(d) applies, such date is the date on which the status of international depositary authority was acquired.

Form BP/4 (sole page)  CBS/9107

BP/A/II/12
page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| Primalco Ltd, Biotec<br>Valta-akseli<br>05200 Rajamaki<br>Finland<br><br>*name and address of the party to whom the viability statement is issued* | VIABILITY STATEMENT<br>issued pursuant to Rule 10.2 by the<br>INTERNATIONAL DEPOSITARY AUTHORITY<br>identified on the following page |

| I. DEPOSITOR | II. IDENTIFICATION OF THE MICROORGANISM |
|---|---|
| Name: Primalco Ltd, Biotec<br><br>Address: Valta-akseli<br>05200 Rajamaki<br>Finland | Accession number given by the<br>INTERNATIONAL DEPOSITARY AUTHORITY:<br><br>CBS 688.95<br><br>Date of the deposit or of the transfer:[1]<br><br>Thursday, 12 October 1995 |

| III. VIABILITY STATEMENT |
|---|
| The viability of the microorganism identified under II above was tested on Thursday, 19 October 1995  [2]. On that date, the said microorganism was<br><br>[X][3] viable<br><br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

133

BP/A/II/12
page 25

| IV. CONDITIONS UNDER WHICH THE VIABILITY HAS BEEN PERFORMED [4] |  |
|---|---|
| | |

| V. INTERNATIONAL DEPOSITARY AUTHORITY | |
|---|---|
| Name: Centraalbureau voor Schimmelcultures | Signature(s) of person(s) having the power to represent the International Depositary Authority or of authorized official(s): |
| Address: Oosterstraat 1<br>P.O. Box 273<br>3740 AG BAARN<br>The Netherlands | drs F.M. van Asma<br>dr M.C. Agterberg<br>Date: Monday, 30 October 1995 |

[4] Fill in if the information has been requested and if the results of the test were negative.

Form BP/9 (second and last page)

| Applicant's or agent's file reference number | International application No. |
|---|---|

INDICATIONS RELATING TO A DEPOSITED MICROORGANISM (PCT Rule 13bis)

A. The indications made below relate to the microorganism referred to in the description
on page __9__, line __15-17__

B. IDENTIFICATION OF DEPOSIT
Further deposits are identified on an additional sheet [X]

Name of depositary institution

Centraalbureau voor Schimmelcultures

Address of depositary institution (including postal code and country)

Oosterstraat 1
P.O. Box 273
3740 AG BAARN
The Netherlands

| Date of deposit | Accession Number |
|---|---|
| 8 November 1995 | CBS 730.95 |

C. ADDITIONAL INDICATIONS (leave blank if not applicable)
This information is continued on an additional sheet [X]

EP   The microorganism shall be made available as provided in Rule 28(3) and 28(4) of the implementing regulations of EPC.

FI   The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g. "Accession Number of Deposit")

| For receiving Office use only | For International Bureau use only |
|---|---|
| [ ] This sheet was received with the international application | [ ] This sheet was received by the International Bureau on |
| Authorized officer | Authorized officer |

Form PCT/RO/134 (July 1992)

BP/A/II/12
page 14

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| Primalco Ltd, Biotec<br>Valta-akseli<br>05200 Rajamaki<br>Finland<br><br>name and address of depositor | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |
|---|---|

| I. IDENTIFICATION OF THE MICROORGANISM | |
|---|---|
| Identification reference given by the DEPOSITOR:<br><br>ALKO4265 | Accession number given by the INTERNATIONAL DEPOSITARY AUTHORITY:<br><br>CBS 730.95 |

| II. SCIENTIFIC DESCRIPTION AND/OR PROPOSED TAXONOMIC DESIGNATION |
|---|
| The microorganism identified under I above was accompanied by:<br>☐ a scientific description<br>☒ a proposed taxonomic designation<br>(mark with a cross where applicable) |

| III. RECEIPT AND ACCEPTANCE |
|---|
| This International Depositary accepts the microorganism identified under I above, which was received by it on Wednesday, 8 November 1995  (date of the original deposit)[1] |

| IV. RECEIPT OF REQUEST FOR CONVERSION |
|---|
| The microorganism identified under I above was received by this International Depositary Authority on not applicable  (date of the original deposit) and a request to convert the original deposit to a deposit under the Budapest Treaty was received by it on not applicable  (date of receipt of request for conversion) |

| V. INTERNATIONAL DEPOSITARY AUTHORITY | |
|---|---|
| Name: Centraalbureau voor Schimmelcultures<br><br>Address: Oosterstraat 1<br>P.O. Box 273<br>3740 AG BAARN<br>The Netherlands | Signature(s) of person(s) having the power to represent the International Depositary Authority or of authorized official(s):<br><br>drs F.M. van Asma<br>dr M.C. Agterberg<br><br>Date: Monday, 20 November 1995 |

[1] Where Rule 6.4(d) applies, such date is the date on which the status of international depositary authority was acquired.

Form BP/4 (sole page)  CBS/9107

136

BP/A/II/12
page 24

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

| Primalco Ltd, Biotec<br>Valta-akseli<br>05200 Rajamaki<br>Finland<br><br>name and address of the party to whom the viability statement is issued | VIABILITY STATEMENT<br>issued pursuant to Rule 10.2 by the<br>INTERNATIONAL DEPOSITARY AUTHORITY<br>identified on the following page |
|---|---|

| I. DEPOSITOR | II. IDENTIFICATION OF THE MICROORGANISM |
|---|---|
| Name: Primalco Ltd, Biotec<br><br>Address: Valta-akseli<br>05200 Rajamaki<br>Finland | Accession number given by the<br>INTERNATIONAL DEPOSITARY AUTHORITY:<br><br>CBS 730.95<br><br>Date of the deposit or of the transfer:[1]<br><br>Wednesday, 8 November 1995 |

| III. VIABILITY STATEMENT |
|---|
| The viability of the microorganism identified under II above was tested on Monday, 20 November 1995 [2]. On that date, the said microorganism was<br><br>[X][3] viable<br><br>[ ][3] no longer viable |

[1] Indicate the date of the original deposit or, where a new deposit or a transfer has been made, the most recent relevant date (date of the new deposit or date of the transfer).

[2] In the cases referred to in Rule 10.2(a)(ii) and (iii), refer to the most recent viability test.

[3] Mark with a cross the applicable box.

Form BP/9 (first page)

BP/A/II/12
page 25

| IV. CONDITIONS UNDER WHICH THE VIABILITY HAS BEEN PERFORMED [4] |  |
|---|---|
| | |
| V. INTERNATIONAL DEPOSITARY AUTHORITY | |
| Name: Centraalbureau voor Schimmelcultures | Signature(s) of person(s) having the power to represent the International Depositary Authority or of authorized official(s): |
| Address: Oosterstraat 1<br>P.O. Box 273<br>3740 AG BAARN<br>The Netherlands | drs F.M. van Asma<br>dr M.C. Agterberg<br><br>Date: Monday, 20 November 1995 |

[4] Fill in if the information has been requested and if the results of the test were negative.

Form BP/9 (second and last page)

INDICATIONS RELATING TO A DEPOSITED MICROORGANISM (PCT Rule 13bis)

A. The indications made below relate to the microorganism referred to in the description on page ___9___, line ___18-22___

B. IDENTIFICATION OF DEPOSIT  Further deposits are identified on an additional sheet [X]

Name of depositary institution: DSMZ-DEUTSCHE SAMMLUNG VON MIKROORGANISMEN UND ZELLKULTUREN GmbH Address of depositary institution (including postal code and country):
Mascheroder Weg 1b
D-38124 Braunschweig Date of deposit: 21 June 1996

Accession Number: DSM 11024

C. ADDITIONAL INDICATIONS (leave blank if not applicable)  This information is continued on an additional sheet [X]

EP  The microorganism shall be made available as provided in Rule 28(3) and 28(4) of the implementing regulations of EPC.

FI  The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

139

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR:<br><br>pALK1221 | Accession number given by the<br>INTERNATIONAL DEPOSITARY AUTHORITY:<br><br>DSM 11024 |

| II. SCIENTIFIC DESCRIPTION AND/OR PROPOSED TAXONOMIC DESIGNATION |
|---|
| The microorganism identified under I. above was accompanied by:<br><br>    (X)    a scientific description<br>    ( )    a proposed taxonomic designation<br><br>(Mark with a cross where applicable). |

| III. RECEIPT AND ACCEPTANCE |
|---|
| This International Depositary Authority accepts the microorganism identified under I. above, which was received by it on 1996-06-21 (Date of the original deposit)¹. |

| IV. RECEIPT OF REQUEST FOR CONVERSION |
|---|
| The microorganism identified under I above was received by this International Depositary Authority on (date of original deposit) and a request to convert the original deposit to a deposit under the Budapest Treaty was received by it on (date of receipt of request for conversion). |

| V. INTERNATIONAL DEPOSITARY AUTHORITY | |
|---|---|
| Name:    DSMZ-DEUTSCHE SAMMLUNG VON<br>              MIKROORGANISMEN UND ZELLKULTUREN GmbH<br><br>Address: Mascheroder Weg 1b<br>            D-38124 Braunschweig | Signature(s) of person(s) having the power to represent the International Depositary Authority or of authorized official(s):<br><br>*U. Weihs*<br><br>Date: 1996-06-27 |

¹ Where Rule 6.4 (d) applies, such date is the date on which the status of international depositary authority was acquired.

Form DSMZ-BP/4 (sole page) 0196

140

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

VIABILITY STATEMENT
issued pursuant to Rule 10.2 by the
INTERNATIONAL DEPOSITARY AUTHORITY
identified at the bottom of this page

| I. DEPOSITOR | II. IDENTIFICATION OF THE MICROORGANISM |
|---|---|
| Name: Primalco Ltd. Biotec Valta-Akseli<br>Address: FIN-05200 Rajamäki | Accession number given by the INTERNATIONAL DEPOSITARY AUTHORITY:<br>DSM 11024<br><br>Date of the deposit or the transfer[1]:<br>1996-06-21 |

| III. VIABILITY STATEMENT |
|---|
| The viability of the microorganism identified under II above was tested on 1996-06-26 [2].<br>On that date, the said microorganism was<br><br>(X)[3]  viable<br><br>( )[3]  no longer viable |

| IV. CONDITIONS UNDER WHICH THE VIABILITY TEST HAS BEEN PERFORMED[4] |
|---|
|  |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH<br><br>Address: Mascheroder Weg 1b<br>D-38124 Braunschweig | Signature(s) of person(s) having the power to represent the International Depositary Authority or of authorized official(s):<br><br>*signature*<br><br>Date: 1996-06-27 |

[1] Indicate the date of original deposit or, where a new deposit or a transfer has been made, the most recent relevant date (date of the new deposit or date of the transfer).
[2] In the cases referred to in Rule 10.2(a) (ii) and (iii), refer to the most recent viability test.
[3] Mark with a cross the applicable box.
[4] Fill in if the information has been requested and if the results of the test were negative.

Form DSMZ-BP/9 (sole page) 0196

141

| Applicant's or agent's file reference number | International Application No. |

INDICATIONS RELATING TO A DEPOSITED MICROORGANISM (PCT Rule 13bis)

A. The indications made below relate to the microorganism referred to in the description
on page __9__ line __19-22__

B. IDENTIFICATION OF DEPOSIT   Further deposits are identified on an additional sheet [x]

Name of depositary institution
DSMZ-DEUTSCHE SAMMLUNG VON MIKROORGANISMEN UND ZELLKULTUREN GmbH Address of depositary institution (including postal code and country)

Mascheroder Weg 1b
D-38124 Braunschweig

Date of deposit: 21 June 1996

Accession Number: DSM 11012

C. ADDITIONAL INDICATIONS (leave blank if not applicable)   This information is continued on an additional sheet [X]

EP  The microorganism shall be made available as provided in Rule 28(3) and 28(4) of the implementing regulations of EPC.

FI  The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g. "Accession Number of Deposit")

For receiving Office use only
[ ] This sheet was received with the international application
Authorized officer For International Bureau use only
[ ] This sheet was received by the International Bureau on:
Authorized officer Form PCT/RO/134 (July 1992)

142

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: <br><br> lambda 4237/5.1 | Accession number given by the <br> INTERNATIONAL DEPOSITARY AUTHORITY: <br><br> DSM 11012 |

| II. SCIENTIFIC DESCRIPTION AND/OR PROPOSED TAXONOMIC DESIGNATION |
|---|
| The microorganism identified under I. above was accompanied by: <br><br> (X) a scientific description <br> ( ) a proposed taxonomic designation <br><br> (Mark with a cross where applicable). |

| III. RECEIPT AND ACCEPTANCE |
|---|
| This International Depositary Authority accepts the microorganism identified under I. above, which was received by it on 1996-06-21 (Date of the original deposit)¹. |

| IV. RECEIPT OF REQUEST FOR CONVERSION |
|---|
| The microorganism identified under I above was received by this International Depositary Authority on (date of original deposit) and a request to convert the original deposit to a deposit under the Budapest Treaty was received by it on (date of receipt of request for conversion). |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH <br><br> Address: Mascheroder Weg 1b <br> D-38124 Braunschweig | Signature(s) of person(s) having the power to represent the International Depositary Authority or of authorized official(s): <br><br> U. Wels <br><br> Date: 1996-06-27 |

¹ Where Rule 6.4 (d) applies, such date is the date on which the status of international depositary authority was acquired.

Form DSMZ-BP/4 (sole page) 0196

143

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

VIABILITY STATEMENT
issued pursuant to Rule 10.2 by the
INTERNATIONAL DEPOSITARY AUTHORITY
identified at the bottom of this page

| I. DEPOSITOR | II. IDENTIFICATION OF THE MICROORGANISM |
|---|---|
| Name: Primalco Ltd. Biotec Valta-Akseli<br>Address: FIN-05200 Rajamäki | Accession number given by the INTERNATIONAL DEPOSITARY AUTHORITY:<br>DSM 11012<br><br>Date of the deposit or the transfer[1]:<br>1996-06-21 |

| III. VIABILITY STATEMENT |
|---|
| The viability of the microorganism identified under II above was tested on 1996-06-24 [2].<br>On that date, the said microorganism was<br><br>(X)[3] viable<br><br>( )[3] no longer viable |

| IV. CONDITIONS UNDER WHICH THE VIABILITY TEST HAS BEEN PERFORMED[4] |
|---|
|  |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH<br>Address: Mascheroder Weg 1b<br>D-38124 Braunschweig | Signature(s) of person(s) having the power to represent the International Depositary Authority or of authorized official(s):<br><br>*U. Weis*<br><br>Date: 1996-06-27 |

[1] Indicate the date of original deposit or, where a new deposit or a transfer has been made, the most recent relevant date (date of the new deposit or date of the transfer).
[2] In the cases referred to in Rule 10.2(a) (ii) and (iii), refer to the most recent viability test.
[3] Mark with a cross the applicable box.
[4] Fill in if the information has been requested and if the results of the test were negative.

Form DSMZ-BP/9 (sole page) 0196

| Applicant's or agent's file reference number | 144 | International application No. |
|---|---|---|

INDICATIONS RELATING TO A DEPOSITED MICROORGANISM (PCT Rule 13bis)

A. The indications made below relate to the microorganism referred to in the description
on page  9  , line  23-27

B. IDENTIFICATION OF DEPOSIT  Further deposits are identified on an additional sheet [x]

Name of depositary institution
DSMZ-DEUTSCHE SAMMLUNG VON
MIKROORGANISMEN UND ZELLKULTUREN GmbH Address of depositary institution (including postal code and country)
Mascheroder Weg 1b
D-38124 Braunschweig

| Date of deposit | Accession Number |
|---|---|
| 21 June 1996 | 11025 |

C. ADDITIONAL INDICATIONS (leave blank if not applicable)  This information is continued on an additional sheet [X]

EP    The microorganism shall be made available as provided in Rule 28(3) and 28(4) of the implementing regulations of EPC.

FI    The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g. "Accession Number of Deposit")

| For receiving Office use only | For International Bureau use only |
|---|---|
| [ ] This sheet was received with the international application | [ ] This sheet was received by the International Bureau on |
| Authorized officer | Authorized officer |

Form PCT/RO/134 (July 1992)

145

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR:<br>pALK1227 | Accession number given by the<br>INTERNATIONAL DEPOSITARY AUTHORITY:<br>DSM 11025 |

| II. SCIENTIFIC DESCRIPTION AND/OR PROPOSED TAXONOMIC DESIGNATION |
|---|
| The microorganism identified under I. above was accompanied by:<br><br>(X) a scientific description<br>( ) a proposed taxonomic designation<br><br>(Mark with a cross where applicable). |

| III. RECEIPT AND ACCEPTANCE |
|---|
| This International Depositary Authority accepts the microorganism identified under I. above, which was received by it on 1996-06-21 (Date of the original deposit)¹. |

| IV. RECEIPT OF REQUEST FOR CONVERSION |
|---|
| The microorganism identified under I above was received by this International Depositary Authority on (date of original deposit) and a request to convert the original deposit to a deposit under the Budapest Treaty was received by it on (date of receipt of request for conversion). |

| V. INTERNATIONAL DEPOSITARY AUTHORITY | |
|---|---|
| Name: DSMZ-DEUTSCHE SAMMLUNG VON<br>MIKROORGANISMEN UND ZELLKULTUREN GmbH<br><br>Address: Mascheroder Weg 1b<br>D-38124 Braunschweig | Signature(s) of person(s) having the power to represent the International Depositary Authority or of authorized official(s):<br><br>*signature*<br><br>Date: 1996-06-27 |

¹ Where Rule 6.4 (d) applies, such date is the date on which the status of international depositary authority was acquired.

146

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

VIABILITY STATEMENT
issued pursuant to Rule 10.2 by the
INTERNATIONAL DEPOSITARY AUTHORITY
identified at the bottom of this page

| I. DEPOSITOR | II. IDENTIFICATION OF THE MICROORGANISM |
|---|---|
| Name: Primalco Ltd. Biotec<br>Valta-Akseli<br>Address:<br>FIN-05200 Rajamäki | Accession number given by the<br>INTERNATIONAL DEPOSITARY AUTHORITY:<br>DSM 11025<br><br>Date of the deposit or the transfer[1]:<br>1996-06-21 |

| III. VIABILITY STATEMENT |
|---|
| The viability of the microorganism identified under II above was tested on 1996-06-26 [2].<br>On that date, the said microorganism was<br><br>(X)[3]  viable<br><br>( )[3]  no longer viable |

| IV. CONDITIONS UNDER WHICH THE VIABILITY TEST HAS BEEN PERFORMED[4] |
|---|
|  |

| V. INTERNATIONAL DEPOSITARY AUTHORITY | |
|---|---|
| Name: DSMZ-DEUTSCHE SAMMLUNG VON<br>MIKROORGANISMEN UND ZELLKULTUREN GmbH<br><br>Address: Mascheroder Weg 1b<br>D-38124 Braunschweig | Signature(s) of person(s) having the power to represent the<br>International Depositary Authority or of authorized official(s):<br><br>*signature*<br><br>Date: 1996-06-27 |

[1] Indicate the date of original deposit or, where a new deposit or a transfer has been made, the most recent relevant date (date of the new deposit or date of the transfer).
[2] In the cases referred to in Rule 10.2(a) (ii) and (iii), refer to the most recent viability test.
[3] Mark with a cross the applicable box.
[4] Fill in if the information has been requested and if the results of the test were negative.

Form DSMZ-BP/9 (sole page) 0196

| Applicant's or agent's file reference number | International application No. |
|---|---|
| | |

INDICATIONS RELATING TO A DEPOSITED MICROORGANISM (PCT Rule 13bis)

A. The indications made below relate to the microorganism referred to in the description
on page _____9_____ , line _____24-27_____

B. IDENTIFICATION OF DEPOSIT          Further deposits are identified on an additional sheet [x]

Name of depositary institution
DSMZ-DEUTSCHE SAMMLUNG VON
MIKROORGANISMEN UND ZELLKULTUREN GmbH Address of depositary institution (including postal code and country)

Mascheroder Weg 1b
D-38124 Braunschweig

| Date of deposit | Accession Number |
|---|---|
| 21 June 1996 | DSM 11014 |

C. ADDITIONAL INDICATIONS (leave blank if not applicable)    This information is continued on an additional sheet [X]

EP    The microorganism shall be made available as provided in Rule 28(3) and 28(4) of the implementing regulations of EPC.

FI    The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| [ ] This sheet was received with the international application | [ ] This sheet was received by the International Bureau on: |
| Authorized officer | Authorized officer |

Form PCT/RO/134 (July 1992)

148

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR:<br><br>lambda 4237/35 | Accession number given by the<br>INTERNATIONAL DEPOSITARY AUTHORITY:<br><br>DSM 11014 |

| II. SCIENTIFIC DESCRIPTION AND/OR PROPOSED TAXONOMIC DESIGNATION |
|---|
| The microorganism identified under I. above was accompanied by:<br><br>    (X)   a scientific description<br>    ( )   a proposed taxonomic designation<br><br>(Mark with a cross where applicable). |

| III. RECEIPT AND ACCEPTANCE |
|---|
| This International Depositary Authority accepts the microorganism identified under I. above, which was received by it on 1996-06-21 (Date of the original deposit)[1]. |

| IV. RECEIPT OF REQUEST FOR CONVERSION |
|---|
| The microorganism identified under I above was received by this International Depositary Authority on   (date of original deposit) and a request to convert the original deposit to a deposit under the Budapest Treaty was received by it on   (date of receipt of request for conversion). |

| V. INTERNATIONAL DEPOSITARY AUTHORITY | |
|---|---|
| Name:    DSMZ-DEUTSCHE SAMMLUNG VON<br>              MIKROORGANISMEN UND ZELLKULTUREN GmbH<br><br>Address:  Mascheroder Weg 1b<br>             D-38124 Braunschweig | Signature(s) of person(s) having the power to represent the International Depositary Authority or of authorized official(s):<br><br><br>Date: 1996-06-27 |

[1] Where Rule 6.4 (d) applies, such date is the date on which the status of international depositary authority was acquired.

Form DSMZ-BP/4 (sole page) 0196

149

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

VIABILITY STATEMENT
issued pursuant to Rule 10.2 by the
INTERNATIONAL DEPOSITARY AUTHORITY
identified at the bottom of this page

| I. DEPOSITOR | II. IDENTIFICATION OF THE MICROORGANISM |
|---|---|
| Name: Primalco Ltd. Biotec Valta-Akseli<br>Address: FIN-05200 Rajamäki | Accession number given by the INTERNATIONAL DEPOSITARY AUTHORITY:<br>DSM 11014<br><br>Date of the deposit or the transfer[1]:<br>1996-06-21 |

| III. VIABILITY STATEMENT |
|---|
| The viability of the microorganism identified under II above was tested on 1996-06-24 [2].<br>On that date, the said microorganism was<br><br>(X)[3] viable<br><br>( )[3] no longer viable |

| IV. CONDITIONS UNDER WHICH THE VIABILITY TEST HAS BEEN PERFORMED[4] |
|---|
|  |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH<br><br>Address: Mascheroder Weg 1b<br>D-38124 Braunschweig | Signature(s) of person(s) having the power to represent the International Depositary Authority or of authorized official(s):<br><br>U. Wutz<br><br>Date: 1996-06-27 |

[1] Indicate the date of original deposit or, where a new deposit or a transfer has been made, the most recent relevant date (date of the new deposit or date of the transfer).
[2] In the cases referred to in Rule 10.2(a) (ii) and (iii), refer to the most recent viability test.
[3] Mark with a cross the applicable box.
[4] Fill in if the information has been requested and if the results of the test were negative.

Form DSMZ-BP/9 (sole page) 0196

| Applicant's or agent's file reference number | International application No. |
|---|---|

INDICATIONS RELATING TO A DEPOSITED MICROORGANISM (PCT Rule 13bis)

A. The indications made below relate to the microorganism referred to in the description
on page 9 and 10, line 28-30, 1-4

B. IDENTIFICATION OF DEPOSIT  Further deposits are identified on an additional sheet [X]

Name of depositary institution
DSMZ-DEUTSCHE SAMMLUNG VON
MIKROORGANISMEN UND ZELLKULTUREN GmbH Address of depositary institution *(including postal code and country)*
Mascheroder Weg 1b
D-38124 Braunschweig

| Date of deposit | Accession Number |
|---|---|
| 21 June 1996 | 11026 |

C. ADDITIONAL INDICATIONS *(leave blank if not applicable)*  This information is continued on an additional sheet [X]

EP    The microorganism shall be made available as provided in Rule 28(3) and 28(4) of the implementing regulations of EPC.

FI    The microorganism shall be made available as provided in Finnish Patent Law 22 § 7.

Enclosed recognition of receipt and viability statement

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g. "Accession Number of Deposit")*

| For receiving Office use only | For International Bureau use only |
|---|---|
| ☐ This sheet was received with the international application | ☐ This sheet was received by the International Bureau on |
| Authorized officer | Authorized officer |

Form PCT/RO/134 (July 1992)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

RECEIPT IN THE CASE OF AN ORIGINAL DEPOSIT
issued pursuant to Rule 7.1 by the
INTERNATIONAL DEPOSITARY AUTHORITY
identified at the bottom of this page

I. IDENTIFICATION OF THE MICROORGANISM

| Identification reference given by the DEPOSITOR: | Accession number given by the INTERNATIONAL DEPOSITARY AUTHORITY: |
|---|---|
| pALK1229 | DSM 11026 |

II. SCIENTIFIC DESCRIPTION AND/OR PROPOSED TAXONOMIC DESIGNATION

The microorganism identified under I. above was accompanied by:

(X) a scientific description
      ( ) a proposed taxonomic designation (Mark with a cross where applicable).

III. RECEIPT AND ACCEPTANCE

This International Depositary Authority accepts the microorganism identified under I. above, which was received by it on 1996-06-21 (Date of the original deposit)[1].

IV. RECEIPT OF REQUEST FOR CONVERSION

The microorganism identified under I above was received by this International Depositary Authority on (date of original deposit) and a request to convert the original deposit to a deposit under the Budapest Treaty was received by it on (date of receipt of request for conversion).

V. INTERNATIONAL DEPOSITARY AUTHORITY

| | |
|---|---|
| Name: DSMZ-DEUTSCHE SAMMLUNG VON MIKROORGANISMEN UND ZELLKULTUREN GmbH<br><br>Address: Mascheroder Weg 1b<br>D-38124 Braunschweig | Signature(s) of person(s) having the power to represent the International Depositary Authority or of authorized official(s):<br><br>Date: 1996-06-27 |

[1] Where Rule 6.4 (d) applies, such date is the date on which the status of international depositary authority was acquired.

Form DSMZ-BP/4 (sole page) 0196

152

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

VIABILITY STATEMENT
issued pursuant to Rule 10.2 by the
INTERNATIONAL DEPOSITARY AUTHORITY
identified at the bottom of this page

| I. DEPOSITOR | II. IDENTIFICATION OF THE MICROORGANISM |
|---|---|
| Name: Primalco Ltd. Biotec Valta-Akseli<br>Address: FIN-05200 Rajamäki | Accession number given by the INTERNATIONAL DEPOSITARY AUTHORITY:<br>DSM 11026<br><br>Date of the deposit or the transfer[1]:<br>1996-06-21 |

| III. VIABILITY STATEMENT |
|---|
| The viability of the microorganism identified under II above was tested on 1996-06-26 [2].<br>On that date, the said microorganism was<br><br>   (X)[3] viable<br><br>   ( )[3] no longer viable |

| IV. CONDITIONS UNDER WHICH THE VIABILITY TEST HAS BEEN PERFORMED[4] |
|---|
|  |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH<br><br>Address: Mascheroder Weg 1b<br>D-38124 Braunschweig | Signature(s) of person(s) having the power to represent the International Depositary Authority or of authorized official(s):<br><br>Date: 1996-06-27 |

[1] Indicate the date of original deposit or, where a new deposit or a transfer has been made, the most recent relevant date (date of the new deposit or date of the transfer).
[2] In the cases referred to in Rule 10.2(a) (ii) and (iii), refer to the most recent viability test.
[3] Mark with a cross the applicable box.
[4] Fill in if the information has been requested and if the results of the test were negative.

Form DSMZ-BP/9 (sole page) 0196

| Applicant's or agent's file reference number | 153 | International application No. |
|---|---|---|

INDICATIONS RELATING TO A DEPOSITED MICROORGANISM (PCT Rule 13bis)

A. The indications made below relate to the microorganism referred to in the description
on page __9 and 10__ , line __29, 1-4__

B. IDENTIFICATION OF DEPOSIT    Further deposits are identified on an additional sheet [x]

Name of depositary institution
DSMZ-DEUTSCHE SAMMLUNG VON
MIKROORGANISMEN UND ZELLKULTUREN GmbH Address of depositary institution (including postal code and country)
Mascheroder Weg 1b
D-38124 Braunschweig

| Date of deposit | Accession Number |
|---|---|
| 21 June 1996 | 11011 |

C. ADDITIONAL INDICATIONS (leave blank if not applicable)    This information is continued on an additional sheet [X]

EP   The microorganism shall be made available as provided in Rule 28(3) and 28(4) of the implementing regulations of EPC.

FI   The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g. "Accession Number of Deposit")

| For receiving Office use only | For International Bureau use only |
|---|---|
| ☐ This sheet was received with the international application | ☐ This sheet was received by the International Bureau on |
| Authorized officer | Authorized officer |

Form PCT/RO/134 (July 1992)

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: <br><br> lambda 4237/3 | Accession number given by the INTERNATIONAL DEPOSITARY AUTHORITY: <br><br> DSM 11011 |

| II. SCIENTIFIC DESCRIPTION AND/OR PROPOSED TAXONOMIC DESIGNATION |
|---|
| The microorganism identified under I. above was accompanied by: <br><br> (X) a scientific description <br> ( ) a proposed taxonomic designation <br><br> (Mark with a cross where applicable). |

| III. RECEIPT AND ACCEPTANCE |
|---|
| This International Depositary Authority accepts the microorganism identified under I. above, which was received by it on 1996-06-21 (Date of the original deposit)[1]. |

| IV. RECEIPT OF REQUEST FOR CONVERSION |
|---|
| The microorganism identified under I above was received by this International Depositary Authority on (date of original deposit) and a request to convert the original deposit to a deposit under the Budapest Treaty was received by it on (date of receipt of request for conversion). |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH <br><br> Address: Mascheroder Weg 1b <br> D-38124 Braunschweig | Signature(s) of person(s) having the power to represent the International Depositary Authority or of authorized official(s): <br><br> *U. Wats* <br><br> Date: 1996-06-27 |

[1] Where Rule 6.4 (d) applies, such date is the date on which the status of international depositary authority was acquired.

Form DSMZ-BP/4 (sole page) 0196

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

VIABILITY STATEMENT
issued pursuant to Rule 10.2 by the
INTERNATIONAL DEPOSITARY AUTHORITY
identified at the bottom of this page

| I. DEPOSITOR | II. IDENTIFICATION OF THE MICROORGANISM |
|---|---|
| Name: Primalco Ltd. Biotec Valta-Akseli<br>Address: FIN-05200 Rajamäki | Accession number given by the INTERNATIONAL DEPOSITARY AUTHORITY:<br>DSM 11011<br><br>Date of the deposit or the transfer[1]:<br>1996-06-21 |

| III. VIABILITY STATEMENT |
|---|
| The viability of the microorganism identified under II above was tested on 1996-06-24 [2].<br>On that date, the said microorganism was<br><br>(X)[3] viable<br><br>( )[3] no longer viable |

| IV. CONDITIONS UNDER WHICH THE VIABILITY TEST HAS BEEN PERFORMED[4] |
|---|
|  |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH<br>Address: Mascheroder Weg 1b<br>D-38124 Braunschweig | Signature(s) of person(s) having the power to represent the International Depositary Authority or of authorized official(s):<br><br>Date: 1996-06-27 |

[1] Indicate the date of original deposit or, where a new deposit or a transfer has been made, the most recent relevant date (date of the new deposit or date of the transfer).
[2] In the cases referred to in Rule 10.2(a) (ii) and (iii), refer to the most recent viability test.
[3] Mark with a cross the applicable box.
[4] Fill in if the information has been requested and if the results of the test were negative.

Form DSMZ-BP/9 (sole page) 0196

156

| Applicant's or agent's file reference number | | International application No. | |
|---|---|---|---|

INDICATIONS RELATING TO A DEPOSITED MICROORGANISM (PCT Rule 13bis)

A. The indications made below relate to the microorganism referred to in the description
on page __9 and 10__, line __30, 1-4__

B. IDENTIFICATION OF DEPOSIT     Further deposits are identified on an additional sheet [x]

Name of depositary institution
DSMZ-DEUTSCHE SAMMLUNG VON
MIKROORGANISMEN UND ZELLKULTUREN GmbH Address of depositary institution (including postal code and country)
Mascheroder Weg 1b
D-38124 Braunschweig

| Date of deposit | Accession Number |
|---|---|
| 21 June 1996 | DSM 11013 |

C. ADDITIONAL INDICATIONS (leave blank if not applicable)     This information is continued on an additional sheet [X]

EP    The microorganism shall be made available as provided in Rule 28(3) and 28(4) of the implementing regulations of EPC.

FI    The microorganism shall be made available as provided in Finnish Patent Law 22 § 7.

Enclosed recognition of receipt and viability statement

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| [ ] This sheet was received with the international application | [ ] This sheet was received by the International Bureau on |
| Authorized officer | Authorized officer |

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: <br><br> lambda 4237/18 | Accession number given by the <br> INTERNATIONAL DEPOSITARY AUTHORITY: <br><br> DSM 11013 |

| II. SCIENTIFIC DESCRIPTION AND/OR PROPOSED TAXONOMIC DESIGNATION |
|---|
| The microorganism identified under I. above was accompanied by: <br><br> (X) a scientific description <br> ( ) a proposed taxonomic designation <br><br> (Mark with a cross where applicable). |

| III. RECEIPT AND ACCEPTANCE |
|---|
| This International Depositary Authority accepts the microorganism identified under I. above, which was received by it on 1996-06-21 (Date of the original deposit)¹. |

| IV. RECEIPT OF REQUEST FOR CONVERSION |
|---|
| The microorganism identified under I above was received by this International Depositary Authority on (date of original deposit) and a request to convert the original deposit to a deposit under the Budapest Treaty was received by it on (date of receipt of request for conversion). |

| V. INTERNATIONAL DEPOSITARY AUTHORITY | |
|---|---|
| Name: DSMZ-DEUTSCHE SAMMLUNG VON <br> MIKROORGANISMEN UND ZELLKULTUREN GmbH <br><br> Address: Mascheroder Weg 1b <br> D-38124 Braunschweig | Signature(s) of person(s) having the power to represent the International Depositary Authority or of authorized official(s): <br><br> Date: 1996-06-27 |

¹ Where Rule 6.4 (d) applies, such date is the date on which the status of international depositary authority was acquired.

Form DSMZ-BP/4 (sole page) 0196

158

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

VIABILITY STATEMENT
issued pursuant to Rule 10.2 by the
INTERNATIONAL DEPOSITARY AUTHORITY
identified at the bottom of this page

| I. DEPOSITOR | II. IDENTIFICATION OF THE MICROORGANISM |
|---|---|
| Name: Primalco Ltd. Biotec<br>Valta-Akseli<br>Address:<br>FIN-05200 Rajamäki | Accession number given by the<br>INTERNATIONAL DEPOSITARY AUTHORITY:<br>DSM 11013<br><br>Date of the deposit or the transfer[1]:<br>1996-06-21 |

| III. VIABILITY STATEMENT |
|---|
| The viability of the microorganism identified under II above was tested on 1996-06-24 [2].<br>On that date, the said microorganism was<br><br>   (X)[3]  viable<br><br>   (  )[3]  no longer viable |

| IV. CONDITIONS UNDER WHICH THE VIABILITY TEST HAS BEEN PERFORMED[4] |
|---|
| |

| V. INTERNATIONAL DEPOSITARY AUTHORITY | |
|---|---|
| Name: DSMZ-DEUTSCHE SAMMLUNG VON<br>MIKROORGANISMEN UND ZELLKULTUREN GmbH<br><br>Address: Mascheroder Weg 1b<br>D-38124 Braunschweig | Signature(s) of person(s) having the power to represent the<br>International Depositary Authority or of authorized official(s):<br><br>*U. Wets*<br><br>Date: 1996-06-27 |

[1] Indicate the date of original deposit or, where a new deposit or a transfer has been made, the most recent relevant date (date of the new deposit or date of the transfer).
[2] In the cases referred to in Rule 10.2(a) (ii) and (iii), refer to the most recent viability test.
[3] Mark with a cross the applicable box.
[4] Fill in if the information has been requested and if the results of the test were negative.

Form DSMZ-BP/9 (sole page) 0196

INDICATIONS RELATING TO A DEPOSITED MICROORGANISM (PCT Rule 13bis)

| | |
|---|---|
| A. The indications made below relate to the microorganism referred to in the description on page 10, line 5-8 | |
| B. IDENTIFICATION OF DEPOSIT | Further deposits are identified on an additional sheet [X] |

Name of depositary institution
DSMZ-DEUTSCHE SAMMLUNG VON MIKROORGANISMEN UND ZELLKULTUREN GmbH Address of depositary institution *(including postal code and country)*
Mascheroder Weg 1b
D-38124 Braunschweig

| Date of deposit | Accession Number |
|---|---|
| 21 June 1996 | 11027 |

C. ADDITIONAL INDICATIONS *(leave blank if not applicable)* This information is continued on an additional sheet [X]

EP  The microorganism shall be made available as provided in Rule 28(3) and 28(4) of the implementing regulations of EPC.

FI  The microorganism shall be made available as provided in Finnish Patent Law 22 § 7.

Enclosed recognition of receipt and viability statement

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g. "Accession Number of Deposit")*

160

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR:<br><br>pALK1230 | Accession number given by the<br>INTERNATIONAL DEPOSITARY AUTHORITY:<br><br>DSM 11027 |

| II. SCIENTIFIC DESCRIPTION AND/OR PROPOSED TAXONOMIC DESIGNATION |
|---|
| The microorganism identified under I. above was accompanied by:<br><br>(X) a scientific description<br>( ) a proposed taxonomic designation<br><br>(Mark with a cross where applicable). |

| III. RECEIPT AND ACCEPTANCE |
|---|
| This International Depositary Authority accepts the microorganism identified under I. above, which was received by it on 1996-06-21 (Date of the original deposit)¹. |

| IV. RECEIPT OF REQUEST FOR CONVERSION |
|---|
| The microorganism identified under I above was received by this International Depositary Authority on (date of original deposit) and a request to convert the original deposit to a deposit under the Budapest Treaty was received by it on (date of receipt of request for conversion). |

| V. INTERNATIONAL DEPOSITARY AUTHORITY | |
|---|---|
| Name: DSMZ-DEUTSCHE SAMMLUNG VON<br>MIKROORGANISMEN UND ZELLKULTUREN GmbH<br><br>Address: Mascheroder Weg 1b<br>D-38124 Braunschweig | Signature(s) of person(s) having the power to represent the International Depositary Authority or of authorized official(s):<br><br>*signature*<br><br>Date: 1996-06-27 |

¹ Where Rule 6.4 (d) applies, such date is the date on which the status of international depositary authority was acquired.

Form DSMZ-BP/4 (sole page) 0196

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Primalco Ltd. Biotec
Valta-Akseli

FIN-05200 Rajamäki

VIABILITY STATEMENT
issued pursuant to Rule 10.2 by the
INTERNATIONAL DEPOSITARY AUTHORITY
identified at the bottom of this page

| I. DEPOSITOR | II. IDENTIFICATION OF THE MICROORGANISM |
|---|---|
| Name: Primalco Ltd. Biotec<br>Valta-Akseli<br>Address: FIN-05200 Rajamäki | Accession number given by the<br>INTERNATIONAL DEPOSITARY AUTHORITY:<br>DSM 11027<br><br>Date of the deposit or the transfer¹:<br>1996-06-21 |

| III. VIABILITY STATEMENT |
|---|
| The viability of the microorganism identified under II above was tested on 1996-06-26 ².<br>On that date, the said microorganism was<br><br>(X)³ viable<br><br>( )³ no longer viable |

| IV. CONDITIONS UNDER WHICH THE VIABILITY TEST HAS BEEN PERFORMED⁴ |
|---|
|  |

| V. INTERNATIONAL DEPOSITARY AUTHORITY | |
|---|---|
| Name: DSMZ-DEUTSCHE SAMMLUNG VON<br>MIKROORGANISMEN UND ZELLKULTUREN GmbH<br><br>Address: Mascheroder Weg 1b<br>D-38124 Braunschweig | Signature(s) of person(s) having the power to represent the<br>International Depositary Authority or of authorized official(s):<br><br>Date: 1996-06-27 |

¹ Indicate the date of original deposit or, where a new deposit or a transfer has been made, the most recent relevant date (date of the new deposit or date of the transfer).
² In the cases referred to in Rule 10.2(a) (ii) and (iii), refer to the most recent viability test.
³ Mark with a cross the applicable box.
⁴ Fill in if the information has been requested and if the results of the test were negative.

Form DSMZ-BP/9 (sole page) 0196

The invention claimed is:

1. A method for biostoning comprising adding an enzyme preparation comprising a polypeptide having cellulase activity to cotton containing fabric or garments, wherein said polypeptide is selected from the group consisting of:
   (i) a polypeptide comprising the amino acid sequence set forth in FIG. 19 and SEQ ID NO: 31,
   (ii) a polypeptide having at least 95% identity to the amino acid sequence set forth in FIG. 19 and SEQ ID NO: 31,
   (iii) a polypeptide comprising the amino acid sequence encoded by the DNA insert contained in the vector transformed into DSM 11024 or DSM 11012,
   (iv) a polypeptide comprising amino acids 22-235 of the amino acid sequence set forth in FIG. 19 and SEQ ID NO: 31; and
   (v) a polypeptide having at least 95% identity to amino acids 22-235 of the amino acid sequence set forth in FIG. 19 and SEQ ID NO: 31.

2. A method according to claim 1, wherein said polypeptide comprises the amino acid sequence set forth in FIG. 19 and SEQ II) NO: 31.

3. A method according to claim 1, wherein said polypeptide has at least 95% identity to the amino acid sequence set forth in FIG. 19 and SEQ ID NO: 31.

4. A method according to claim 1, wherein said polypeptide comprises the amino acid sequence encoded by the DNA insert contained in the vector transformed into DSM 11024 or DSM 11012.

5. A method according to claim 1, wherein said polypeptide comprises amino acids 22-235 of the amino acid sequence set forth in FIG. 19 and SEQ ID NO: 31.

6. A method according to claim 1, wherein said polypeptide has at least 95% identity to amino acids 22-235 of the amino acid sequence set forth in FIG. 19 and SEQ ID NO: 31.

7. A method according to claim 1, wherein said enzyme preparation is obtained by a process comprising:
   (i) culturing a host cell transformed with the nucleic acid molecule comprising the sequence set forth in FIG. 19 (SEQ ID NO: 30); and
   (ii) separating said host cell from the culture medium and obtaining the supernatant having cellulase activity.

8. A method according to claim 1, wherein said enzyme preparation is obtained by a process comprising:
(i) culturing a host cell transformed with the nucleic acid sequence encoding a cellulase having at least 95% identity to the amino acid sequence set forth in FIG. 19 (SEQ ID NO: 31); and
(ii) separating said host cell from the culture medium and obtaining the supernatant having cellulase activity.

9. A method according to claim 1, wherein said enzyme preparation is obtained by a process comprising:
(i) culturing a host cell transformed with the nucleic acid sequence encoding amino acids 22-235 of the amino acid sequence set forth in FIG. 19 (SEQ ID NO: 31); and
(ii) separating said host cell from the culture medium and obtaining the supernatant having cellulase activity.

10. A method according to claim 1, wherein said enzyme preparation is obtained by a process comprising:
(i) culturing a host cell transformed with the nucleic acid sequence encoding a cellulase having at least 95% identity to amino acids 22-235 of the amino acid sequence set forth in FIG. 19 (SEQ ID NO: 31); and
(ii) separating said host cell from the culture medium and obtaining the supernatant having cellulase activity.

11. A method according to claim 1, wherein said polypeptide is isolated and essentially homogenous.

12. A method according to claim 1, wherein said enzyme preparation comprises at least one cellulase of a fungal species belonging to a fungal genus selected from the group consisting of *Melanocarpus* and *Myriococcum*.

13. A method of claim 12, wherein the fungal species is *Melanocarpus albomyces, Myriococcum albomyces,* or *Myriococcum* sp. species represented by CBS 687.95.

14. A method of claim 13, wherein the fungus is *Melanocarpus albomyces, Myriococcum albomyces* CBS 685.95, or *Myriococcum* sp. CBS 687.95.

15. A method according to claim 1, wherein the enzyme preparation is liquid.

16. A method according to claim 1, wherein the enzyme preparation is dry.

17. A method according to claim 1, wherein the fabric or garments is denim.

18. A method according to claim 1, wherein the enzyme preparation further comprises a surface active agent.

19. A method for biofinishing comprising adding an enzyme preparation comprising a polypeptide having cellulase activity to textile materials like fabrics or garments or yarn, wherein said polypeptide is selected from the group consisting of:
(i) a polypeptide comprising the amino acid sequence set forth in FIG. 19 and SEQ ID NO: 31,
(ii) a polypeptide having at least 95% identity to the amino acid sequence set forth in FIG. 19 and SEQ ID NO: 31,
(iii) a polypeptide comprising the amino acid sequence encoded by the DNA insert contained in the vector transformed into DSM 11024 or DSM 11012,
(iv) a polypeptide comprising amino acids 22-235 of the amino acid sequence set forth in FIG. 19 and SEQ ID NO: 31; and
(v) a polypeptide having at least 95% identity to amino acids 22-235 of the amino acid sequence set forth in FIG. 19 and SEQ ID NO: 31.

20. A method according to claim 19, wherein said polypeptide comprises the amino acid sequence set forth in FIG. 19 and SEQ ID NO: 31.

21. A method according to claim 19, wherein said polypeptide has at least 95% identity to the amino acid sequence set forth in FIG. 19 and SEQ ID NO: 31.

22. A method according to claim 19, wherein said polypeptide comprises the amino acid sequence encoded by the DNA insert contained in the vector transformed into DSM 11024 or DSM 11012.

23. A method according to claim 19, wherein said polypeptide comprises amino acids 22-235 of the amino acid sequence set forth in FIG. 19 and SEQ ID NO: 31.

24. A method according to claim 19, wherein said polypeptide has at least 95% identity to amino acids 22-235 of the amino acid sequence set forth in FIG. 19 and SEQ ID NO: 31.

25. A method according to claim 19, wherein said enzyme preparation is obtained by a process comprising:
(i) culturing a host cell transformed with the nucleic acid molecule comprising the sequence set forth in FIG. 19 (SEQ ID NO: 30); and
(ii) separating said host cell from the culture medium and obtaining the supernatant having cellulase activity.

26. A method according to claim 19, wherein said enzyme preparation is obtained by a process comprising:
(i) culturing a host cell transformed with the nucleic acid sequence encoding a cellulase having at least 95% identity to the amino acid sequence set forth in FIG. 19 (SEQ ID NO: 31); and
(ii) separating said host cell from the culture medium and obtaining the supernatant having cellulase activity.

27. A method according to claim 19, wherein said enzyme preparation is obtained by a process comprising:
(i) culturing a host cell transformed with the nucleic acid sequence encoding amino acids 22-235 of the amino acid sequence set forth in FIG. 19 (SEQ ID NO: 31); and
(ii) separating said host cell from the culture medium and obtaining the supernatant having cellulase activity.

28. A method according to claim 19, wherein said enzyme preparation is obtained by a process comprising:
(i) culturing a host cell transformed with the nucleic acid sequence encoding a cellulase having at least 95% identity to amino acids 22-235 of the amino acid sequence set forth in FIG. 19 (SEQ ID) NO: 31); and
(ii) separating said host cell from the culture medium and obtaining the supernatant having cellulase activity.

29. A method according to claim 19, wherein said polypeptide is isolated and essentially homogenous.

30. A method according to claim 19, wherein said enzyme preparation comprises at least one cellulase of a fungal species belonging to a fungal genus selected from the group consisting of *Melanocarpus* and *Myriococcum*.

31. A method of claim 30, wherein the fungal species is *Melanocarpus albomyces, Myriococcum albomyces,* or *Myriococcum* sp. species represented by CBS 687.95.

32. A method of claim 31, wherein the fungus is *Melanocarpus albomyces, Myriococcum albomyces* CBS 685.95, or *Myriococcum* sp. CBS 687.95.

33. A method according to claim 19, wherein the enzyme preparation is liquid.

34. A method according to claim 19, wherein the enzyme preparation is dry.

35. A method according to claim 19, wherein the textile materials are manufactured of natural cellulose containing fibers or manmade cellulose containing fibers or are mixtures thereof.

36. A method according to claim 19, wherein the textile materials are blends of synthetic fibers and cellulose containing fibers.

37. A method according to claim 19, wherein the enzyme preparation further comprises a surface active agent.

38. A method for treating wood-derived pulp or fiber, comprising adding an enzyme preparation comprising a polypeptide having cellulase activity to wood-derived mechanical or chemical pulp or secondary fiber, wherein said polypeptide is selected from the group consisting of:
  (i) a polypeptide comprising the amino acid sequence set forth in FIG. 19 and SEQ ID NO: 31,
  (ii) a polypeptide having at least 95% identity to the amino acid sequence set forth in FIG. 19 and SEQ ID NO: 31,
  (iii) a polypeptide comprising the amino acid sequence encoded by the DNA insert contained in the vector transformed into DSM 11024 or DSM 11012,
  (iv) a polypeptide comprising amino acids 22-235 of the amino acid sequence set forth in FIG. 19 and SEQ ID NO: 31; and
  (v) a polypeptide having at least 95% identity to amino acids 22-235 of the amino acid sequence set forth in FIG. 19 and SEQ ID NO: 31.

39. A method according to claim 38, wherein said polypeptide comprises the amino acid sequence set forth in FIG. 19 and SEQ ID NO: 31.

40. A method according to claim 38, wherein said polypeptide has at least 95% identity to the amino acid sequence set forth in FIG. 19 and SEQ ID NO: 31.

41. A method according to claim 38, wherein said polypeptide comprises the amino acid sequence encoded by the DNA insert contained in the vector transformed into DSM 11024 or DSM 11012.

42. A method according to claim 38, wherein said polypeptide comprises amino acids 22-235 of the amino acid sequence set forth in FIG. 19 and SEQ ID NO: 31.

43. A method according to claim 38, wherein said polypeptide has at least 95% identity to amino acids 22-235 of the amino acid sequence set forth in FIG. 19 and SEQ ID NO: 31.

44. A method according to claim 38, wherein said enzyme preparation is obtained by a process comprising:
  (i) culturing a host cell transformed with the nucleic acid molecule comprising the sequence set forth in FIG. 19 (SEQ ID NO: 30); and
  (ii) separating said host cell from the culture medium and obtaining the supernatant having cellulase activity.

45. A method according to claim 38, wherein said enzyme preparation is obtained by a process comprising:
  (i) culturing a host cell transformed with the nucleic acid sequence encoding a cellulase having at least 95% identity to the amino acid sequence set forth in FIG. 19 (SEQ ID NO: 31); and
  (ii) separating said host cell from the culture medium and obtaining the supernatant having cellulase activity.

46. A method according to claim 38, wherein said enzyme preparation is obtained by a process comprising:
  (i) culturing a host cell transformed with the nucleic acid sequence encoding amino acids 22-235 of the amino acid sequence set forth in FIG. 19 (SEQ ID NO: 31); and
  (ii) separating said host cell from the culture medium and obtaining the supernatant having cellulase activity.

47. A method according to claim 38, wherein said enzyme preparation is obtained by a process comprising:
  (i) culturing a host cell transformed with the nucleic acid sequence encoding a cellulase having at least 95% identity to amino acids 22-235 of the amino acid sequence set forth in FIG. 19 (SEQ ID NO: 31); and
  (ii) separating said host cell from the culture medium and obtaining the supernatant having cellulase activity.

48. A method according to claim 38, wherein said polypeptide is isolated and essentially homogenous.

49. A method according to claim 38, wherein said enzyme preparation comprises at least one cellulase of a fungal species belonging to a fungal genus selected from the group consisting of *Melanocarpus* and *Myriococcum*.

50. A method of claim 49, wherein the fungal species is *Melanocarpus albomyces*, *Myriococcum albomyces*, or *Myriococcum* sp. species represented by CBS 687.95.

51. A method of claim 50, wherein the fungus is *Melanocarpus albomyces*, *Myriococcum albomyces* CBS 685.95, or *Myriococcum* sp. CBS 687.95.

52. A method according to claim 38, wherein the enzyme preparation is liquid.

53. A method according to claim 38, wherein the enzyme preparation is dry.

54. A method according to claim 38, wherein the enzyme preparation further comprises a surface active agent.

55. A method for improving the quality of animal feed, comprising treating plant material with an enzyme preparation comprising a polypeptide having cellulase activity, wherein said polypeptide is selected from the group consisting of:
  (i) a polypeptide comprising the amino acid sequence set forth in FIG. 19 and SEQ ID NO: 31,
  (ii) a polypeptide having at least 95% identity to the amino acid sequence set forth in FIG. 19 and SEQ ID NO: 31,
  (iii) a polypeptide comprising the amino acid sequence encoded by the DNA insert contained in the vector transformed into DSM 11024 or DSM 11012,
  (iv) a polypeptide comprising amino acids 22-235 of the amino acid sequence set forth in FIG. 19 and SEQ ID NO: 31; and
  (v) a polypeptide having at least 95% identity to amino acids 22-235 of the amino acid sequence set forth in FIG. 19 and SEQ ID NO: 31.

56. A method according to claim 55, wherein said polypeptide comprises the amino acid sequence set forth in FIG. 19 and SEQ ID NO: 31.

57. A method according to claim 55, wherein said polypeptide has at least 95% identity to the amino acid sequence set forth in FIG. 19 and SEQ ID NO: 31.

58. A method according to claim 55, wherein said polypeptide comprises the amino acid sequence encoded by the DNA insert contained in the vector transformed into DSM 11024 or DSM 11012.

59. A method according to claim 55, wherein said polypeptide comprises amino acids 22-235 of the amino acid sequence set forth in FIG. 19 and SEQ ID NO: 31.

60. A method according to claim 55, wherein said polypeptide has at least 95% identity to amino acids 22-235 of the amino acid sequence set forth in FIG. 19 and SEQ ID NO: 31.

61. A method according to claim 55, wherein said enzyme preparation is obtained by a process comprising:
  (i) culturing a host cell transformed with the nucleic acid molecule comprising the sequence set forth in FIG. 19 (SEQ ID NO: 30); and
  (ii) separating said host cell from the culture medium and obtaining the supernatant having cellulase activity.

62. A method according to claim 55, wherein said enzyme preparation is obtained by a process comprising:
   (i) culturing a host cell transformed with the nucleic acid sequence encoding a cellulase having at least 95% identity to the amino acid sequence set forth in FIG. 19 (SEQ ID NO: 31); and
   (ii) separating said host cell from the culture medium and obtaining the supernatant having cellulase activity.

63. A method according to claim 55, wherein said enzyme preparation is obtained by a process comprising:
   (i) culturing a host cell transformed with the nucleic acid sequence encoding amino acids 22-235 of the amino acid sequence set forth in FIG. 19 (SEQ ID NO: 31); and
   (ii) separating said host cell from the culture medium and obtaining the supernatant having cellulase activity.

64. A method according to claim 55, wherein said enzyme preparation is obtained by a process comprising:
   (i) culturing a host cell transformed with the nucleic acid sequence encoding a cellulase having at least 95% identity to amino acids 22-235 of the amino acid sequence set forth in FIG. 19 (SEQ ID NO: 31); and
   (ii) separating said host cell from the culture medium and obtaining the supernatant having cellulase activity.

65. A method according to claim 55, wherein said polypeptide is isolated and essentially homogenous.

66. A method according to claim 55, wherein said enzyme preparation comprises at least one cellulase of a fungal species belonging to a fungal genus selected from the group consisting of *Melanocarpus* and *Myriococcum*.

67. A method of claim 66, wherein the fungal species is *Melanocarpus albomyces, Myriococcum albomyces* CBS 685.95, or *Myriococcum* sp. represented by CBS 687.95.

68. A method of claim 67, wherein the fungus is *Melanocarpus albomyces, Myriococcum albomyces* CBS 685.95, or *Myriococcum* sp. CBS 687.95.

69. A method according to claim 55, wherein the enzyme preparation is liquid.

70. A method according to claim 55, wherein the enzyme preparation is dry.

71. A method according to claim 55, wherein the enzyme preparation further comprises a surface active agent.

72. A method according to claims 1, 19, 38, or 55, wherein said enzyme preparation further comprises at least one other cellulase of a fungal species belonging to a fungal genus selected from the group consisting of *Melanocarpus* and *Myriococcum*.

73. A method according to claims 1, 19, 38, or 55, wherein said enzyme preparation is a partially or completely purified *Melanocarpus* cellulase fraction.

74. A method according to claims 1, 19, 38, or 55, wherein said enzyme preparation is a culture supernatant comprising the cellulases derived from *Melanocarpus albomyces*.

* * * * *

SEQUENCE LISTING

<160> NUMBER OF SEQ ID NOS: 45

<210> SEQ ID NO 1
<211> LENGTH: 30
<212> TYPE: PRT
<213> ORGANISM: Melanocarpus albomyces

<400> SEQUENCE: 1

Ala Asn Gly Gln Ser Thr Arg Tyr Trp Asp Cys Cys Lys Pro Ser Cys
1               5                   10                  15

Gly Trp Arg Gly Lys Gly Pro Val Asn Gln Pro Val Tyr Ser
            20                  25                  30

<210> SEQ ID NO 2
<211> LENGTH: 7
<212> TYPE: PRT
<213> ORGANISM: Melanocarpus albomyces

<400> SEQUENCE: 2

Tyr Gly Gly Ile Ser Ser Arg
1               5

<210> SEQ ID NO 3
<211> LENGTH: 4
<212> TYPE: PRT
<213> ORGANISM: Melanocarpus albomyces

<400> SEQUENCE: 3

Cys Gly Trp Arg
1

<210> SEQ ID NO 4
<211> LENGTH: 6
<212> TYPE: PRT
<213> ORGANISM: Melanocarpus albomyces

<400> SEQUENCE: 4

Pro Ser Cys Gly Trp Arg
1               5

<210> SEQ ID NO 5
<211> LENGTH: 6
<212> TYPE: PRT
<213> ORGANISM: Melanocarpus albomyces

<400> SEQUENCE: 5

Tyr Trp Asp Cys Cys Lys
1               5

<210> SEQ ID NO 6
<211> LENGTH: 17
<212> TYPE: PRT
<213> ORGANISM: Melanocarpus albomyces

<400> SEQUENCE: 6

Gln Glu Cys Asp Ser Phe Pro Glu Pro Leu Lys Pro Gly Cys Gln Trp
1               5                   10                  15

Arg

<210> SEQ ID NO 7
<211> LENGTH: 8
<212> TYPE: PRT

-continued

<213> ORGANISM: Melanocarpus albomyces

<400> SEQUENCE: 7

Arg His Asp Asp Gly Gly Phe Ala
1               5

<210> SEQ ID NO 8
<211> LENGTH: 7
<212> TYPE: PRT
<213> ORGANISM: Melanocarpus albomyces

<400> SEQUENCE: 8

Tyr Trp Asp Cys Cys Lys Pro
1               5

<210> SEQ ID NO 9
<211> LENGTH: 18
<212> TYPE: PRT
<213> ORGANISM: Melanocarpus albomyces

<400> SEQUENCE: 9

Gly Lys Gly Pro Val Asn Gln Pro Val Tyr Ser Cys Asp Ala Asn Phe
1               5                   10                  15

Gln Arg

<210> SEQ ID NO 10
<211> LENGTH: 10
<212> TYPE: PRT
<213> ORGANISM: Melanocarpus albomyces

<400> SEQUENCE: 10

Val Gln Cys Pro Glu Glu Leu Val Ala Arg
1               5                   10

<210> SEQ ID NO 11
<211> LENGTH: 15
<212> TYPE: PRT
<213> ORGANISM: Melanocarpus albomyces

<400> SEQUENCE: 11

Asp Trp Phe Gln Asn Ala Asp Asn Pro Ser Phe Thr Phe Glu Arg
1               5                   10                  15

<210> SEQ ID NO 12
<211> LENGTH: 30
<212> TYPE: PRT
<213> ORGANISM: Melanocarpus albomyces

<400> SEQUENCE: 12

Thr Met Val Val Gln Ser Thr Ser Thr Gly Gly Asp Leu Gly Ser Asn
1               5                   10                  15

His Phe Asp Leu Asn Ile Pro Gly Gly Gly Val Gly Leu Phe
            20                  25                  30

<210> SEQ ID NO 13
<211> LENGTH: 10
<212> TYPE: PRT
<213> ORGANISM: Melanocarpus albomyces

<400> SEQUENCE: 13

Val Tyr Leu Leu Asp Glu Thr Glu His Arg
1               5                   10

```
<210> SEQ ID NO 14
<211> LENGTH: 12
<212> TYPE: PRT
<213> ORGANISM: Melanocarpus albomyces
<220> FEATURE:
<221> NAME/KEY: misc_feature
<222> LOCATION: (1)..(2)
<223> OTHER INFORMATION: Xaa can be any naturally occurring amino acid

<400> SEQUENCE: 14

Xaa Xaa Leu Asn Pro Gly Gly Ala Tyr Tyr Gly Thr
1               5                   10

<210> SEQ ID NO 15
<211> LENGTH: 17
<212> TYPE: PRT
<213> ORGANISM: Melanocarpus albomyces

<400> SEQUENCE: 15

Met Ser Glu Gly Ala Glu Cys Glu Tyr Asp Gly Val Cys Asp Lys Asp
1               5                   10                  15

Gly

<210> SEQ ID NO 16
<211> LENGTH: 14
<212> TYPE: PRT
<213> ORGANISM: Melanocarpus albomyces
<220> FEATURE:
<221> NAME/KEY: misc_feature
<222> LOCATION: (6)..(6)
<223> OTHER INFORMATION: Xaa can be any naturally occurring amino acid

<400> SEQUENCE: 16

Asn Pro Tyr Arg Val Xaa Ile Thr Asp Tyr Tyr Gly Asn Ser
1               5                   10

<210> SEQ ID NO 17
<211> LENGTH: 24
<212> TYPE: PRT
<213> ORGANISM: Melanocarpus albomyces
<220> FEATURE:
<221> NAME/KEY: misc_feature
<222> LOCATION: (21)..(21)
<223> OTHER INFORMATION: Xaa can be any naturally occurring amino acid

<400> SEQUENCE: 17

Asp Pro Thr Gly Ala Arg Ser Glu Leu Asn Pro Gly Gly Ala Tyr Tyr
1               5                   10                  15

Gly Thr Gly Tyr Xaa Asp Ala Gln
            20

<210> SEQ ID NO 18
<211> LENGTH: 13
<212> TYPE: PRT
<213> ORGANISM: Melanocarpus albomyces
<220> FEATURE:
<221> NAME/KEY: misc_feature
<222> LOCATION: (1)..(2)
<223> OTHER INFORMATION: Xaa can be any naturally occurring amino acid

<400> SEQUENCE: 18

Xaa Xaa Val Pro Asp Tyr His Gln His Gly Val Asp Ala
1               5                   10

<210> SEQ ID NO 19
<211> LENGTH: 12
<212> TYPE: PRT
```

<213> ORGANISM: Melanocarpus albomyces
<220> FEATURE:
<221> NAME/KEY: misc_feature
<222> LOCATION: (6)..(6)
<223> OTHER INFORMATION: Xaa can be any naturally occurring amino acid

<400> SEQUENCE: 19

Asn Glu Met Asp Ile Xaa Glu Ala Asn Ser Arg Ala
1               5                   10

<210> SEQ ID NO 20
<211> LENGTH: 25
<212> TYPE: PRT
<213> ORGANISM: Melanocarpus albomyces
<220> FEATURE:
<221> NAME/KEY: misc_feature
<222> LOCATION: (3)..(3)
<223> OTHER INFORMATION: Xaa can be any naturally occurring amino acid

<400> SEQUENCE: 20

Leu Pro Xaa Gly Met Asn Ser Ala Leu Tyr Leu Ser Glu Met Asp Pro
1               5                   10                  15
Thr Gly Ala Arg Ser Glu Leu Asn Pro
            20                  25

<210> SEQ ID NO 21
<211> LENGTH: 21
<212> TYPE: PRT
<213> ORGANISM: Melanocarpus albomyces
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 21

Val Glu Pro Ser Pro Glu Val Thr Tyr Ser Asn Leu Arg Xaa Gly Glu
1               5                   10                  15
Ile Xaa Gly Xaa Phe
            20

<210> SEQ ID NO 22
<211> LENGTH: 19
<212> TYPE: PRT
<213> ORGANISM: Melanocarpus albomyces

<400> SEQUENCE: 22

Asp Gly Cys Gly Trp Asn Pro Tyr Arg Val Val Ile Thr Thr Asp Tyr
1               5                   10                  15
Tyr Asn Asn

<210> SEQ ID NO 23
<211> LENGTH: 10
<212> TYPE: PRT
<213> ORGANISM: Melanocarpus albomyces
<220> FEATURE:
<221> NAME/KEY: misc_feature
<222> LOCATION: (6)..(6)
<223> OTHER INFORMATION: Xaa can be any naturally occurring amino acid

<400> SEQUENCE: 23

```
Leu Pro Cys Gly Met Xaa Ser Ala Leu Tyr
1               5                  10

<210> SEQ ID NO 24
<211> LENGTH: 22
<212> TYPE: PRT
<213> ORGANISM: Melanocarpus albomyces
<220> FEATURE:
<221> NAME/KEY: misc_feature
<222> LOCATION: (20)..(21)
<223> OTHER INFORMATION: Xaa can be any naturally occurring amino acid

<400> SEQUENCE: 24

Ala Asp Gly Cys Gln Pro Arg Thr Asn Tyr Ile Val Leu Asp Asp Leu
1               5                  10                  15

Leu His Pro Xaa Xaa Gln
            20

<210> SEQ ID NO 25
<211> LENGTH: 9
<212> TYPE: PRT
<213> ORGANISM: Melanocarpus albomyces

<400> SEQUENCE: 25

Val Gly Asn Pro Asp Phe Tyr Gly Lys
1               5

<210> SEQ ID NO 26
<211> LENGTH: 8
<212> TYPE: PRT
<213> ORGANISM: Melanocarpus albomyces

<400> SEQUENCE: 26

Phe Gly Pro Ile Gly Ser Thr Tyr
1               5

<210> SEQ ID NO 27
<211> LENGTH: 12
<212> TYPE: PRT
<213> ORGANISM: Melanocarpus albomyces

<400> SEQUENCE: 27

Leu Ser Gln Tyr Phe Ile Gln Asp Gly Glu Arg Lys
1               5                  10

<210> SEQ ID NO 28
<211> LENGTH: 11
<212> TYPE: PRT
<213> ORGANISM: Melanocarpus albomyces

<400> SEQUENCE: 28

Phe Thr Val Val Ser Arg Phe Glu Glu Asn Lys
1               5                  10

<210> SEQ ID NO 29
<211> LENGTH: 19
<212> TYPE: PRT
<213> ORGANISM: Melanocarpus albomyces

<400> SEQUENCE: 29

His Glu Tyr Gly Thr Asn Val Gly Ser Arg Phe Tyr Leu Met Asn Gly
1               5                  10                  15

Pro Asp Lys
```

```
<210> SEQ ID NO 30
<211> LENGTH: 936
<212> TYPE: DNA
<213> ORGANISM: Melanocarpus albomyces

<400> SEQUENCE: 30
tcgcccctaa ccgagaacca aagactccaa gaatgcgctc tactcccgtt ctccgcgccc      60
tcctggccgc agcattgccc ctcggggccc tcgccgccaa cggtcagtcc acgaggtaac     120
tgatcacccg cctcattacg cgtgccgacc ggaccgcgtt cagggctcac tgctcaccgc     180
atccagatac tgggactgct gcaagccgtc gtgcggctgg cgcggaaagg cccccgtgaa     240
ccagcccgtc tactcgtgcg acgccaactt ccagcgcatc cacgacttcg atgccgtctc     300
gggctgcgag gcggccccg ccttctcgtg cgccgaccac agcccctggg ccattaatga     360
caacctctcg tacggcttcg cggcgactgc actcagcggc cagaccgagg agtcgtggtg     420
ctgtgcctgc tacgcgtgag tgtgcttggg cccaacgtcg gtgattccgg agttcagacc     480
actgacccag cgaccgcctc gccagtctga cctttacatc gggtcccgtg ccggcaaga     540
ccatggtcgt ccagtcgacc agcacgggcg gcgacctcgg cagcaaccac ttcgacctca     600
acatccccgg cggcggcgtc ggcctcttcg acggctgcac tccccagttc ggcggcctcc     660
cgggcgcacg gtacggcggc atctcgtcgc gccaggagtg cgactcgttc cccgagccgc     720
tcaagcccgg ctgccagtgg cgcttcgact ggttccagaa cgccgacaac ccgtccttta     780
ccttcgagcg gtccagtgc cccgaggagc tggtcgctcg gaccggctgc aggcgccacg     840
acgacggcgg cttcgccgtc ttcaaggccc ccagcgcctg atccgttttt gggcagtgtc     900
cgtgtgacgg cagctacgtg gaacgacctg gagctc                              936

<210> SEQ ID NO 31
<211> LENGTH: 235
<212> TYPE: PRT
<213> ORGANISM: Melanocarpus albomyces

<400> SEQUENCE: 31

Met Arg Ser Thr Pro Val Leu Arg Ala Leu Leu Ala Ala Ala Leu Pro
1               5                  10                  15

Leu Gly Ala Leu Ala Ala Asn Gly Gln Ser Thr Arg Tyr Trp Asp Cys
            20                  25                  30

Cys Lys Pro Ser Cys Gly Trp Arg Gly Lys Gly Pro Val Asn Gln Pro
        35                  40                  45

Val Tyr Ser Cys Asp Ala Asn Phe Gln Arg Ile His Asp Phe Asp Ala
    50                  55                  60

Val Ser Gly Cys Glu Gly Gly Pro Ala Phe Ser Cys Ala Asp His Ser
65                  70                  75                  80

Pro Trp Ala Ile Asn Asp Asn Leu Ser Tyr Gly Phe Ala Ala Thr Ala
                85                  90                  95

Leu Ser Gly Gln Thr Glu Glu Ser Trp Cys Cys Ala Cys Tyr Ala Leu
            100                 105                 110

Thr Phe Thr Ser Gly Pro Val Ala Gly Lys Thr Met Val Val Gln Ser
        115                 120                 125

Thr Ser Thr Gly Gly Asp Leu Gly Ser Asn His Phe Asp Leu Asn Ile
    130                 135                 140

Pro Gly Gly Gly Val Gly Leu Phe Asp Gly Cys Thr Pro Gln Phe Gly
145                 150                 155                 160

Gly Leu Pro Gly Ala Arg Tyr Gly Gly Ile Ser Ser Arg Gln Glu Cys
```

|     |     | 165 |     |     | 170 |     |     | 175 |     |     |     |
| --- | --- | --- | --- | --- | --- | --- | --- | --- | --- | --- | --- |
| Asp | Ser | Phe | Pro | Glu | Pro | Leu | Lys | Pro | Gly | Cys | Gln | Trp | Arg | Phe | Asp |
|     |     |     | 180 |     |     |     |     | 185 |     |     |     |     | 190 |     |     |

Trp Phe Gln Asn Ala Asp Asn Pro Ser Phe Thr Phe Glu Arg Val Gln
        195                 200                 205

Cys Pro Glu Glu Leu Val Ala Arg Thr Gly Cys Arg Arg His Asp Asp
    210                 215                 220

Gly Gly Phe Ala Val Phe Lys Ala Pro Ser Ala
225                 230                 235

<210> SEQ ID NO 32
<211> LENGTH: 1894
<212> TYPE: DNA
<213> ORGANISM: Melanocarpus albomyces

<400> SEQUENCE: 32

| | | | | |
|---|---|---|---|---|
| gaattcgggg gttgccaggg agtcgtacag gggtgggtgg aggggatgg gggatggaag | 60 |
| ggggatggag aagaaagcat atatgggacg tttgtgctcg ccggctcccc tctgccacgt | 120 |
| tcccttgcct ccttgcctgg gttgttgttg gtcttccctt caccatccga caaaccaacc | 180 |
| tgctgcgggt gaactcgcag agcgccttcg acgacgaca dacagacgca ccatgactcg | 240 |
| caacatcgcc ctgctcggcg ccgcgtcggc gctcctgggc ctcgcccacg ccagaagcc | 300 |
| gggcgagacg cccgaggtgc acccgcagct gacgacgttc cggtgcacca aggcggacgg | 360 |
| gtgccagccg cggaccaact acattgtgct ggactcgctg tcgcacccgg tgcaccaggt | 420 |
| ggacaacgac tacaactgcg cgactgggg gcagaagccc aacgcgacgg cgtgcccgga | 480 |
| cgtcgagtcg tgcgcgcgca actgcatcat ggagggcgtg cccgactaca gccagcacgg | 540 |
| cgtcacgacg agcgacacgt cgctgcgcct gcagcagctc gtcgacggcc gcctcgtcac | 600 |
| gccgcgcgtc tacctgctcg acgagaccga gcaccgctac gagatgatgc acctgaccgg | 660 |
| ccaggagttc accttttgagg tcgacgccac caagctgccc tgcggcatga acagcgccct | 720 |
| ctacctgtcc gagatggacc cgaccggcgc ccggagcgag ctcaaccccg gcggtgccta | 780 |
| ctacggcacc ggctactgcg acgcccagtg cttcgtgacg ccattcatca acggcattgt | 840 |
| gagtgttccc cttttggcccc cccctgaaa atagatgtac ctgggtgcta accccgggt | 900 |
| gtcgcaccaa acagggcaa catcgagggc aagggctcgt gctgcaacga gatggacatc | 960 |
| tgggaggcca actcgcgggc gacgcacgtg gcgccgcaca cgtgcaacca gacgggtctg | 1020 |
| tacatgtgcg agggcgccga gtgcgagtac gacggcgtgt gcgacaagga cgggtgcggg | 1080 |
| tggaacccgt accgggtcaa catcaccgac tactacggca actcggacgc gttccgcgtc | 1140 |
| gacacgcggc ggcccttcac cgtggtgacg cagttcccgg ccgacgccga gggccggctc | 1200 |
| gagagcatcc accggctgta cgtgcaggac ggcaaggtga tcgagtcgta cgtcgtcgac | 1260 |
| gcgccgggcc tgcccggac cgactcgctc aacgacgagt tctgcgccgc cacgggcgcc | 1320 |
| gcgcgctacc tcgacctcgg cggcaccgcg gcatgggcg acgccatgac gcgcggcatg | 1380 |
| gtgctggcca tgagcatctg gtgggacgag tccggcttca tgaactggct cgacagcggc | 1440 |
| gaggccggcc cctgcctgcc cgacgagggc gaccccaaga acattgtcaa ggtcgagccc | 1500 |
| agccccgagg tcacctacag caacctgcgc tgggcgaga tcgggtcgac ctttgaggcc | 1560 |
| gagtccgacg acgacggcga cggcgacgac tgctagataa ctaactagtg gcggaaagg | 1620 |
| gcgggggatg cgtaacttac atacagcccg gagttgtttt gagtgtagag tattgagctt | 1680 |
| tcgatgtgtt agttgagtgg aatggaaaat tcgcgtcttt gccccggtgg ttgcgataaa | 1740 |

-continued

```
caatagtcgg ctggtgcatt tgtgacactt caattgcgct gttggcttgg tgacagacac    1800
ggcagcgtcg atgacccgac acccagaata attcgcatgg ttgattatgt tattgtgctt    1860
taaatcggag gctgatgctc atctcttcga attc                                1894
```

<210> SEQ ID NO 33
<211> LENGTH: 428
<212> TYPE: PRT
<213> ORGANISM: Melanocarpus albomyces

<400> SEQUENCE: 33

```
Met Thr Arg Asn Ile Ala Leu Leu Gly Ala Ala Ser Ala Leu Leu Gly
1               5                   10                  15

Leu Ala His Gly Gln Lys Pro Gly Glu Thr Pro Glu Val His Pro Gln
            20                  25                  30

Leu Thr Thr Phe Arg Cys Thr Lys Ala Asp Gly Cys Gln Pro Arg Thr
        35                  40                  45

Asn Tyr Ile Val Leu Asp Ser Leu Ser His Pro Val His Gln Val Asp
    50                  55                  60

Asn Asp Tyr Asn Cys Gly Asp Trp Gly Gln Lys Pro Asn Ala Thr Ala
65                  70                  75                  80

Cys Pro Asp Val Glu Ser Cys Ala Arg Asn Cys Ile Met Glu Gly Val
                85                  90                  95

Pro Asp Tyr Ser Gln His Gly Val Thr Thr Ser Asp Thr Ser Leu Arg
            100                 105                 110

Leu Gln Gln Leu Val Asp Gly Arg Leu Val Thr Pro Arg Val Tyr Leu
        115                 120                 125

Leu Asp Glu Thr Glu His Arg Tyr Glu Met Met His Leu Thr Gly Gln
    130                 135                 140

Glu Phe Thr Phe Glu Val Asp Ala Thr Lys Leu Pro Cys Gly Met Asn
145                 150                 155                 160

Ser Ala Leu Tyr Leu Ser Glu Met Asp Pro Thr Gly Ala Arg Ser Glu
                165                 170                 175

Leu Asn Pro Gly Gly Ala Tyr Tyr Gly Thr Gly Tyr Cys Asp Ala Gln
            180                 185                 190

Cys Phe Val Thr Pro Phe Ile Asn Gly Ile Gly Asn Ile Glu Gly Lys
        195                 200                 205

Gly Ser Cys Cys Asn Glu Met Asp Ile Trp Glu Ala Asn Ser Arg Ala
    210                 215                 220

Thr His Val Ala Pro His Thr Cys Asn Gln Thr Gly Leu Tyr Met Cys
225                 230                 235                 240

Glu Gly Ala Glu Cys Glu Tyr Asp Gly Val Cys Asp Lys Asp Gly Cys
                245                 250                 255

Gly Trp Asn Pro Tyr Arg Val Asn Ile Thr Asp Tyr Tyr Gly Asn Ser
            260                 265                 270

Asp Ala Phe Arg Val Asp Thr Arg Arg Pro Phe Thr Val Val Thr Gln
        275                 280                 285

Phe Pro Ala Asp Ala Glu Gly Arg Leu Glu Ser Ile His Arg Leu Tyr
    290                 295                 300

Val Gln Asp Gly Lys Val Ile Glu Ser Tyr Val Val Asp Ala Pro Gly
305                 310                 315                 320

Leu Pro Arg Thr Asp Ser Leu Asn Asp Glu Phe Cys Ala Ala Thr Gly
                325                 330                 335

Ala Ala Arg Tyr Leu Asp Leu Gly Gly Thr Ala Gly Met Gly Asp Ala
```

```
                340             345             350
Met Thr Arg Gly Met Val Leu Ala Met Ser Ile Trp Trp Asp Glu Ser
            355                 360                 365

Gly Phe Met Asn Trp Leu Asp Ser Gly Glu Ala Gly Pro Cys Leu Pro
        370                 375                 380

Asp Glu Gly Asp Pro Lys Asn Ile Val Lys Val Glu Pro Ser Pro Glu
385                 390                 395                 400

Val Thr Tyr Ser Asn Leu Arg Trp Gly Glu Ile Gly Ser Thr Phe Glu
                405                 410                 415

Ala Glu Ser Asp Asp Asp Gly Asp Gly Asp Asp Cys
            420                 425
```

<210> SEQ ID NO 34
<211> LENGTH: 2000
<212> TYPE: DNA
<213> ORGANISM: Melanocarpus albomyces

<400> SEQUENCE: 34

```
cccggtctgg agacggggag cgcgccagcg acgcaggata agaaggcgac gaccgcgcct      60
ccgagccagg cccaggacag caggagaact cgccacgcgc aagcagcacg cccgatcgac     120
agtgtcccgc tctgcccaca gcactctgca accatgatga tgaagcagta cctccagtac     180
ctcgcggccg cgctgccgct cgtcggcctc gccgccggcc agcgcgctgg taacgagacg     240
cccgagaacc accccccgct cacctggcag aggtgcacgg ccccgggcaa ctgccagacc     300
gtgaacgccg aggtcgtcat tgacgccaac tggcgctggc tgcacgacga caacatgcag     360
aactgctacg acggcaacca gtggaccaac gcctgcagca ccgccaccga ctgcgctgag     420
aagtgcatga tcgagggtgc cggcgactac ctgggcacct acggcgcctc gaccagcggc     480
gacgccctga cgctcaagtt cgtcaccaag cacgagtacg gcaccaacgt cggctcgcgc     540
ttctacctca tgaacggccc ggacaagtac cagatgttca acctcatggg caacgagctt     600
gcctttgacg tcgacctctc gaccgtcgag tgcggcatca cagcgccct gtacttcgtc     660
gccatggagg aggacggcgg catggccagc tacccgagca accaggccgg cgcccggtac     720
ggcactgggg tgagttgagc tccgctttgt ttcgagtcgc aacgaggcac tttctgggcg     780
ccggctaact ctctcgattc ctccgacagt actgcgatgc caatgcgct cgtgatctca     840
agttcgttgg cggcaaggcc aacattgagg ctggaagtc gtccaccagc daccccaacg     900
ctggcgtcgg cccgtacggc agctgctgcg ctgagatcga cgtctggtga gtgcgagacc     960
gtccacccag gttcggatgc ggggtggaaa tttcgcggct aacggagcac cccccaggga    1020
gtcgaatgcc tatgccttcg ctttcacgcc gcacgcgtgc acgaccaacg agtaccacgt    1080
ctgcgagacc accaactgcg gtggcaccta ctcggaggac cgcttcgccg gcaagtgcga    1140
cgccaacggc tgcgactaca cccctaccg catgggcaac cccgacttct acggcaaggg    1200
caagacgctc gacaccagcc gcaagttcac gtgcgtgacc ccttgtggcg caacctttct    1260
ctgcctgcct ggacacactg aaactgcaca gtcgttttcg gctgcagcgt cgtctcccgc    1320
ttcgaggaga acaagctctc ccagtacttc atccaggacg gccgcaagat cgagatcccg    1380
ccgccgacgt gggagggcat gcccaacagc agcgagatca cccccgagct ctgctccacc    1440
atgttcgatg tgttcaacga ccgcaaccgc ttcgaggagg tcggcggctt cgagcagctg    1500
aacaacgccc tccgggttcc catggtcctg tcatgtcca tctgggacga cgtaagtacc    1560
cgccgaccte cctagccaca caagccgcat ccggcgaggc acgccatcgc tgctgctaac    1620
```

-continued

```
acgagaccgt tcgtagcact acgccaacat gctctggctc gactccatct acccgcccga    1680
gaaggagggc cagcccggcg ccgcccgtgg cgactgcccc acggactcgg gtgtccccgc    1740
cgaggtcgag gctcagttcc ccgacgcgta agacttgccc ccgaccccaa gcttccactt    1800
ctggatgccg aatgctaaca cgcgaaacag ccaggtcgtc tggtccaaca tccgcttcgg    1860
ccccatcggc tcgacctacg acttctaagc cggtccatgc actcgcagcc ctgggcccgt    1920
cacgcccgcc acctcccctc gcggaaactc tccgtgcgtc gcgggctcca aagcattttg    1980
gcctcaagtt ttttttcgttc                                                2000
```

<210> SEQ ID NO 35
<211> LENGTH: 452
<212> TYPE: PRT
<213> ORGANISM: Melanocarpus albomyces

<400> SEQUENCE: 35

```
Met Met Met Lys Gln Tyr Leu Gln Tyr Leu Ala Ala Ala Leu Pro Leu
1               5                   10                  15

Val Gly Leu Ala Ala Gly Gln Arg Ala Gly Asn Glu Thr Pro Glu Asn
            20                  25                  30

His Pro Pro Leu Thr Trp Gln Arg Cys Thr Ala Pro Gly Asn Cys Gln
        35                  40                  45

Thr Val Asn Ala Glu Val Val Ile Asp Ala Asn Trp Arg Trp Leu His
    50                  55                  60

Asp Asp Asn Met Gln Asn Cys Tyr Asp Gly Asn Gln Trp Thr Asn Ala
65                  70                  75                  80

Cys Ser Thr Ala Thr Asp Cys Ala Glu Lys Cys Met Ile Glu Gly Ala
                85                  90                  95

Gly Asp Tyr Leu Gly Thr Tyr Gly Ala Ser Thr Ser Gly Asp Ala Leu
            100                 105                 110

Thr Leu Lys Phe Val Thr Lys His Glu Tyr Gly Thr Asn Val Gly Ser
        115                 120                 125

Arg Phe Tyr Leu Met Asn Gly Pro Asp Lys Tyr Gln Met Phe Asn Leu
    130                 135                 140

Met Gly Asn Glu Leu Ala Phe Asp Val Asp Leu Ser Thr Val Glu Cys
145                 150                 155                 160

Gly Ile Asn Ser Ala Leu Tyr Phe Val Ala Met Glu Glu Asp Gly Gly
                165                 170                 175

Met Ala Ser Tyr Pro Ser Asn Gln Ala Gly Ala Arg Tyr Gly Thr Gly
            180                 185                 190

Tyr Cys Asp Ala Gln Cys Ala Arg Asp Leu Lys Phe Val Gly Gly Lys
        195                 200                 205

Ala Asn Ile Glu Gly Trp Lys Ser Ser Thr Ser Asp Pro Asn Ala Gly
    210                 215                 220

Val Gly Pro Tyr Gly Ser Cys Cys Ala Glu Ile Asp Val Trp Glu Ser
225                 230                 235                 240

Asn Ala Tyr Ala Phe Ala Phe Thr Pro His Ala Cys Thr Thr Asn Glu
                245                 250                 255

Tyr His Val Cys Glu Thr Thr Asn Cys Gly Gly Thr Tyr Ser Glu Asp
            260                 265                 270

Arg Phe Ala Gly Lys Cys Asp Ala Asn Gly Cys Asp Tyr Asn Pro Tyr
        275                 280                 285

Arg Met Gly Asn Pro Asp Phe Tyr Gly Lys Gly Lys Thr Leu Asp Thr
        290                 295                 300
```

```
Ser Arg Lys Phe Thr Val Val Ser Arg Phe Glu Glu Asn Lys Leu Ser
305                 310                 315                 320

Gln Tyr Phe Ile Gln Asp Gly Arg Lys Ile Glu Ile Pro Pro Thr
            325                 330                 335

Trp Glu Gly Met Pro Asn Ser Ser Glu Ile Thr Pro Glu Leu Cys Ser
            340                 345                 350

Thr Met Phe Asp Val Phe Asn Asp Arg Asn Arg Phe Glu Glu Val Gly
                355                 360                 365

Gly Phe Glu Gln Leu Asn Asn Ala Leu Arg Val Pro Met Val Leu Val
        370                 375                 380

Met Ser Ile Trp Asp Asp His Tyr Ala Asn Met Leu Trp Leu Asp Ser
385                 390                 395                 400

Ile Tyr Pro Pro Glu Lys Glu Gly Gln Pro Gly Ala Ala Arg Gly Asp
                405                 410                 415

Cys Pro Thr Asp Ser Gly Val Pro Ala Glu Val Glu Ala Gln Phe Pro
                420                 425                 430

Asp Ala Gln Val Val Trp Ser Asn Ile Arg Phe Gly Pro Ile Gly Ser
            435                 440                 445

Thr Tyr Asp Phe
    450

<210> SEQ ID NO 36
<211> LENGTH: 887
<212> TYPE: DNA
<213> ORGANISM: Melanocarpus albomyces

<400> SEQUENCE: 36
ccatggacgc gaactgcgac gtcttctgcc ccgagctgaa gacccagagc atccagaccg      60
gcaaccagtg cacccaggag atgaaggtct acgagaacat tgacggctgg ctcgacagcc     120
tgcccggcaa cgtccccatc accggtccgc agcccggctc tggtaagtca agagatgat     180 gcctacctac cttcccacct tcccacccag ccgcaaatac ctttctccct ccccgtgccc     240
cgtattcttt caacgccccg agactgacag acccgctcgt cccaggcggc aaccccggca     300
acggcggcgg cagcaacccg ggcaacggcg gcggcggcgg ctgcaccgtc cagaagtggg     360
gccagtgcgg cggcatcggc tactcgggct gcaccacctg caaggccggc tcgacctgcc     420
cggcccagaa cgagtactac tcgcagtgcc tgtaaagcgg ccgtgggcta ggtggccgag     480
cgggggggtt tcttcattgg ttgagcaaat agaacaggat ttccggctcg ttggcagcgg     540
cgcgccgcgg ggatggtgtt gtacaattca agacctcagt accgagggac ctggaaagga     600
gtcagtctgc ttgtacggag gctggctgcc ccgtggcggc gctggcaagg tagatagccc     660
ttcattgctg taactagtat gctatatacc tctgcacatt tgcagcccca tggtgtgaac     720
aacaagtgac aaggcttcca gttccagcct cgcgcaattg tcacgatatc cttggtccat     780
ctatatgtat gggcatgagc gagtcgagaa aatgtaccgc gaaaaatcgt agtgacctgc     840
gcactgcgcc gttctaccac cgtaggattg aagtgaatct cgaattc                  887

<210> SEQ ID NO 37
<211> LENGTH: 34
<212> TYPE: PRT
<213> ORGANISM: Melanocarpus albomyces

<400> SEQUENCE: 37

Gln Lys Trp Gly Gln Cys Gly Gly Ile Gly Tyr Ser Gly Cys Thr Thr
1               5                   10                  15
```

```
Cys Lys Ala Gly Ser Thr Cys Pro Ala Gln Asn Glu Tyr Tyr Ser Gln
         20                  25                  30

Cys Leu
```

<210> SEQ ID NO 38
<211> LENGTH: 29
<212> TYPE: DNA
<213> ORGANISM: Unknown
<220> FEATURE:
<223> OTHER INFORMATION: PCR Primer

<400> SEQUENCE: 38
atagaattct aytgggaytg ytgyaarcc                                    29

<210> SEQ ID NO 39
<211> LENGTH: 26
<212> TYPE: DNA
<213> ORGANISM: Unknown
<220> FEATURE:
<223> OTHER INFORMATION: PCR Primer
<220> FEATURE:
<221> NAME/KEY: misc_feature
<222> LOCATION: (15)..(15)
<223> OTHER INFORMATION: n is a, c, g, or t

<400> SEQUENCE: 39
atagaattct trtcngcrtt ytgraa                                       26

<210> SEQ ID NO 40
<211> LENGTH: 17
<212> TYPE: DNA
<213> ORGANISM: Unknown
<220> FEATURE:
<223> OTHER INFORMATION: PCR Primer
<220> FEATURE:
<221> NAME/KEY: misc_feature
<222> LOCATION: (9)..(9)
<223> OTHER INFORMATION: n is a, c, g, or t

<400> SEQUENCE: 40
gaygaracng arcaymg                                                 17

<210> SEQ ID NO 41
<211> LENGTH: 17
<212> TYPE: DNA
<213> ORGANISM: Unknown
<220> FEATURE:
<223> OTHER INFORMATION: PCR Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 41
tangcnccnc cnggrtt                                                 17

<210> SEQ ID NO 42

```
<211> LENGTH: 17
<212> TYPE: DNA
<213> ORGANISM: Unknown
<220> FEATURE:
<223> OTHER INFORMATION: PCR Primer
<220> FEATURE:
<221> NAME/KEY: misc_feature
<222> LOCATION: (15)..(15)
<223> OTHER INFORMATION: n is a, c, g, or t

<400> SEQUENCE: 42
aarcaygart ayggnac                                              17

<210> SEQ ID NO 43
<211> LENGTH: 17
<212> TYPE: DNA
<213> ORGANISM: Unknown
<220> FEATURE:
<223> OTHER INFORMATION: PCR Primer
<220> FEATURE:
<221> NAME/KEY: misc_feature
<222> LOCATION: (12)..(12)
<223> OTHER INFORMATION: n is a, c, g, or t

<400> SEQUENCE: 43
ccrtaraart cnggrtt                                              17

<210> SEQ ID NO 44
<211> LENGTH: 15
<212> TYPE: DNA
<213> ORGANISM: Trichoderma reesei

<400> SEQUENCE: 44
ccgcggactg gcatc                                                15

<210> SEQ ID NO 45
<211> LENGTH: 16
<212> TYPE: DNA
<213> ORGANISM: Trichoderma reesei

<400> SEQUENCE: 45
ccgcggactg cgcatc                                               16
```